United States Patent
Neustadt et al.

(10) Patent No.: US 7,465,740 B2
(45) Date of Patent: Dec. 16, 2008

(54) 2-HETEROARYL-PYRAZOLO-[4,3-E]-1,2,4-TRIAZOLO-[1,5-C]-PYRIMIDINE ADENOSINE A2A RECEPTOR ANTAGONISTS

(75) Inventors: Bernard R. Neustadt, West Orange, NJ (US); Craig D. Boyle, Branchburg, NJ (US); Samuel Chackalamannil, Califon, NJ (US); Joel M. Harris, Watchung, NJ (US); Claire M. Lankin, High Bridge, NJ (US); Hong Liu, River Edge, NJ (US); Unmesh Shah, Green Brook, NJ (US); Andrew Stamford, Chatham, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/522,221

(22) Filed: Sep. 15, 2006

(65) Prior Publication Data

US 2007/0066620 A1 Mar. 22, 2007

Related U.S. Application Data

(60) Provisional application No. 60/718,502, filed on Sep. 19, 2005.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................... 514/267; 544/251
(58) Field of Classification Search ................ 514/267; 544/251
See application file for complete search history.

(56) References Cited

U.S. PATENT DOCUMENTS

| | | | |
|---|---|---|---|
| 5,565,460 | A | 10/1996 | Suzuki et al. |
| 6,630,475 | B2 | 10/2003 | Neustadt et al. |
| 6,653,315 | B2 | 11/2003 | Tulshian et al. |
| 6,897,217 | B2 | 5/2005 | Neustadt et al. |
| 7,064,204 | B2 * | 6/2006 | Baraldi et al. ............ 544/251 |
| 2004/0138235 | A1 * | 7/2004 | Grzelak et al. ......... 514/255.05 |
| 2005/0239795 | A1 * | 10/2005 | Neustadt et al. ........ 514/252.16 |

FOREIGN PATENT DOCUMENTS

| | | |
|---|---|---|
| WO | WO 95/01356 | 1/1995 |
| WO | WO 97/05138 | 2/1997 |
| WO | WO 98/52568 | 11/1998 |
| WO | WO 01/92264 | 12/2001 |
| WO | WO 02/055083 | 7/2002 |
| WO | WO 03/032996 | 4/2003 |
| WO | WO 2004/094431 | 11/2004 |
| WO | WO 2005/044245 | 5/2005 |
| WO | WO 2005/103055 | 11/2005 |

OTHER PUBLICATIONS

Golembiowska, K., et al., Striatal Adenosine A2A Receptor Blockade Increases Extracellular Dopamine Release Following L-DOPA Administration in Intact and Dopamine-denervated Rats, Neuropharmacology 47, 414-426 (2004).*
M. Saletu et al., Sleep Laboratory Studies in Restless Leg Syndrome Patients as Compared with Normals and Acute Effects of Ropinirole, Neuropsychobiology, 41:4, 190-199 (2000).
International Search Report (PCT/US2006/036127)—5 pages, dated Feb. 6, 2007.

* cited by examiner

*Primary Examiner*—James O. Wilson
*Assistant Examiner*—Erich A Leeser
(74) *Attorney, Agent, or Firm*—Krishna G. Banerjee

(57) ABSTRACT

Compounds having the structural formula I

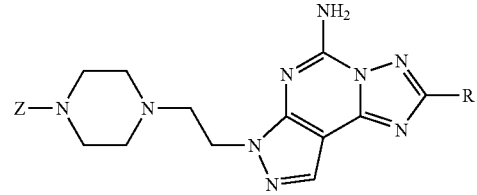

or a pharmaceutically acceptable salt thereof, wherein
R is $R^1$-isoxazolyl, $R^1$-oxadiazolyl, $R^1$-dihydrofuranyl, $R^1$-pyrazolyl, $R^1$-imidazolyl, $R^1$-pyrazinyl or $R^1$-pyrimidinyl;
$R^1$ is 1, 2 or 3 substituents selected from H, alkyl, alkoxy and halo;
Z is optionally substituted-aryl, or optionally substituted-heteroaryl;
are disclosed, as well as their use in the treatment of central nervous system diseases, in particular Parkinson's disease and Extra Pyramidal Syndrome, pharmaceutical compositions comprising them, and combinations with other agents.

17 Claims, No Drawings

2-HETEROARYL-PYRAZOLO-[4,3-E]-1,2,4-TRIAZOLO-[1,5-C]-PYRIMIDINE ADENOSINE A2A RECEPTOR ANTAGONISTS

This Application claims the benefit of U.S. Provisional Application No. 60/718,502 filed Sep. 19, 2005.

FIELD OF THE INVENTION

The present invention relates to 2-heteroaryl-pyrazolo-[4,3-e]-1,2,4-triazolo[1,5-c]pyrimidine adenosine $A_{2a}$ receptor antagonists, the use of said compounds in the treatment of central nervous system disorders including movement disorders, e.g., Parkinson's Disease, Extra-Pyramidal Syndrome, restless legs syndrome, essential tremor and Huntington's Disease; attention disorders, e.g., attention deficit hyperactivity disorder, cognitive impairment and negative symptoms of schizophrenia; and to other central nervous system diseases such as depression, stroke and psychoses. The invention also relates to pharmaceutical compositions comprising said compounds.

BACKGROUND

Adenosine is known to be an endogenous modulator of numerous physiological functions. At the cardiovascular system level, adenosine is a strong vasodilator and a cardiac depressor. In the central nervous system, adenosine induces sedative, anxiolytic and antiepileptic effects. In the respiratory system, adenosine induces bronchoconstriction. In the renal system, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ receptors inhibit, while $A_{2a}$ and $A_{2b}$ receptors stimulate the activity of the enzyme adenylate cyclase. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced probability of potentiating side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses.

Adenosine $A_{2a}$ receptor antagonists have been disclosed as being useful in the treatment or prevention of Extra Pyramidal Syndrome (EPS), dystonia, restless legs syndrome (RLS) or periodic limb movement in sleep (PLMS) in WO 05/044245, and have been disclosed as being useful in the treatment of attention deficit hyperactivity disorder (ADHD) in WO 02/055083.

EPS is a collective term for a series of adverse neurological reactions associated with the use of antipsychotic drugs. There are six different categories of EPS-related neurological syndromes of which four, dystonia, akathisia, pseudoparkinsonism (parkinsonian syndrome), and tardive dyskinesia, are particularly prevalent in patients taking antipsychotic medication. Dystonia is a painful spasm of the muscle groups of, in particular, the neck, jaw, back, pharynx, and larynx. It is most common in young males being treated with antipsychotic drugs, but can also be associated with the use of cocaine, tricyclic antidepressants, lithium and anticonvulsants such as phenytoin and carbamazepine. Pseudoparkinsonism manifests itself as akinesia (rigidity, stiffness and slow voluntary motion, stooped, shuffling walk) and tremor and these symptoms develop within weeks or months after initiation of therapy. Akathisia manifests itself as strong, subjective inner feelings of distress or discomfort characterized by motor restlessness. Often mistaken for agitation or anxiety, this common syndrome is frequently under-diagnosed and is the least responsive to treatment. Tardive dyskinesia is a late-appearing syndrome associated with chronic use of neuroleptic drugs. It occurs more frequently in older patients and is characterized by stereotypical, repetitive, involuntary, quick choreiform movements of the face, eyelids, mouth, tongue, extremities and trunk.

EPS is more prevalent with the use of typical antipsychotic agents but has also been reported with the use of atypical agents. Typical antipsychotics include loxapine, haloperidol, chlorpromazine, prochlorperazine and thiothixene. Atypical antipsychotics include clozapine, olanzapine, loxapine, quetiapine, ziprasidone, risperidone and aripiprazole.

Akathisia is also a characteristic of RLS and PLMS, as well as PLMD (periodic leg (or limb) movement disorder). RLS is a common disorder that causes patients to have an irresistible and unpleasant desire to move their legs; it usually manifests during periods of inactivity and/or at night, and can disturb sleep. Patients who do not have the typical RLS symptoms, but who do exhibit periodic leg movements that adversely impact sleep, are diagnosed with PLMS. Treatments for RLS and PLMS have included levodopa/carbidopa, levodopa/benserazide, dopamine agonists such as pramipexole and ropinerole, benzodiazepines, opioids, anticonvulsants and iron (ferrous sulfate). RLS and PLMS have been extensively described in the literature, for example by Saletu et al, *Neuropsychobiology*, 41, 4 (2000), p. 190-9.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists have been disclosed previously, for example in WO 95/01356; U.S. Pat. No. 5,565,460; WO 97/05138; WO 98/52568, U.S. Pat. Nos. 6,630,475, 6,653,315, 6,897,217 and PCT/US05/013454, filed Apr. 19, 2005.

SUMMARY OF THE INVENTION

The present invention relates to compounds having the structural formula I

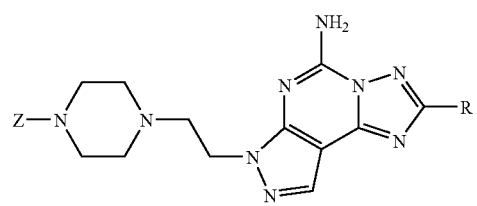

I or a pharmaceutically acceptable salt thereof, wherein

R is $R^1$-isoxazolyl, $R^1$-oxadiazolyl, $R^1$-dihydrofuranyl, $R^1$-pyrazolyl, $R^1$-imidazolyl, $R^1$-pyrazinyl or $R^1$-pyrimidinyl;

$R^1$ is 1, 2 or 3 substituents independently selected from the group consisting of H, alkyl, alkoxy and halo;

Z is $R^2$-aryl or $R^2$-heteroaryl;

$R^2$ is 1 to 5 substituents independently selected from the group consisting of hydrogen, alkyl, hydroxyalkyl, -alkylene-O—C(O)alkyl, alkoxyalkyl, (hydroxy)haloalkyl, (cycloalkyl)hydroxyalkyl, hydroxycycloalkyl, (halo)alkoxyalkyl, —C(O)alkyl, hydroxyalkoxy, alkoxyalkoxy, oxetanyloxy, halo, cyanoalkyl, haloalkyl, dialkylamino, $R^3$-heteroaryl and $R^3$-heteroarylalkyl; and $R^3$ is 1 to 3 substituents independently selected from the group consisting of H, alkyl, alkoxyalkyl, hydroxyalkyl, dialkylamino and cycloalkylaminocarbonyl.

Another aspect of the invention is a pharmaceutical composition comprising a therapeutically effective amount of at least one compound of formula I in a pharmaceutically acceptable carrier.

Yet another aspect of the invention is a method of treating central nervous system disorders including movement disorders, e.g., Parkinson's Disease, Extra-Pyramidal Syndrome, restless legs syndrome, essential tremor, Huntington's Disease, dystonia, periodic limb movement in sleep; attention disorders, e.g., attention deficit hyperactivity disorder, cognitive impairment and negative symptoms of schizophrenia; and to other central nervous system diseases such as depression, stroke and psychoses, comprising administering at least one compound of formula I to a mammal in need of such treatment.

In particular, the invention is drawn to the method of treating movement disorders such as Parkinson's disease, essential tremor or Huntington's Disease comprising administering at least one compound of formula I to a mammal in need of such treatment.

Still another aspect of the invention is a method of treating Parkinson's disease with a combination of at least one compound of formula I and one or more agents useful in the treatment of Parkinson's disease, for example dopamine; L-DOPA; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising at least one compound of formula I and one or more agents known to be useful in the treatment of Parkinson's in a pharmaceutically acceptable carrier.

The invention also relates to the treatment or prevention of EPS (e.g., dystonia, akathisia, pseudoparkinsonism and tardive dyskinesia) comprising administering at least one compound of formula I to a mammal in need of such treatment. In particular, this method is for the treatment or prevention of EPS in patients treated with an antipsychotic agent that has the side effect of inducing EPS. At least one compound of formula I can be administered after the symptoms of EPS have manifested, or at least one compound of formula I can be administered at the onset of administering an antipsychotic agent in order to prevent EPS from occurring. Thus, the invention also includes a method of treating or preventing EPS induced by an antipsychotic agent comprising administering a combination of an antipsychotic agent and at least one compound of formula I to a patient in need thereof.

The invention also relates to the treatment of primary (idiopathic) dystonia, and to the treatment or prevention of dystonia in patients who exhibit dystonia as a result of treatment with a tricyclic antidepressant, lithium or an anticonvulsant, or who have used cocaine, comprising administering a therapeutically effective amount of at least one compound of formula I to a patient in need thereof. When dystonia is caused by treatment with a tricyclic antidepressant, lithium or an anticonvulsant, at least one compound of formula I can be administered after the symptoms of dystonia have manifested, or at least one compound of formula I can be administered at the onset of administering a tricyclic antidepressant, lithium or an anticonvulsant in order to prevent dystonia from occurring. The invention, therefore, also includes a method of treating or preventing dystonia induced by a tricyclic antidepressant, lithium or an anticonvulsant comprising administering a combination of at least one compound of formula I and a tricyclic antidepressant, lithium or an anticonvulsant to a patient in need thereof.

The invention further relates to treatment of abnormal movement disorders such as RLS or PLMS, comprising administering to a patient in need thereof a therapeutically effective amount of at least one compound of formula I. The invention also comprises a method of treating RLS or PLMS comprising administering a combination of at least one compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

The invention also relates to the treatment of attention related disorders such as attention deficit disorder (ADD) and ADHD, as well as cognitive impairment and negative symptoms of schizophrenia, comprising administering an effective amount of at lease one compound of formula I to a patient in need thereof.

In another aspect, this invention relates to a kit comprising, in separate containers in a single package, pharmaceutical compositions for use in combination to treat Parkinson's Disease, wherein one container comprises a pharmaceutical composition comprising an effective amount of the compound of formula I in a pharmaceutically acceptable carrier, and wherein a separate container comprises a pharmaceutical composition comprising an effective amount of an agent useful in the treatment of Parkinson's disease.

In another aspect, this invention relates to a kit comprising, in separate containers in a single package, pharmaceutical compositions for use in combination to treat or prevent EPS caused by treatment with antipsychotic agent, wherein one container comprises a pharmaceutical composition comprising an effective amount of a compound of formula I in a pharmaceutically acceptable carrier, and wherein a separate container comprises a pharmaceutical composition comprising an effective amount of an antipsychotic agent.

In another aspect, this invention relates to a kit comprising, in separate containers in a single package, pharmaceutical compositions for use in combination to treat or prevent dystonia caused by treatment with a tricyclic antidepressant, lithium or an anticonvulsant, wherein one container comprises a pharmaceutical composition comprising an effective amount of a compound of formula I in a pharmaceutically acceptable carrier, and wherein a separate container comprises a pharmaceutical composition comprising an effective amount of a tricyclic antidepressant, lithium or an anticonvulsant.

In another aspect, this invention relates to a kit comprising, in separate containers in a single package, pharmaceutical compositions for use in combination to treat RLS or PLMS, wherein one container comprises a pharmaceutical composition comprising an effective amount of a compound of formula I in a pharmaceutically acceptable carrier, and wherein a separate container comprises a pharmaceutical composition comprising an effective amount of levodopa/carbidopa, levodopa/benserazide, a dopamine agonist, a benzodiazepine, an opioid, an anticonvulsant or iron.

The invention also relates to the use of a compound of formula I for the preparation of a medicament for treating or preventing Parkinson's Disease, EPS, dystonia, RLS, PLMS, essential tremor, Huntington's Disease, cognitive impairment or negative symptoms of schizophrenia, alone or in combination with the other agents discussed above.

DETAILED DESCRIPTION

Preferred compounds of formula I are those wherein R is $R^1$-pyrazinyl or $R^1$-dihydrofuranyl. $R^1$ is preferably one substituent selected from the group consisting of H and alkyl, more preferably H or methyl.

When Z is $R^2$-aryl, it is preferably $R^2$-phenyl, wherein $R^2$ is 1 to 3 substituents independently selected from the group consisting of halo, alkoxyalkyl or $R^3$-heteroaryl. More preferably, $R^2$ is two substituents, particularly wherein one substituent is 2-fluoro and the other is halo (especially fluoro), alkoxyalkyl (especially methoxyethoxy) or $R^3$-heteroaryl. The heteroaryl group in $R^3$-heteroaryl is preferably selected from oxazolyl, 1,2,4-oxadiazolyl, isoxazolyl and thiazolyl, with oxazolyl being more preferred; the $R^3$ substituent is preferably 1 or 2 groups independently selected from H, alkyl and alkoxyalkyl.

When Z is $R^2$-heteroaryl, preferred heteroaryl groups are benzoxazolyl, benzisoxazolyl and indazolyl, wherein $R^2$ is 1 to 3 substituents independently selected from the group consisting of H, halo and alkyl. More preferably, when the heteroaryl group is benzoxazolyl or benzisoxazolyl, $R^2$ is two substituents, particularly wherein one substituent is a fluoro group adjacent to the attachment point of Z and the other is H or an alkyl group on the oxazolyl or isoxazolyl portion of Z. When the heteroaryl group is indazolyl, $R^2$ is preferably three substituents, particularly wherein one substituent is a fluoro group adjacent to the attachment point of Z and the other two are alkyl groups on the indazolyl portion of Z.

As used herein, the term alkyl includes straight or branched aliphatic hydrocarbon chains of 1 to 6 carbon atoms, e.g., methyl, ethyl, isopropyl and t-butyl.

Aryl means an aromatic monocyclic or multicyclic ring system comprising 6 to about 14 carbon atoms, preferably 6 to about 10 carbon atoms. Non-limiting examples of suitable aryl groups include phenyl and naphthyl.

Heteroaryl means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Examples of benzofused heteroaryl groups are indazolyl, indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl, and 1,3,4-oxadizolyl and 1,2,4-oxadiazolyl. All isomers of benzoxazolyl and benzisoxazolyl are contemplated, for example

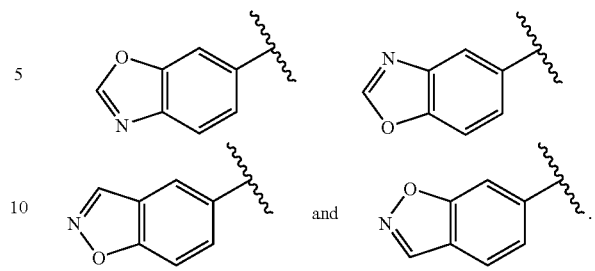

The term $R^2$-heteroaryl and $R^3$-heteroaryl refer to such groups wherein substitutable ring carbon atoms have a substituent as defined above, as well as groups wherein a substitutable ring nitrogen is substituted by H or alkyl. When the heteroaryl group is a benzofused ring, the substituents can be attached to either or both of the phenyl ring portion and the heteroaromatic ring portion, and the heteroaryl group can be attached to the rest of the molecule either through the phenyl ring portion or the heteroaromatic ring portion, preferably through the phenyl portion.

Hydroxyalkyl means a HO-alkyl-group in which alkyl is as previously defined. Non-limiting examples of suitable hydroxyalkyl groups include hydroxymethyl and 2-hydroxyethyl.

Alkoxy means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

Haloalkyl and haloalkoxy mean an alkyl or alkoxy chain as defined herein above one or more (e.g., 1 to 5) hydrogen atoms are replaced by halogen atoms, e.g., —$CF_3$, $CF_3CH_2CH_2$—, $CF_3CF_2$— or $CF_3O$—.

Cycloalkyl means a non-aromatic monocyclic ring system comprising 3 to about 6 carbon atoms. Non-limiting examples of suitable monocyclic cycloalkyls include cyclopropyl, cyclopentyl and cyclohexyl. "Cycloalkyloxy" therefore means a cycloalkyl-O— group. "Hydroxycycloalkyl" means a cycloalkyl group substituted with t hydroxy group.

Halo is fluoro, chloro, bromo or iodo.

Alkylene means a divalent alkyl chain obtained by removal of 2 hydrogen atoms from an alkyl group as defined above. Non-limiting examples of alkylene include methylene (—$CH_2$—), ethylene(—$CH_2$—$CH_2$—) and propylene ((—$CH_2$)$_3$—) or —$CH(CH_3)$—$CH_2$—)

The term (cycloalkyl)hydroxyalkyl means a hydroxyalkyl group substituted by a cycloalkyl group. Similarly, the term (hydroxy)haloalkyl means a haloalkyl group substituted by 1 or 2 hydroxyl groups, and (halo)alkoxy means an alkoxy group substituted by 1 to 3 halo atoms.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

Lines drawn into the ring systems, such as, for example:

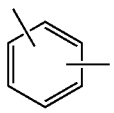

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

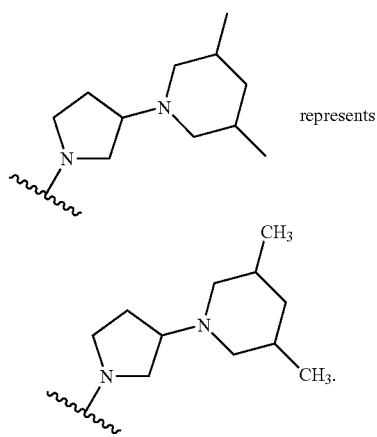

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Polymorphic forms of the compounds of formula I, and of the salts, solvates and prodrugs of the compounds of formula I, are intended to be included in the present invention.

"Effective amount" or "therapeutically effective amount" is meant to describe an amount of compound or a composition of the present invention effective as an adenosine $A_{2a}$ receptor antagonist and thus producing the desired therapeutic effect in a suitable patient.

"Patient" includes both human and animals.

"Mammal" means humans and other mammalian animals.

The compounds of formula I form salts that are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydro-abietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

Antipsychotic agents causing the EPS treated by adenosine $A_{2a}$ receptor antagonists and for use in combination with adenosine $A_{2a}$ receptor antagonists include typical and atypical antipsychotic agents. Typical antipsychotics include loxapine, haloperidol, chlorpromazine, prochlorperazine and thiothixene. Atypical antipsychotics include clozapine, olanzapine, loxapine, quetiapine, ziprasidone, risperidone and aripiprazole.

Tricyclic antidepressants causing dystonia treated by adenosine $A_{2a}$ receptor antagonists include perphenazine, amitriptyline, desipramine, doxepin, trimipramine and protriptyline. Anticonvulsants which may cause dystonia, but which also may be useful in treating ERLS or PLMS include phenytoin, carbamazepine and gabapentin.

Dopamine agonists useful in treating RLS and PLMS include pergolide, pramipexole, ropinerole, fenoldopam and cabergoline.

Opioids useful in treating PRLS and PLMS include codeine, hydrocodone, oxycodone, propoxyphene and tramadol.

Benzodiazepines useful in treating PRLS and PLMS include clonazepam, triazolam and temazepam.

The antipsychotics, tricyclic antidepressants, anticonvulsants, dopamine agonists, opioids and benzodiazepines are commercially available and are described in the literature, e.g., in The Physicians' Desk Reference (Montvale: Medical Economics Co., Inc., 2001).

It is contemplated that one or more compounds of formula I could be administered in combination with one or more other agents (e.g., antipsychotics, tricyclic antidepressants, anticonvulsants, dopamine agonists, opioids or benzodiazepines), although administration of one compound of formula I in combination with one other agent is preferred for each of the indications. While administration of separate dosage forms of the compound of formula I and the other agent(s) are preferred, it is also contemplated that the other agent(s) could be combined in a single dosage form with the compound of formula I for the treatment or prevention of Parkinson's disease, EPS, dystonia, RLS or PLMS.

Compounds of formula I can be prepared by known methods from starting materials either known in the art or prepared by methods known in the art; see, for example, WO 95/01356, *J. Med. Chem.*, 39 (1996) 1164-1171, U.S. Pat. No. 6,630,475 and U.S. Pat. No. 6,897,217.

Additional non-limiting examples of suitable methods are illustrated in Schemes 1 and 2. In the Schemes, Q is a protecting group, preferably t-butoxycarbonyl (Boc) and R and Z are as defined above.

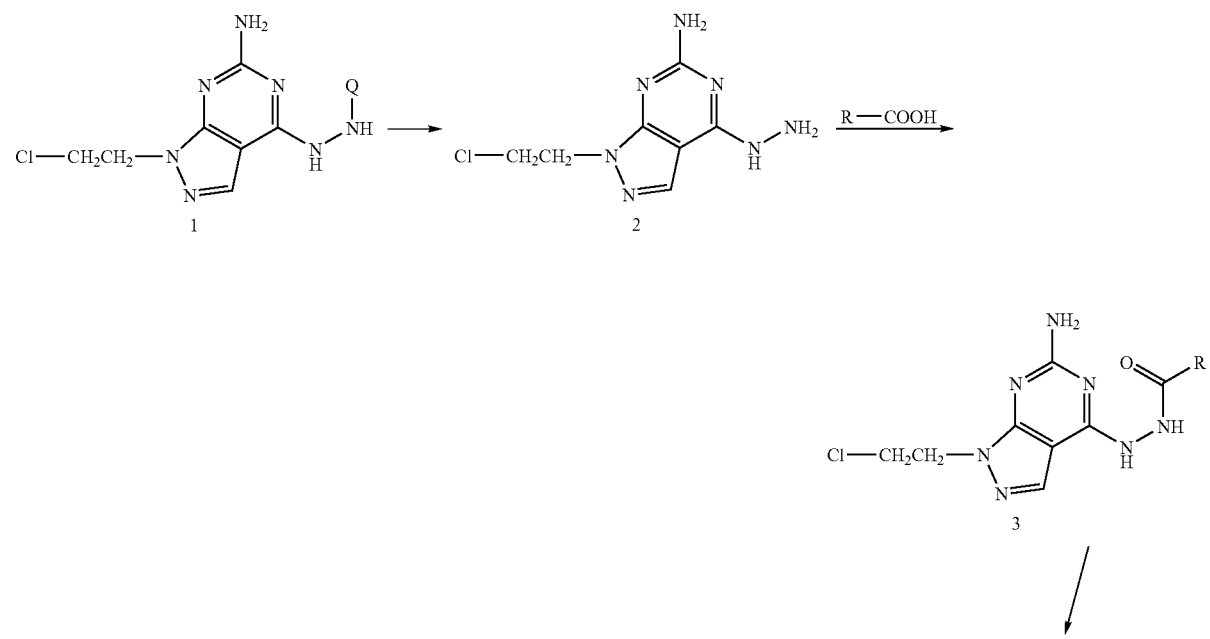

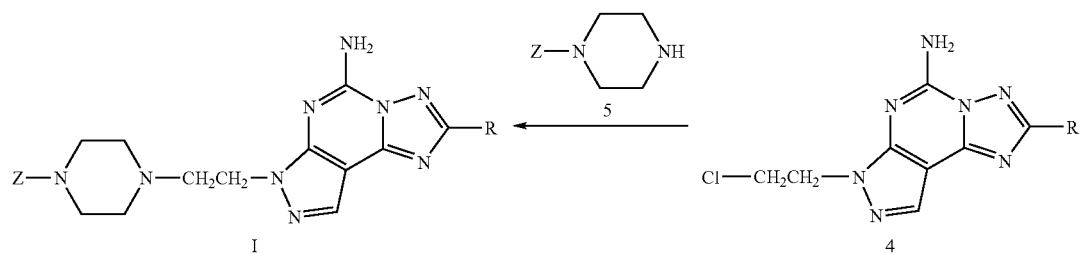

Compound 1 is deprotected (for example when the protective group Q in 1 is Boc, treatment with HCl/dioxane furnishes hydrazine 2), and 2 is acylated with a carboxylic acid, for example, with the acid and a carbodiimide, or with a preformed mixed anhydride, such as that with isopropyl chloroformate. The resultant hydrazide 3 is cyclized with N,O-bis (trimethylsilyl)acetamide in DMF at 120° C., or other known cyclization methods can be used. Amination of 4 with piperazine 5 to yield I takes place at temperatures of 100-160° C., preferably in DMF and in the presence of KI. Heating may also be effected by microwave irradiation in a sealed vessel yielding temperatures of 190-210° C.

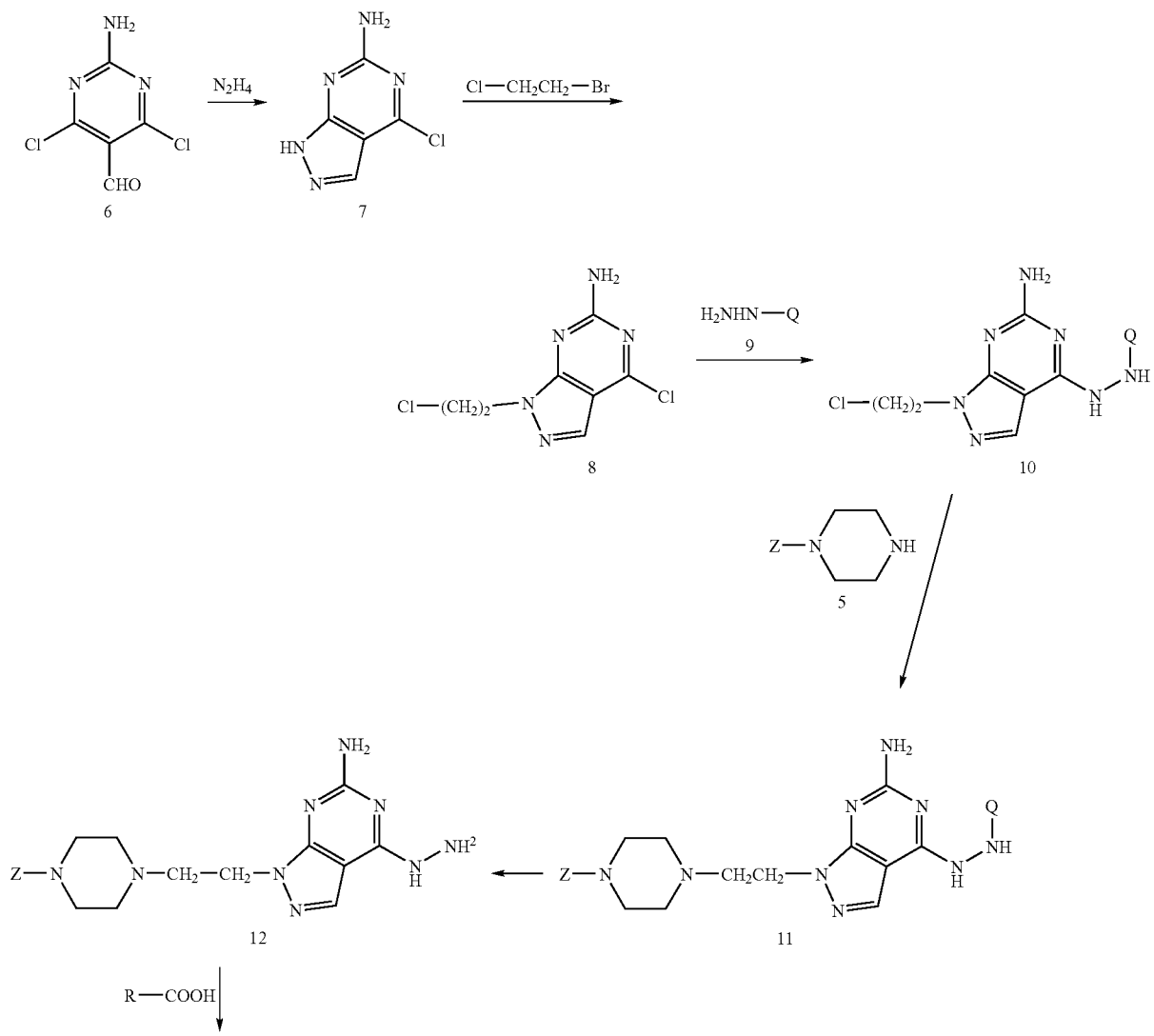

-continued

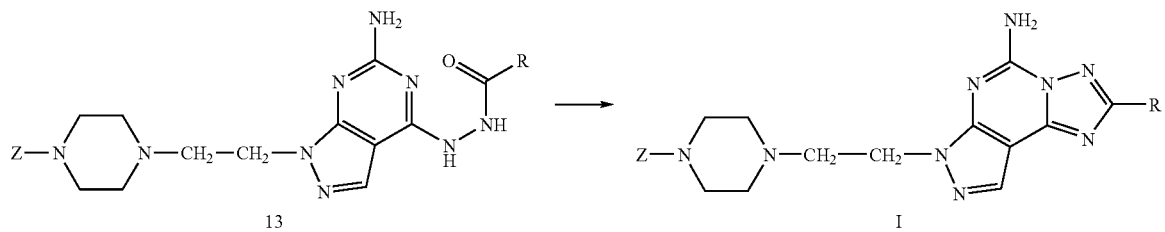

In Scheme 2, aldehyde 6 is reacted with hydrazine to furnish 7, preferably in DMF at room temperature. Reaction of 7 with an alkylating reagent, such as 1-bromo-2-chloroethane, yields chloride 8. This conversion is carried out in the presence of a base such as $K_2CO_3$, in a solvent such as DMF at room temperature. Reaction of 8 with 9, a protected form of hydrazine, furnishes 10. The reaction is best carried out in DMF at elevated temperature of 80-100° C. Compound 10 is converted to 11 by reaction with a piperazine 5. The reaction is preferably carried out in DMF at elevated temperatures of 80-100° C. with catalytic KI. Deprotection of 11 and acylation of 12 are accomplished as for 1 and 2 in Scheme 1, respectively, and hydrazide 13 is cyclized to I in the same manner 3 in Scheme 1.

In certain cases, the initial R group may contain a protective group, such as t-butyldimethylsilyl for an alcohol. The protective group may be removed following the conversion to formula I by employing well known methods.

In the above schemes, one compound of formula I can be converted to a different compound of formula I by well-known methods, such as reduction of a ketone to an alcohol with $NaBH_4$.

Abbreviations used in the specification are as follows: Me (methyl); Bu (butyl); Et (ethyl); Boc (t-butoxycarbonyl); DMF (dimethylformamide); THF (tetrahydrofuran); DIPEA (diisopropylethylamine); RT (room temperature); BSA (N,O-bis(trimethylsilyl)-acetamide); BINAP (2,2'-bis(diphenylphosphino)-1,1'-binaphthyl); PLC (preparative layer chromatography); TFA (trifluoroacetic acid); HOBt (hydroxybenzotriazole); DAST (diethylaminosulfur trifluoride); EDCl (1-(3-dimethylaminopropyl)-3-ethyl-carbodiimide hydrochloride); Ms (methanesulfonate); TBAF (tetrabutylammonuim fluoride); TBS (t-butyldimethylsilyl); and TMS (trimethylsilyl).

Preparation 1

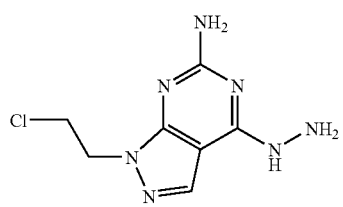

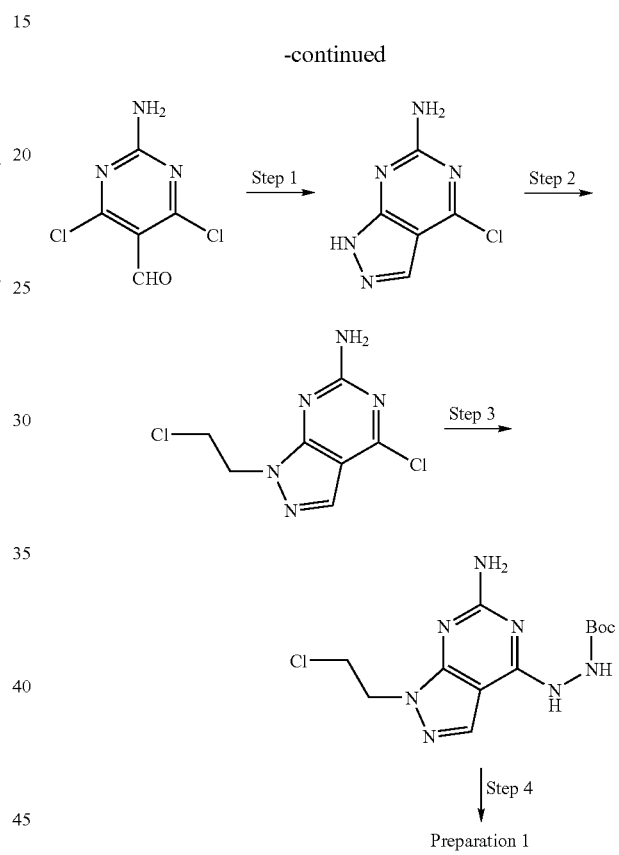

Preparation 1

Step 1: To 2-amino-4,6-dichloropyrimidine-5-carboxaldehyde (25.0 g, 130 mmol) in DMF (100 ml) add DIPEA (28.4 ml, 163 mmol) and then hydrazine hydrate (6.32 ml, 130 mmol). After the initial exotherm, stir 24 h and concentrate in vacuo to ~50 g. Add water (50 ml), filter, wash with water, and dry to give the monochloride as a brown solid.

Step 2: To the product of Step 1 (15.0 g, 88 mmol) in DMF (150 ml) add 60% NaH in mineral oil (4.25 g, 106 mmol). Add slowly 1-bromo-2-chloroethane (22.1 ml, 265 mmol). Stir at RT 2 h, concentrate, and chromatograph on silica to obtain the dichloride as an off-white solid.

Step 3: Combine the product of Step 2 (12.2 g, 52.5 mmol) and t-butyl carbazate (8.33 g, 63 mmol) in DMF (70 ml). Heat at 80° C. 24 h, allow to cool, concentrate, and chromatograph on silica to obtain the carbazate as a white solid.

Step 4: Dissolve the product of Step 3 (5.0 g, 15 mmol) in 1:1 MeOH—CH$_2$Cl$_2$ (100 ml). Add 4.0M HCl/dioxane (40 ml, 160 mmol) and allow to stand 18 h. Add conc. NH$_4$OH to pH=11. Concentrate, treat with water, filter, wash with water, and dry to obtain the hydrazine as a brown solid.

Preparation 2

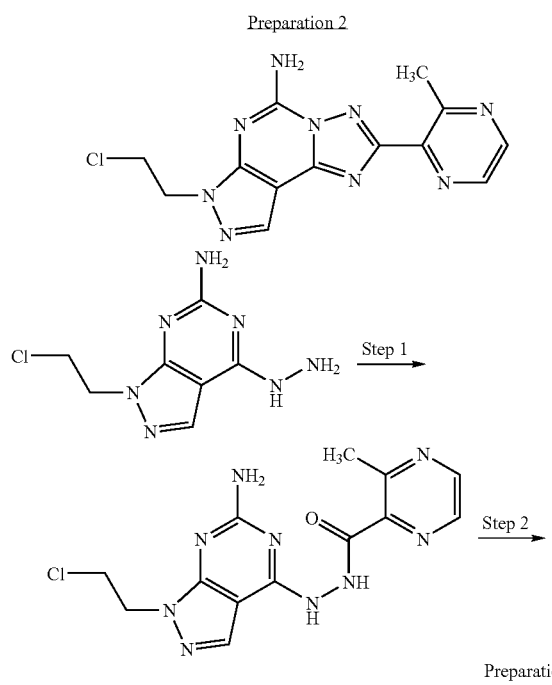

Preparation 2

Step 1: To the product of Preparation 1 (1.00 g, 4.4 mmol) in DMF (15 ml) add 3-methylpyrazine-2-carboxylic acid (0.73 g, 5.3 mmol), HOBt hydrate (0.71 g, 5.3 mmol), EDCl (10.1 g, 5.3 mmol), and N-methylmorpholine (0.58 ml, 5.3 mmol). Stir 20 h and concentrate to obtain the crude hydrazide.

Step 2: To the crude product of Step 1 add BSA (40 ml). Heat at 120° C. 24 h, allow to cool, and concentrate. Pre-adsorb on silica and chromatograph to obtain a tan solid. Treat with MeOH (10 ml), filter, and wash with MeOH to obtain the title compound as an off-white solid.

In similar fashion, from the product of Preparation 1 and the appropriate carboxylic acid, produce Preparations 2-2 to 2-13.

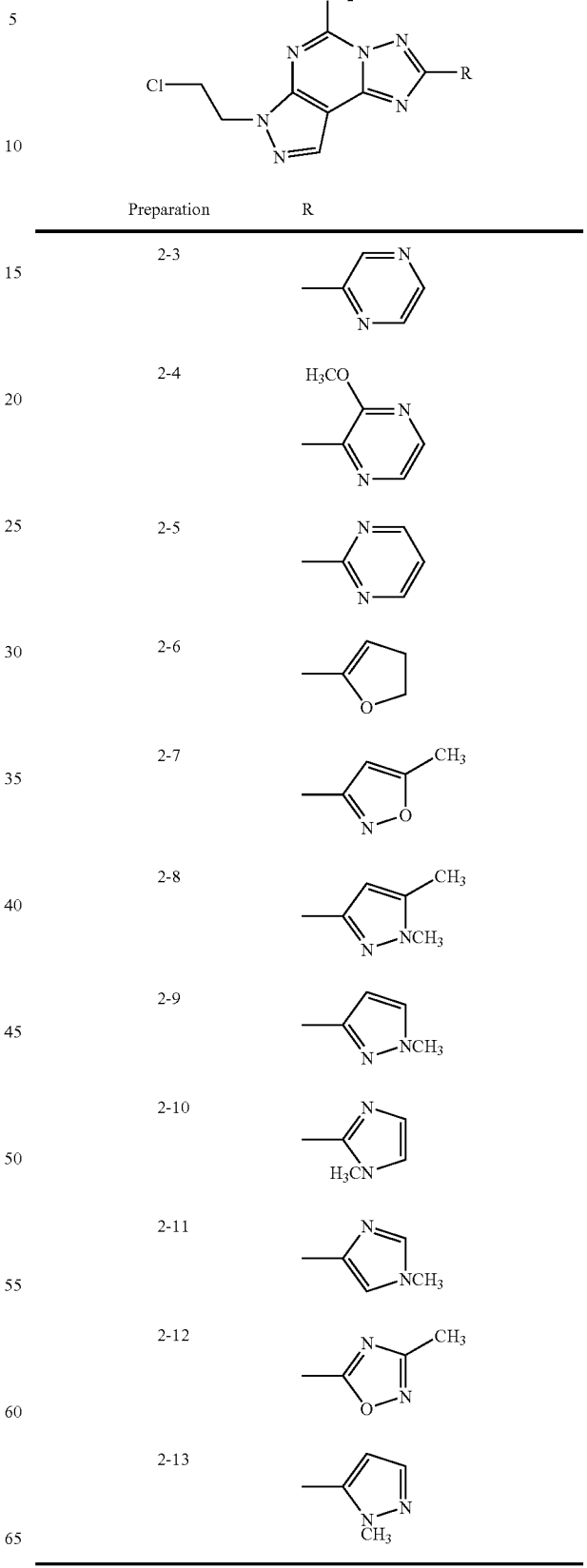

Preparation 3

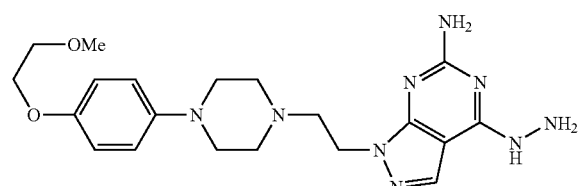

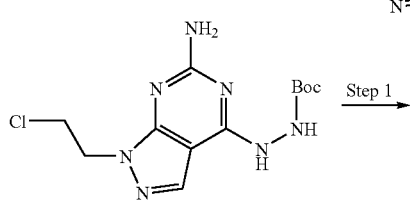

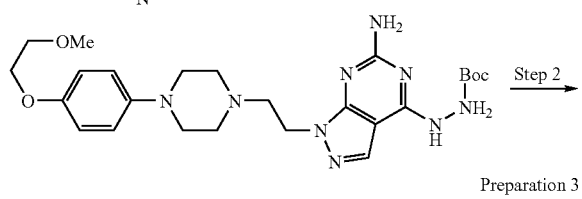

Preparation 3

Step 1: Combine the product of Preparation 1, Step 3 (6.04 g, 18.4 mmol), 1-(4-(2-methoxyethoxy)phenyl)piperazine (8.71 g, 37 mmol), and KI (3.06 g, 18 mmol) in DMF (60 ml). Heat at 90° C. 72 h, allow to cool, and concentrate. Partition between $CH_2Cl_2$ and water, wash with 1N NaOH, then brine, dry ($MgSO_4$) and concentrate. Chromatograph on silica to obtain the carbazate as a brown solid.

Step 2: Dissolve the product of Step 1 (6.0 g, 11.4 mmol) in 1:1 MeOH—$CH_2Cl_2$ (70 ml). Add 4.0M HCl/dioxane (35 ml, 140 mmol) and allow to stand 24 h. Add a solution of NaOH (7.0 g) in water (20 ml). Concentrate, treat with water, filter, wash with water, then EtOAc, and dry to obtain the hydrazine as a grey solid.

Preparation 4

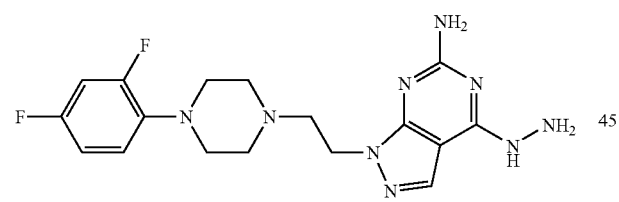

In a fashion similar to Preparation 3, employ 1-(2,4-difluorophenyl)piperazine to produce the title hydrazine as a beige solid.

Preparation 5

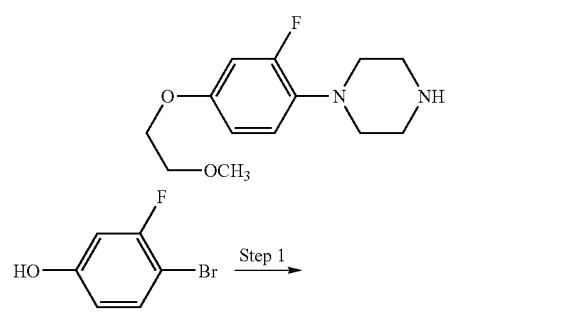

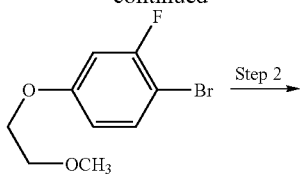

Preparation 5

Step 1: Combine 4-bromo-3-fluorophenol (3.00 g, 12.0 mmol) and NaH (60% in oil, 2.30 g, 57 mmol) in DMF (25 ml). Add 2-bromoethyl methyl ether (4.32 ml, 61 mmol). Heat at 60° C. 4 h and concentrate. Partition with EtOAc and 1N NaOH. Wash with brine, dry ($MgSO_4$) and concentrate to obtain the ether as a yellow oil.

Step 2: Combine the product of Step 1 (4.889, 26 mmol), piperazine (6.22 g, 72 mmol), NaO-t-Bu (1.62 g, 16.9 mmol), (±)-BINAP (0.45 g, 0.7 mmol) and $Pd_2dba_3$ (0.14 g, 0.24 mmol) in toluene (25 ml). Heat at 110° C. 8 h, allow to cool, and extract with 1N HCl (100 ml). Basify the aqueous with 1N NaOH to pH 10. Extract with $CH_2Cl_2$, dry ($MgSO_4$) and concentrate to obtain the aryl-piperazine as a brown oil.

Preparation 6

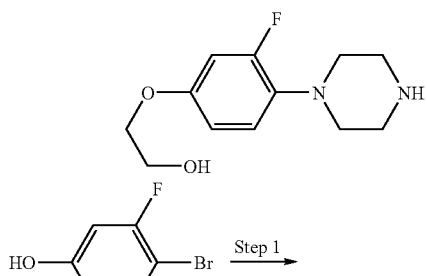

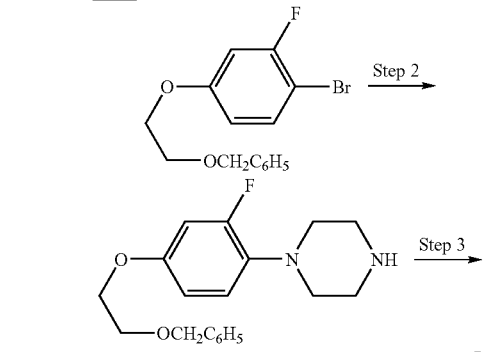

Preparation 6

Steps 1 and 2: From 4-bromo-3-fluorophenol and 2-bromoethyl benzyl ether, using the procedure according to Preparation 5, Steps 1 and 2, produce the aryl-piperazine as a black oil.

Step 3: To the product of Step 2 (2.62 g, 7.9 mmol) in MeOH—EtOAc (1:1, 40 ml) add 5% Pd/C (0.60 g) and 1N HCl (8 ml). Hydrogenate at 60 psi 16 h and filter through celite. Add 1N NaOH (8 ml), concentrate, and extract the residue with ethanol (200 ml). Filter and concentrate to obtain the alcohol as a brown oil.

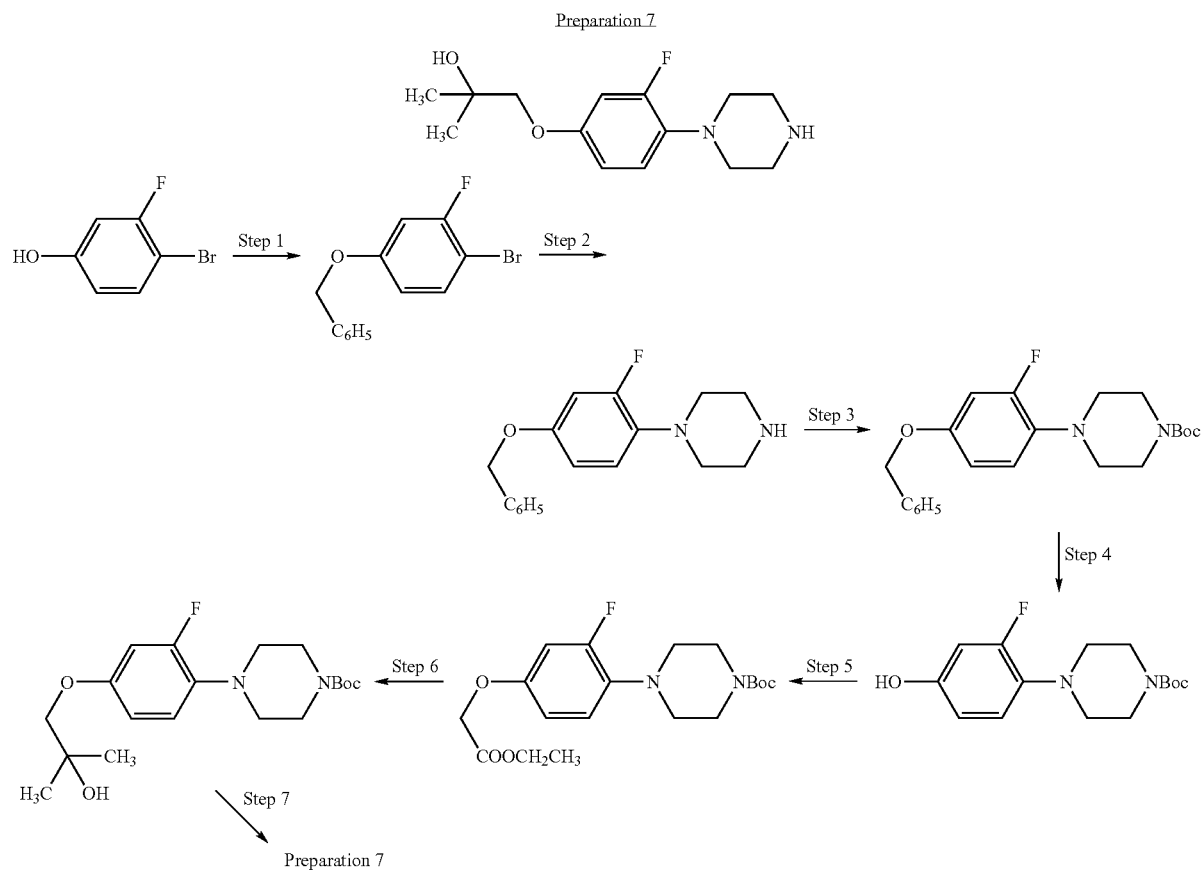

Preparation 7

Step 1: Treat 4-bromo-3-fluorophenol with benzyl bromide according to Preparation 6, Step 1 (reaction temperature 60° C.), to obtain the ether as a yellow oil.

Step 2: Treat the product of Step 1 with piperazine according to Preparation 5, Step 2, to obtain the aryl-piperazine as a yellow solid after chromatography.

Step 3: To the product of Step 2 (1.74 g, 6.1 mmol) in $CH_2Cl_2$ (15 ml) add $Et_3N$ (1.02 ml, 7.3 mmol), followed by $Boc_2O$ (1.33 g, 61 mmol). After 1 h, wash with 1N $NaHCO_3$, then 1N HCl, then brine. Dry ($MgSO_4$) and concentrate to obtain the Boc-derivative as a brown solid.

Step 4: Add the product of Step 3 (2.55 g, 6.6 mmol) to 5% Pd/C (0.60 g) in $CH_3OH$ (30 ml). Hydrogenate at 58 psi 20 h. Filter through celite and concentrate to obtain the phenol as a white solid.

Step 5: Treat the product of Step 4 with ethyl chloroacetate according to the procedure of Step 1 to obtain the ester as a brown oil.

Step 6: Dilute 3.0M ethereal $CH_3MgBr$ (2.3 ml, 6.9 mmol) with ether (6 ml) and cool in ice. Add dropwise a solution of the product of Step 5 (1.04 g, 2.7 mmol) in ether (6 ml). Allow to warm to RT, and add another 2.3 ml of Grignard reagent. Stir 2 h, quench with $NH_4Cl$, and wash with water, then brine. Dry ($MgSO_4$) and concentrate to obtain the alcohol as a yellow oil.

Step 7: To the product of Step 6 (1.68 g, 4.6 mmol) in $CH_2Cl_2$ (15 ml) add TFA (10 ml). Stir 1 h, concentrate, and dissolve in 1N NaOH. Saturate with NaCl and extract with $CH_2Cl_2$ (4×). Wash with brine, dry ($MgSO_4$), and concentrate to obtain the title compound as a yellow oil.

Preparation 8

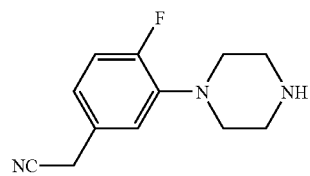

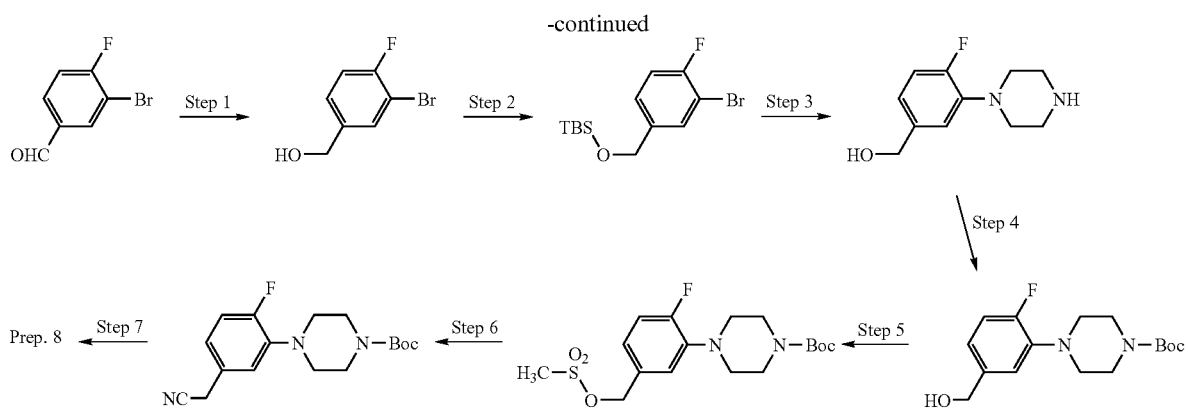

Step 1: To a solution of 3-bromo-4-fluorobenzaldehyde (1.20 g, 5.9 mmol) in EtOH (20 ml) add NaBH$_4$ (0.103 g, 2.7 mmol). Stir 2 h, concentrate, and partition between ether and water, with NH$_4$Cl (0.6 g) added. Dry (MgSO$_4$) and concentrate to obtain the alcohol as a colorless oil.

Step 2: To the product of Step 1 (5.4 g, 26 mmol) in DMF (20 ml) at 0° C. add t-butyldimethylsilyl chloride (4.17 g, 28 mmol) and imidazole (2.69 g, 40 mmol). Stir 2 h and partition between 1:1 ether-hexane and water. Wash with brine, dry (MgSO$_4$) and concentrate to obtain the product as a colorless oil.

Step 3: Treat the product of Step 2 with piperazine according to the procedure of Preparation 5, Step 2, to obtain the aryl-piperazine as a yellow solid.

Step 4: Convert the product of Step 3 (3.30 g, 16.8 mmol) to a solution of the Boc-derivative according to Preparation 7, Step 3.

Step 5: To the solution from Step 4 add EbN (2.60 ml, 18.5 mmol), followed by CH$_3$SO$_2$Cl (2.12 g, 18.5 mmol). Stir 2 h, add ether (40 ml), and filter to give a solution of the crude methanesulfonate ester.

Step 6: Treat the product of Step 5 with 3 equivalents of KCN in 5:1 EtOH-water. Reflux 18 h, concentrate, and partition between ether and water. Wash with brine, dry (MgSO$_4$) concentrate, and chromatograph on silica to obtain the product as a yellow oil.

Step 7: Add the product of Step 6 (1.6 g, 4.6 mmol) to TFA (15 ml) at 0° C. Stir 2 h, concentrate, and treat the residue with conc. NH$_4$OH. Extract with CH$_2$Cl$_2$, dry (MgSO$_4$) and concentrate to obtain the title compound as a yellow oil.

Preparation 9

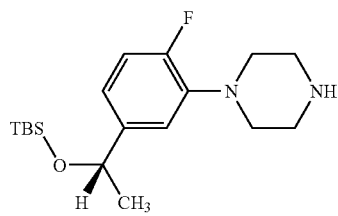

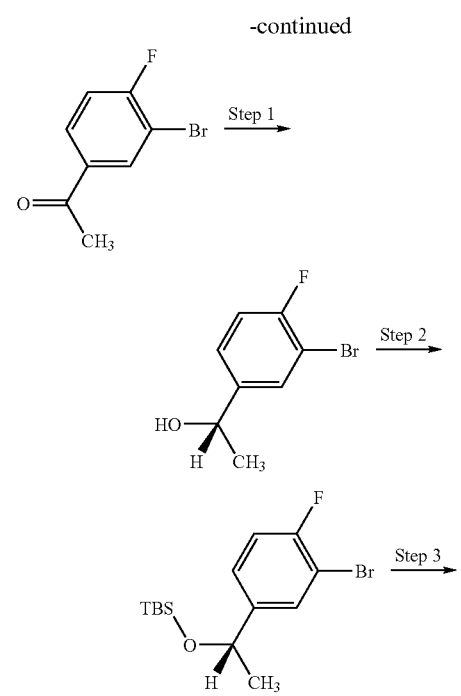

Preparation 9

Step 1: To (R)-2-methyl-CBS-oxazaborolidine (1.0M in toluene, 7.1 ml, 7.1 mmol) add BH$_3$.Me$_2$S (2.0M in THF, 3.0 ml, 6.0 mmol). Stir 0.5 h and cool to −78° C. Add 3'-bromo-4'-fluoroacetophenone(1.50 g, 6.9 mmol). Allow to warm to −20° C. and stir 5 h at −20° C. Add slowly MeOH (20 ml). Concentrate and chromatograph on silica to obtain the alcohol as a colorless oil.

Steps 2 and 3: Convert the product of Step 1 to the aryl-piperazine according to Preparation 8, Steps 2 and 3, modifying the work-up of the piperazine reaction by concentrating, partitioning with CH$_2$Cl$_2$ and water, drying (MgSO$_4$), and concentrating to obtain the product TBS-ether as a yellow oil.

In similar fashion, using (S)-2-methyl-CBS-oxazaborolidine, produce the enantiomer, Preparation 9-2, as a yellow oil.

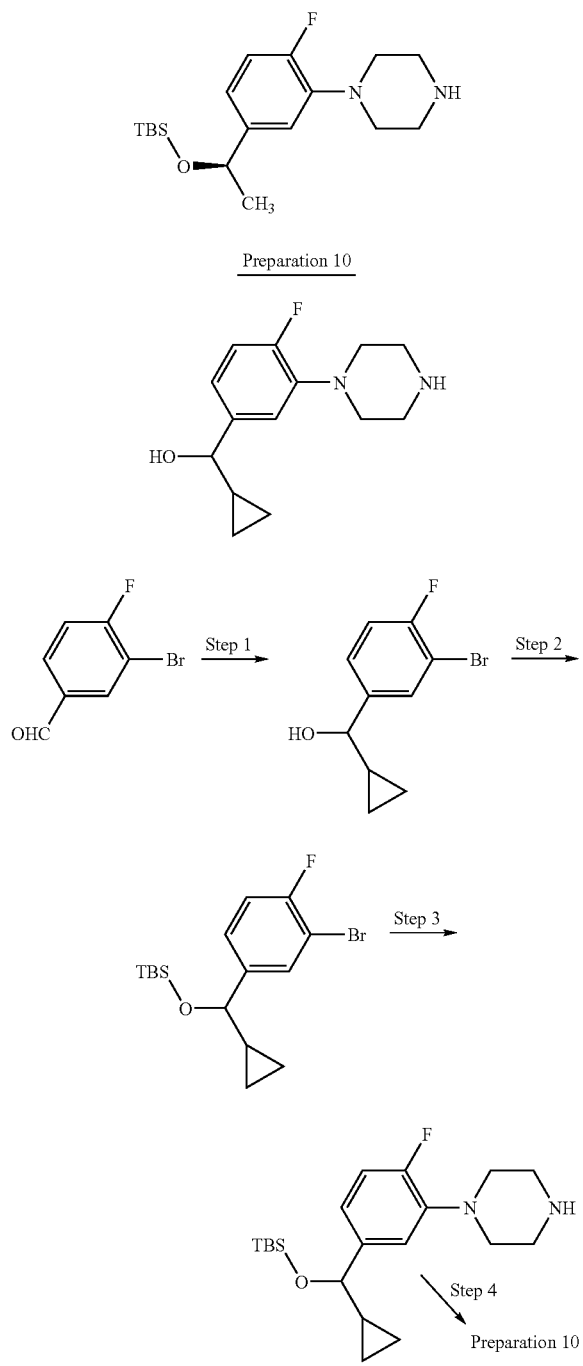

Preparation 10

Step 1: To a solution of 3-bromo-4-fluorobenzaldehyde (2.00 g, 9.9 mmol) in THF (20 ml) at 0° C. add dropwise cyclopropylmagnesium bromide (0.5M in THF, 27.6 ml, 13.8 mmol). Stir 1 h, allow to warm, and add 12% NH₄Cl (100 ml). Extract with ether, dry (MgSO₄), and concentrate to obtain the alcohol as a yellow oil.

Step 2 and 3: Treat the alcohol of Step 1 according to Preparation 9, Steps 2 and 3, to obtain the aryl-piperazine as a black oil.

Step 4: To the TBS ether (0.45 g, 1.23 mmol) in THF (10 ml) add TBAF (1.0M in THF, 1.5 ml, 1.5 mmol). Stir 4 h, add CH₃OH (10 ml), concentrate, and purify on PLC to obtain the alcohol as a yellow oil.

Preparation 11

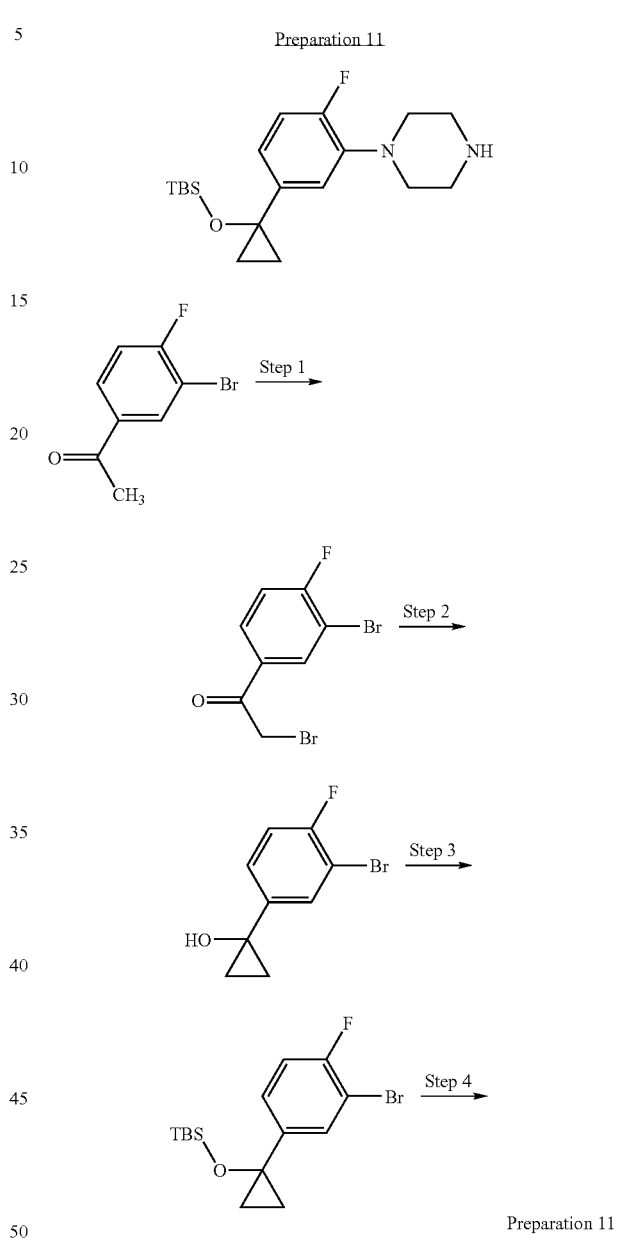

Preparation 11

Step 1: To 3'-bromo-4'-fluoroacetophenone (3.00 g, 13.8 mmol) in CH₂Cl₂ (15 ml) and acetic acid (0.5 ml) at 10° C. add dropwise bromine (2.43 g, 15.2 mmol) in CH₂Cl₂ (20 ml). Stir 15 min and concentrate to obtain the crude bromide as a yellow oil.

Step 2: Cool to 0° C. a suspension of samarium powder (6.24 g, 41.5 mmol) in THF (40 ml). Combine the crude product of Step 1 above with CH₂I₂ (11.19 g, 41.5 mmol) in THF (60 ml) and add dropwise to the suspension. Stir 0.5 h and add slowly 1N HCl (200 ml). Extract with ether, dry (MgSO₄), concentrate, and chromatograph on silica to obtain the cyclopropanol as a yellow oil.

Steps 3 and 4: Convert the product of Step 2 to the aryl-piperazine according to Preparation 9, Steps 2 and 3, to obtain the product TBS-ether as a yellow oil.

Preparation 12

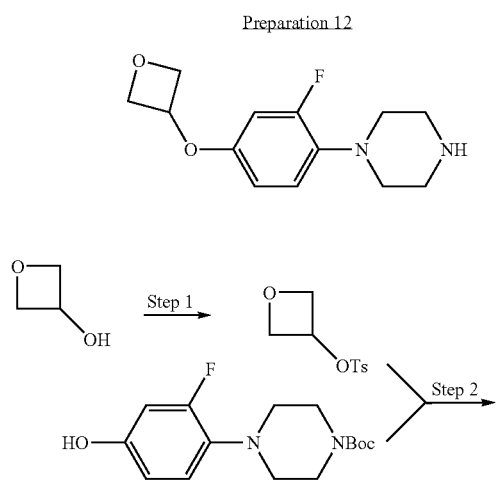

Step 1: Combine oxetan-3-ol (prepared according to *J. Org. Chem.* 1983, 2953, 3.64 g, 52 mmol) and ptoluenesulfonyl chloride (11.9 g, 62 mmol) in water (10 ml) and add NaOH (3.3 g, 83 mmol) in water (4 ml). Stir 2 h at RT, then 0.5 h at 65° C. Filter and chromatograph the solid on silica to obtain the tosylate as a white solid.

Step 2: Treat the product of Step 1 with the product of Preparation 7, Step 4, according to Preparation 5, Step 1 (120° C. 18 h), to obtain the ether as a yellow oil.

Step 3: Deprotect the product of Step 2 according to Preparation 7, Step 7, and purify by PLC to obtain the title compound as a yellow solid.

Preparation 13

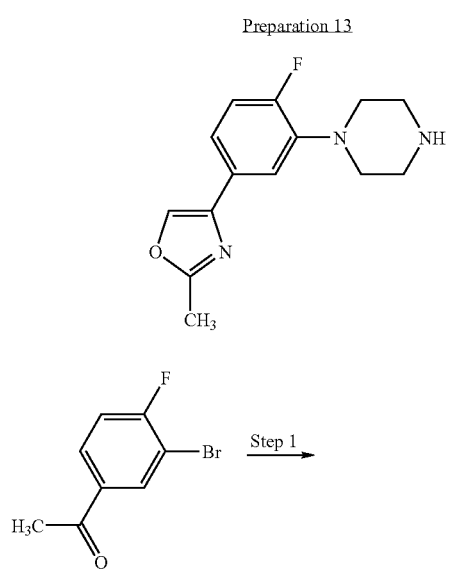

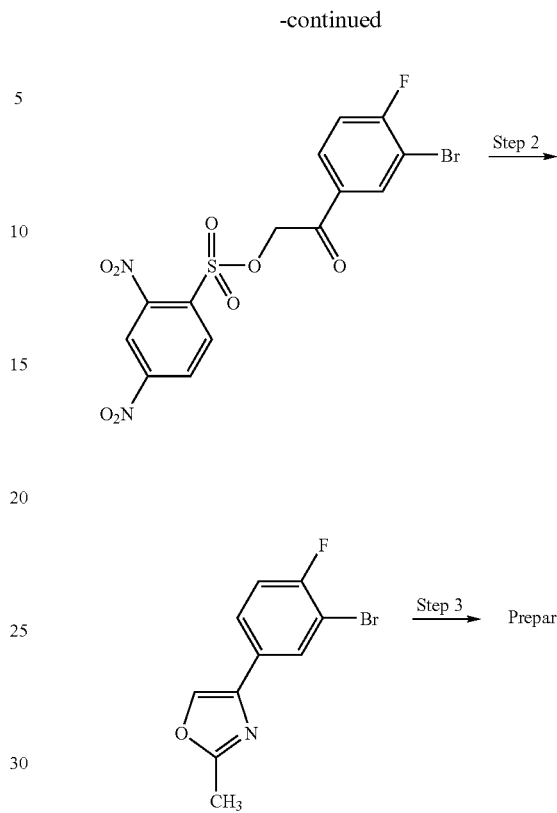

Step 1 and 2: Convert 3'-bromo-4'-fluoroacetophenone to the 2-(2,4-dinitrobenzene-sulfonyloxy) derivative according to the procedure of *Synth. Comm.* 2003, 1611, and react this with acetamide in CH$_3$CN (reflux 18 h) to give, after chromatography on silica, the oxazole as a white solid.

Step 3: React the product of Step 2 with piperazine according to Preparation 5, Step 2, to obtain the aryl-piperazine as a yellow oil.

Similarly, from 3'-bromo-4'-fluoropropiophenone, produce Preparation 13-2:

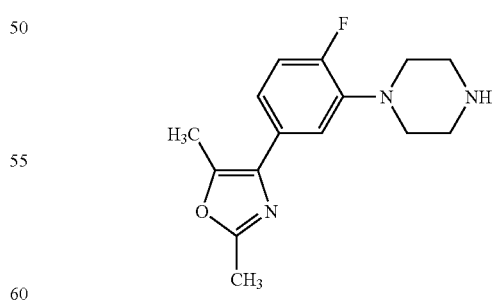

In similar fashion, from 3'-bromo-2'-fluoroacetophenone (prepared from 2-bromofluorobenzene by treatment first with BuLi and TMS-Cl and then with acetyl chloride and AlCl$_3$), produce Preparation 13-3:

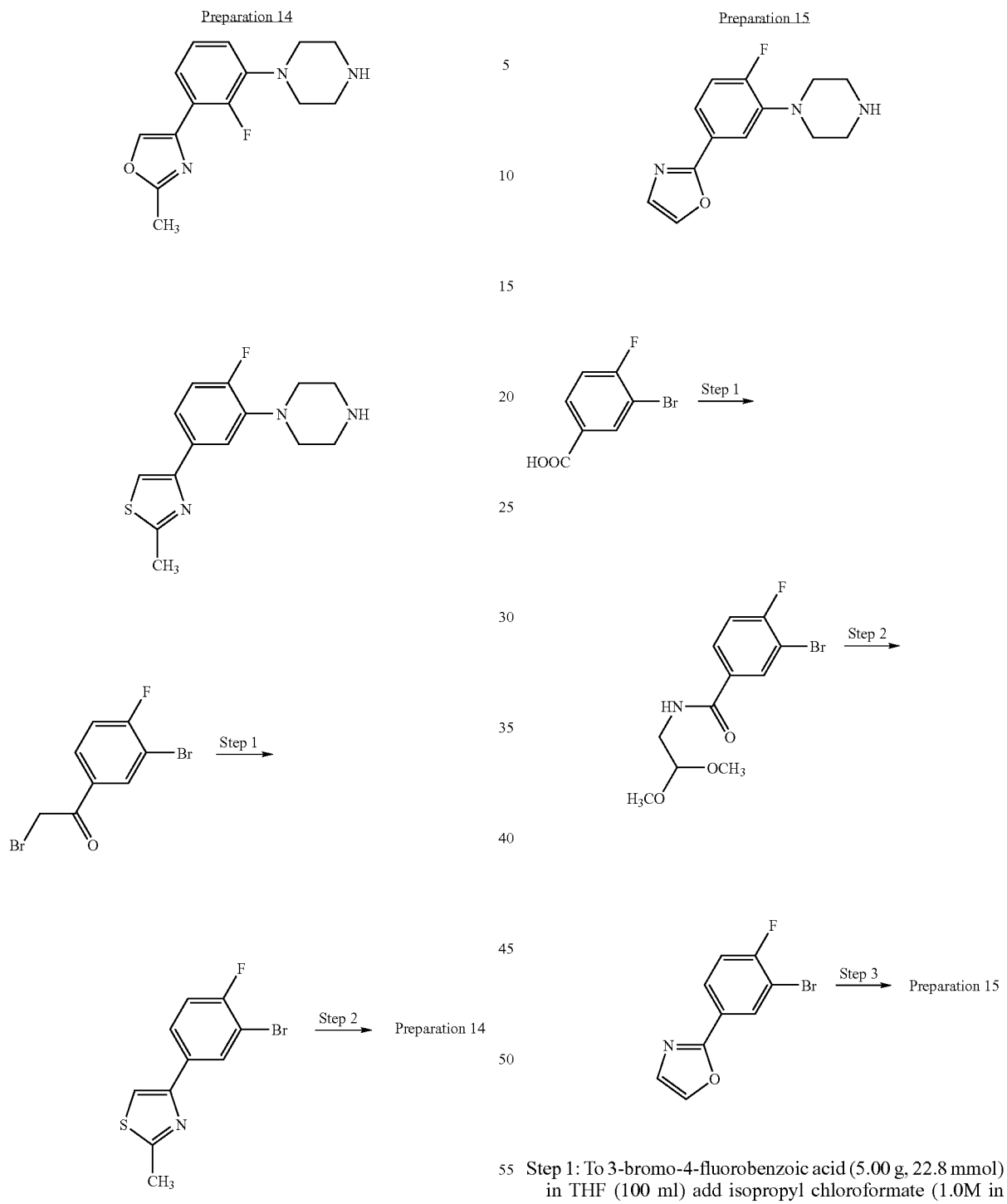

Step 1: Combine 2,3'-dibromo-4'-fluoroacetophenone (3.4 g, 11.5 mmol) and thioacetamide (1.00, 13.2 mmol) in dioxane and heat at 80° C. 2 h. Allow to cool, concentrate, and partition with ether and sat. NaHCO₃. Dry (MgSO₄), concentrate, and chromatograph on silica to obtain the thiazole as a yellow solid.

Step 2: React the product of Step 1 with piperazine according to Preparation 5, Step 2, to obtain the aryl-piperazine as a yellow oil.

Step 1: To 3-bromo-4-fluorobenzoic acid (5.00 g, 22.8 mmol) in THF (100 ml) add isopropyl chloroformate (1.0M in toluene, 22.8 ml, 22.8 mmol), followed by N-methylmorpholine (2.76 ml, 25.1 mmol). Stir 1 h and add aminoacetaldehyde dimethyl acetal (2.49 ml, 22.8 mmol). Stir 0.75 h and partition with ether and sat'd. NaHCO₃. Dry (MgSO₄), and concentrate to obtain the amide as a yellow oil.

Step 2: Combine the product of Step 1 (3.75 g, 12.3 mmol) with Eaton's reagent (10% P₂O₅ in CH₃SO₃H, 30 ml). Heat at 110° C. 18 h, allow to cool, pour onto ice, and stir 0.5 h. Collect the solid to obtain the oxazole as a gray powder.

Step 3: React the product of Step 2 with piperazine according to Preparation 5, Step 2, to obtain the aryl-piperazine as a yellow oil.

Preparation 16

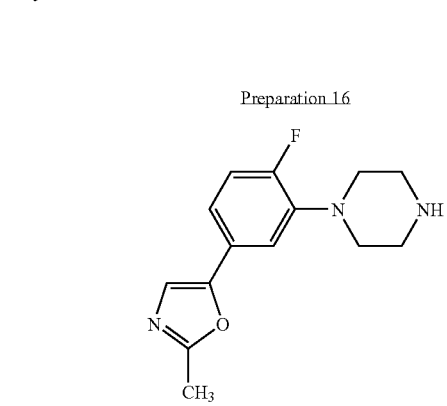

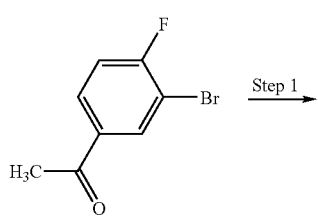

Step 1: To iodobenzene diacetate (5.34 g, 16.6 mmol) in CH$_3$CN (140 ml) add trifluoromethanesulfonic acid (5.5 ml, 62 mmol). Stir 30 min and add 3'-bromo-4'-fluoroacetophenone (3.00 g, 13.8 mmol). Heat at reflux 2 h, allow to cool, concentrate, and partition with EtOAc and satd. NaHCO$_3$. Dry (MgSO$_4$), concentrate, and chromatograph on silica to obtain the oxazole as a yellow oil.

Step 2: React the product of Step 1 with piperazine according to Preparation 5, Step 2, to obtain the aryl-piperazine as a yellow solid.

Preparation 17

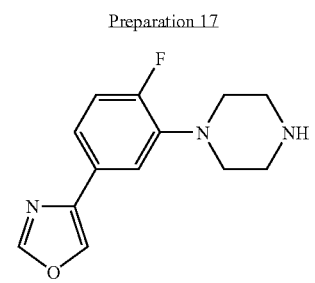

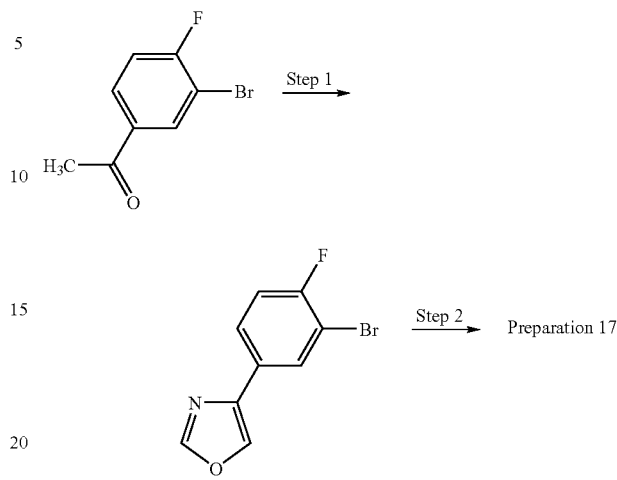

Step 1: To 3'-bromo-4'-fluoroacetophenone (3.50 g, 16.1 mmol) in formamide (10 ml) add bromine (0.83 ml, 16.1 mmol). Heat at 75° C. 2 h, then 135° C. 5 h. Allow to cool and partition with EtOAc and satd. NaHCO$_3$. Dry (MgSO$_4$), concentrate, and chromatograph on silica to obtain the oxazole as a yellow oil.

Step 2: React the product of Step 1 with piperazine according to Preparation 5, Step 2, to obtain the aryl-piperazine as a yellow oil.

Preparation 18

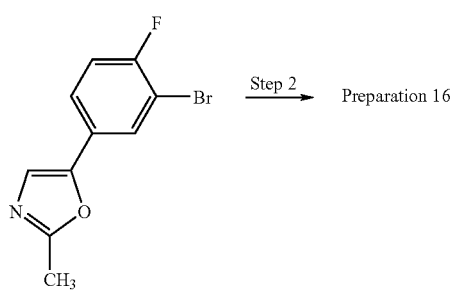

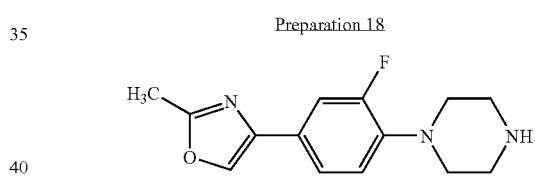

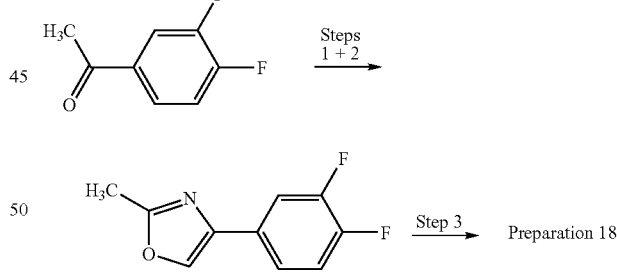

Steps 1 and 2: Convert 3',4'-difluoroacetophenone to the aryl-oxazole employing the method of Preparation 13, Steps 1 and 2.

Step 3: Combine the product of Step 2 (1.50 g, 7.7 mmol) with piperazine (4.0 g, 46 mmol) and K$_2$CO$_3$ (2.1 g, 15 mmol) in DMF (25 ml). Heat at 140° C. 48 h and allow to cool. Concentrate, and partition with EtOAc and brine. Extract with 1N HCl and basify the extract with NaOH to pH 13. Extract with CH$_2$Cl$_2$, dry (MgSO$_4$), and concentrate to obtain the title compound (contaminated with the regio-isomer) as a yellow oil.

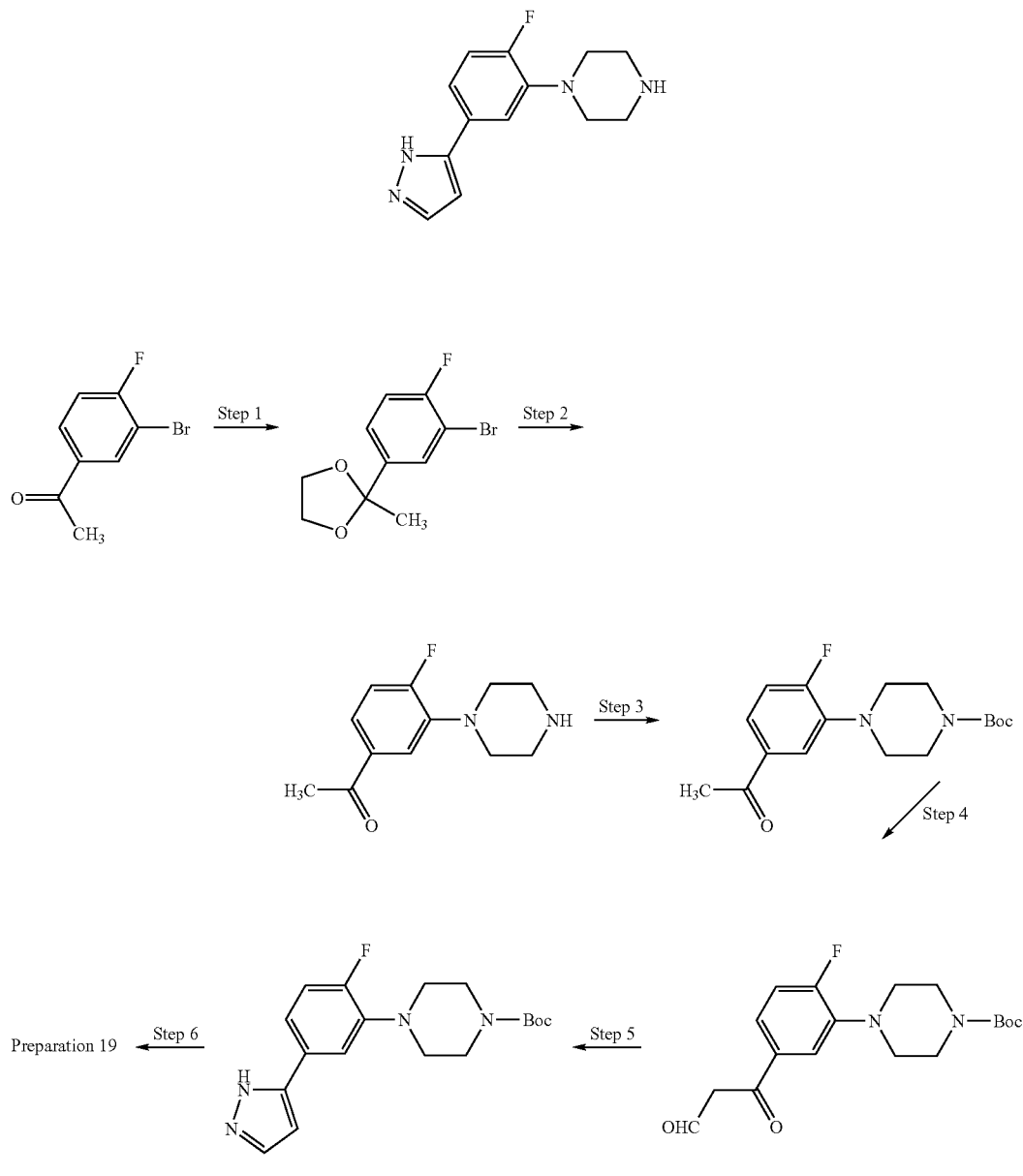

Step 1: Combine 3'-bromo-4'-fluuoroacetophenone (2.60 g, 12.0 mmol), ethylene gycol (3.3 ml, 59 mmol), and TsOH.H₂O (0.239, 1.2 mmol) in toluene (60 ml). Reflux with water separation (Dean-Stark) 4 h, allow to cool, and partition with hexane and 1N NaHCO₃. Wash with water, then brine, dry (MgSO₄), and concentrate to obtain the ketal as a colorless oil.

Step 2: Treat the product of Step 1 with piperazine according to the procedure of Preparation 5, Step 2, to obtain the aryl-piperazine as rosettes, mp 53-6° C.

Step 3: Convert the product of Step 2 to the Boc-derivative according to Preparation 7, Step 3.

Step 4: Heat KO-tBu (1.00 g, 8.9 mmol) in THF (40 ml) to 50° C. and add dropwise a mixture of the product of Step 3 (2.00 g, 6.2 mmol) and ethyl formate (1.5 ml, 19 mmol) in THF (20 ml). After 2 h, allow to cool, and partition between EtOAc and water. Wash the organic with 1N NaOH. Combine the aqueous and acidify to pH7-8 with NH₄Cl. Extract with EtOAc, dry (MgSO₄), and concentrate to obtain the crude formyl compound as a yellow solid.

Step 5: Combine the crude product of Step 4 (2.10 g, 6.0 mmol), hydrazine (0.28 ml, 9.0 mmol) and AcOH (0.69 ml, 12 mmol) in EtOH (30 ml). Heat at reflux 2 h and concentrate. Partition between EtOAc and 1N NaOH. Dry (MgSO₄), concentrate, and chromatograph on silica to obtain the pyrazole as a yellow solid.

Step 6: Deprotect according to Preparation 8, Step 7, and chromatograph on silica to obtain the piperazine as a yellow oil.

In similar fashion, treat the product of Step 3 with EtOAc (heat for 4 h) and continue as in Steps 5 and 6 to obtain Preparation 19-2 as a yellow solid.

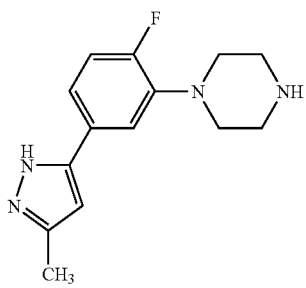

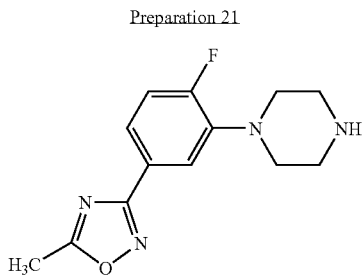

Preparation 21

Preparation 20

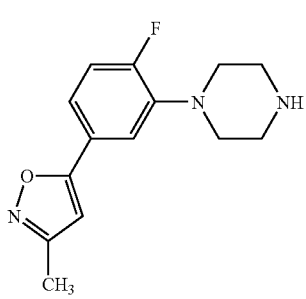

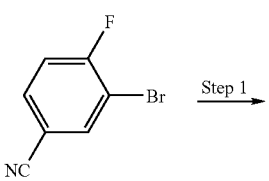 Step 1

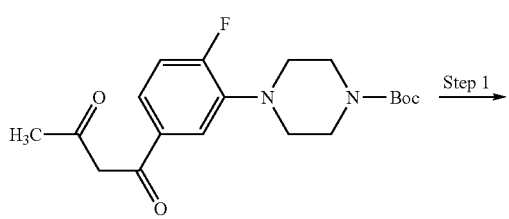 Step 1

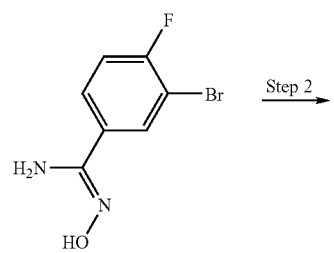 Step 2

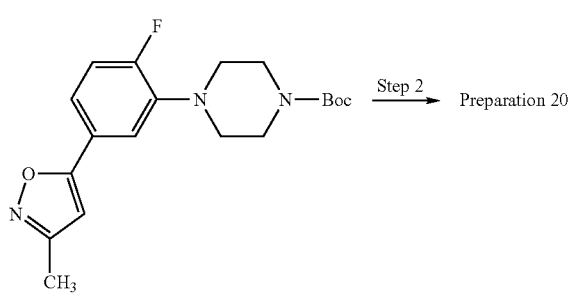 Step 2 Preparation 20

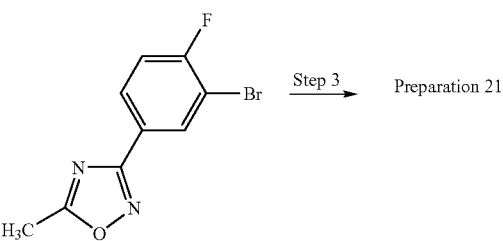 Step 3 Preparation 21

Step 1: Combine the diketone intermediate of Preparation 19-2 (1.50 g, 4.7 mmol) and hydroxylamine hydrochloride (0.66 g, 10.9 mmol) in EtOH (50 ml). Heat at reflux 5 h, allow to cool, concentrate, treat with 7N methanolic ammonia, concentrate, and chromatograph on silica to obtain the isoxazole as a yellow oil.

Step 2: Deprotect according to Preparation 8, Step 7, and chromatograph on silica to obtain the piperazine as a yellow oil.

Step 1: To 3-bromo-4-fluorobenzonitrile (10 g, 50 mmol) in EtOH (125 ml) add $Et_3N$ (16.1 ml, 115 mmol) and add hydroxylamine hydrochloride (7.64 g, 110 mmol). Heat to 75° C. and stir 24 h. Allow to cool, concentrate, and partition with EtOAc and water. Dry ($MgSO_4$) and concentrate to obtain the amide oxime as a white solid.

Step 2: To the product of Step 1 add acetic anhydride (20 ml). Heat at reflux for 2 h. Dilute with water and adjust pH to 8 with concentrated $NH_4OH$. Partition with $Et_2O$ and water. Dry ($MgSO_4$) and concentrate to obtain the 1,2,4-oxadiazole as a white solid.

Step 3: React the product of Step 2 with piperazine according to Preparation 5, Step 2, to obtain the aryl-piperazine as a yellow oil.

Similarly, convert 3-bromobenzonitrile to Preparation 21-2.

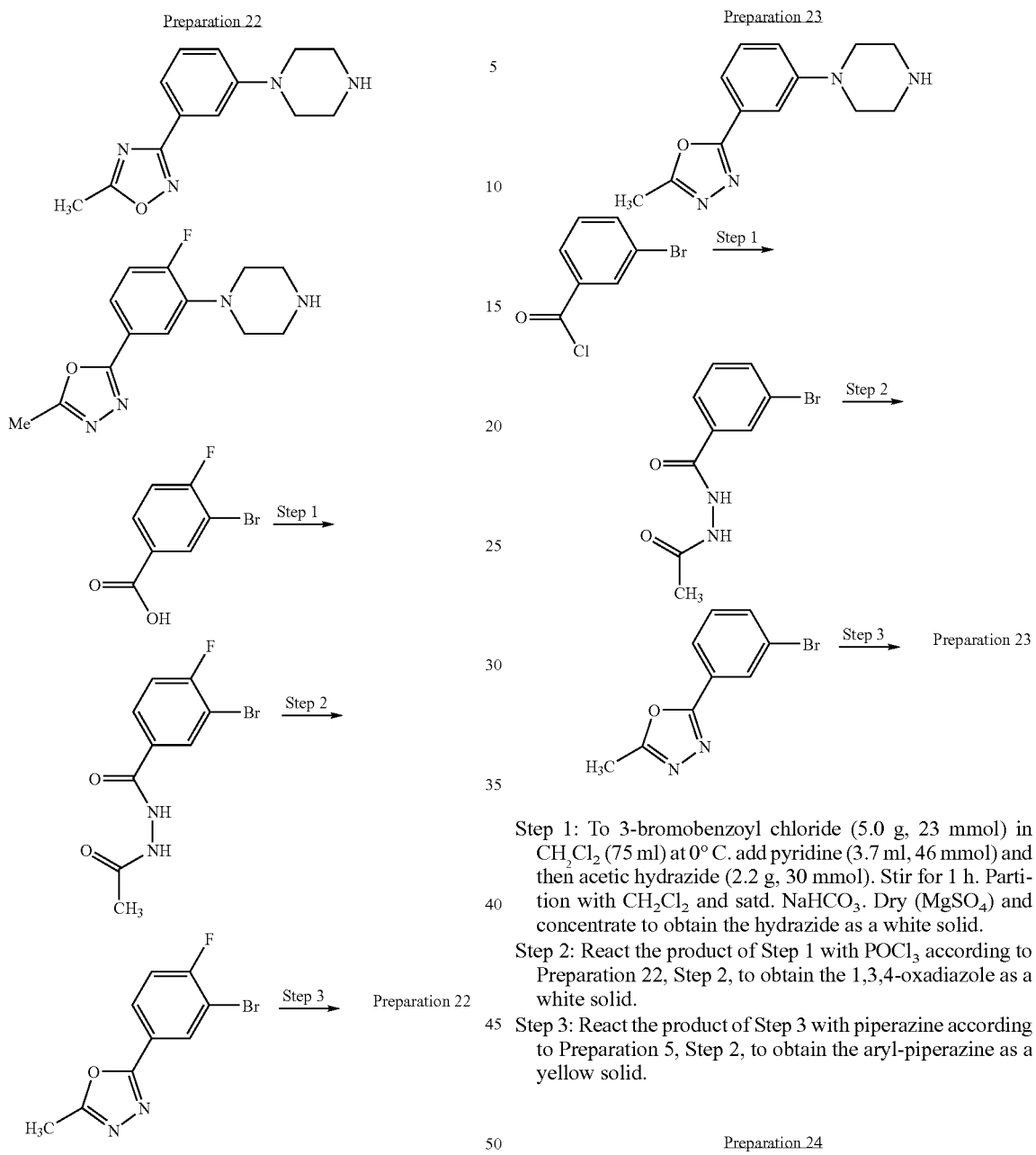

Step 1: To 3-bromo-4-fluorobenzoic acid (2.50 g, 110 mmol) in DMSO (35 ml) add acetic hydrazide (1.029, 13.7 mmol). Add EDCl (2.63 g, 13.7 mmol), then HOBt.H$_2$O (1.85 g, 13.7 mmol). Stir 24 h. Partition with EtOAc and water. Dry (MgSO$_4$) and concentrate to obtain the hydrazide as a yellow oil.

Step 2: To the product of Step 1 add POCl$_3$ (30 ml). Heat at reflux 17 h, allow to cool, concentrate, and partition with EtOAc and water. Dry (MgSO$_4$), concentrate, and recrystallize with CH$_2$Cl$_2$/hexanes to obtain the 1,3,4-oxadiazole as a tan solid.

Step 3: React the product of Step 2 with piperazine according to Preparation 5, Step 2, to obtain the aryl-piperazine as a yellow solid.

Step 1: To 3-bromobenzoyl chloride (5.0 g, 23 mmol) in CH$_2$Cl$_2$ (75 ml) at 0° C. add pyridine (3.7 ml, 46 mmol) and then acetic hydrazide (2.2 g, 30 mmol). Stir for 1 h. Partition with CH$_2$Cl$_2$ and satd. NaHCO$_3$. Dry (MgSO$_4$) and concentrate to obtain the hydrazide as a white solid.

Step 2: React the product of Step 1 with POCl$_3$ according to Preparation 22, Step 2, to obtain the 1,3,4-oxadiazole as a white solid.

Step 3: React the product of Step 3 with piperazine according to Preparation 5, Step 2, to obtain the aryl-piperazine as a yellow solid.

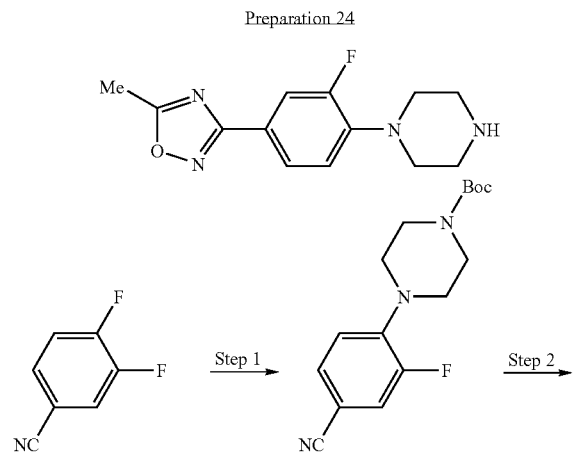

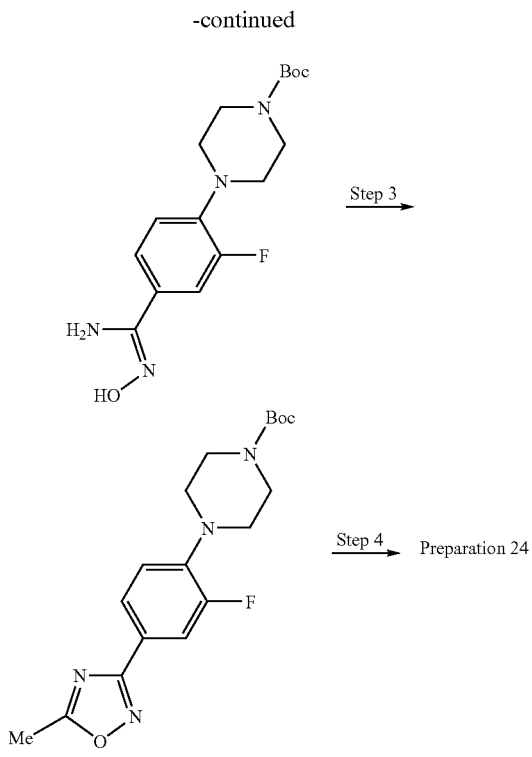

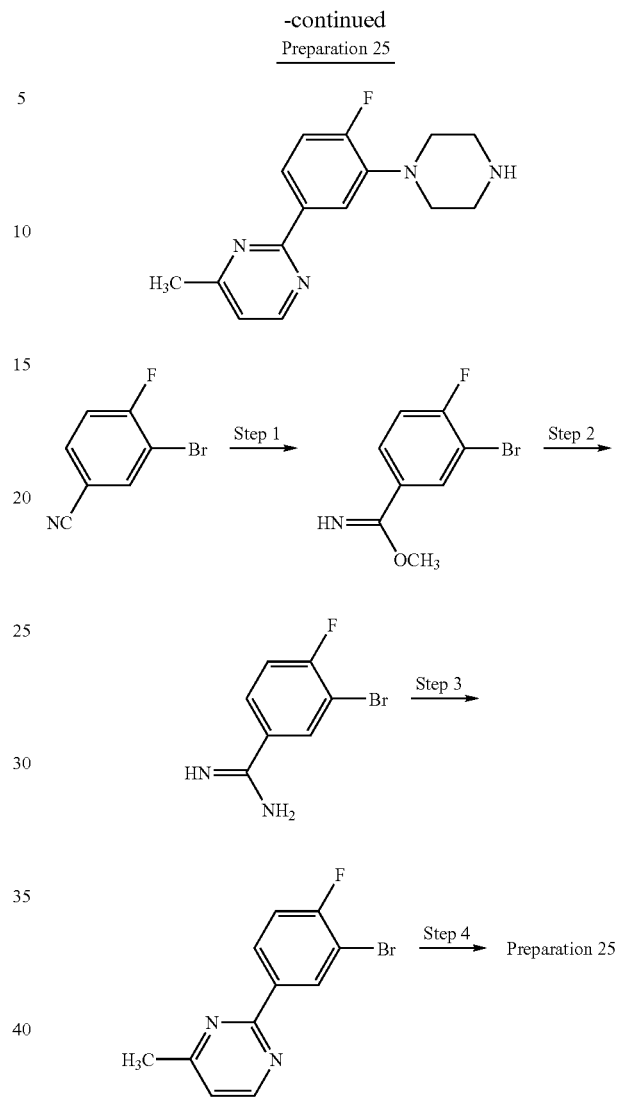

Step 1: To 3,4-difluorobenzonitrile (1.5 g, 11 mmol) in DMSO (25 ml) add tert-butyl piperazine-1-carboxylate (2.4 g, 13 mmol) and $K_2CO_3$ (2.2 g, 16 mmol). Heat to 110° C. and stir 24 h. Allow to cool and add water (300 ml). Filter, wash with water, and dry under vacuum to obtain the aryl-piperazine as a white solid.

Step 2: To the product of Step 1 (1.0 g, 3.3 mmol) in EtOH (12 ml) add Et3N (1.0 ml, 7.5 mmol) and then hydroxylamine hydrochloride (0.50 g, 7.2 mmol). Heat to 75° C. and stir 24 h. Allow to cool, concentrate, and partition with EtOAc and water. Dry ($MgSO_4$) and concentrate to obtain the amide oxime as a white solid.

Step 3: To the product of Step 2 add acetic anhydride (12 ml). Heat at reflux for 2 h. Dilute with water and adjust to pH 8 with $NH_4OH$. Partition with $Et_2O$ and water. Dry ($MgSO_4$) and concentrate to obtain the 1,2,4-oxadiazole as a yellow solid.

Step 4: To the product of Step 3 (0.649, 1.8 mmol) in $CH_2Cl_2$ (15 ml) add TFA (1.4 ml, 17 mmol). Stir 4 h, adjust pH to 11 with $NH_4OH$, and partition with $CH_2Cl_2$ and water. Dry ($MgSO_4$) and concentrate to obtain the 1,2,4-oxadiazole as a white solid.

In similar fashion, with propionic anhydride in place of acetic anhydride, produce Preparation 24-2, a brown solid.

Step 1: Combine 3-bromo-4-fluorobenzonitrile (10.0 g, 50 mmol) with $CH_3OH$ (4.8 g, 150 mmol) in ether (10 ml). Add 1.0M HCl in ether (110 ml, 110 mmol) and keep at 5° C. 12 days. Filter to obtain the imidate hydrochloride as a white solid.

Step 2: Dissolve the product of Step 1 (1.85 g, 6.9 mmol) in 7M $NH_3$/$CH_3OH$ (20 ml, 140 mmol). Keep at 5° C. 4 days and concentrate to give the amidine hydrochloride as a white solid.

Step 3: Combine the product of Step 2 (1.00 g, 3.9 mmol) and 4-methoxy-3-buten-2-one (0.48 g, 4.7 mmol) in $CH_3OH$ (10 ml). Heat to 50° C. and add NaOMe (0.43 g, 7.9 mmol) in $CH_3OH$ (5 ml). Heat 24 h, allow to cool, and concentrate. Dissolve in water, adjust to pH 7 with AcOH, and extract with $CH_2Cl_2$. Wash with brine, dry ($MgSO_4$), concentrate, and chromatograph on silica to obtain the pyrimidine as a white solid.

Step 4: React the product of Step 3 with piperazine according to Preparation 5, Step 2, to obtain the aryl-piperazine as a brown oil.

Preparation 26

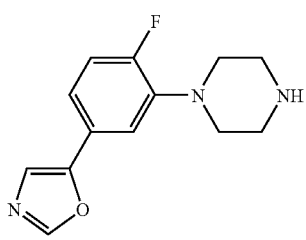

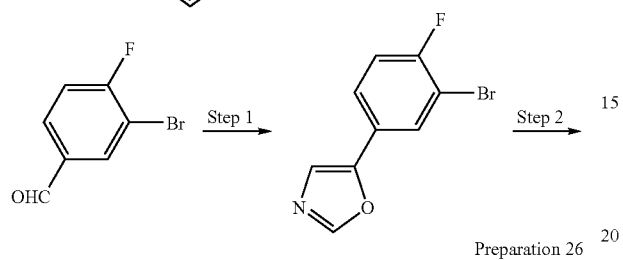

Step 1: To a solution of 3-bromo-4-fluorobenzaldehyde (4.90 g, 24 mmol) in MeOH (60 ml) add $K_2CO_3$ (6.66 g, 48 mmol) and toluenesulfonylmethyl isocyanate (5.42 g, 28 mmol). Heat at reflux 3 h, allow to cool, concentrate, and chromatograph on silica to obtain the oxazole as a yellow solid.

Step 2: React the product of Step 1 with piperazine according to Preparation 5, Step 2, to obtain the aryl-piperazine as a yellow oil.

Preparation 27

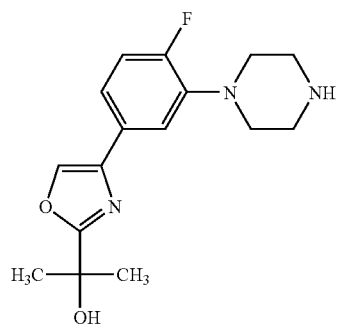

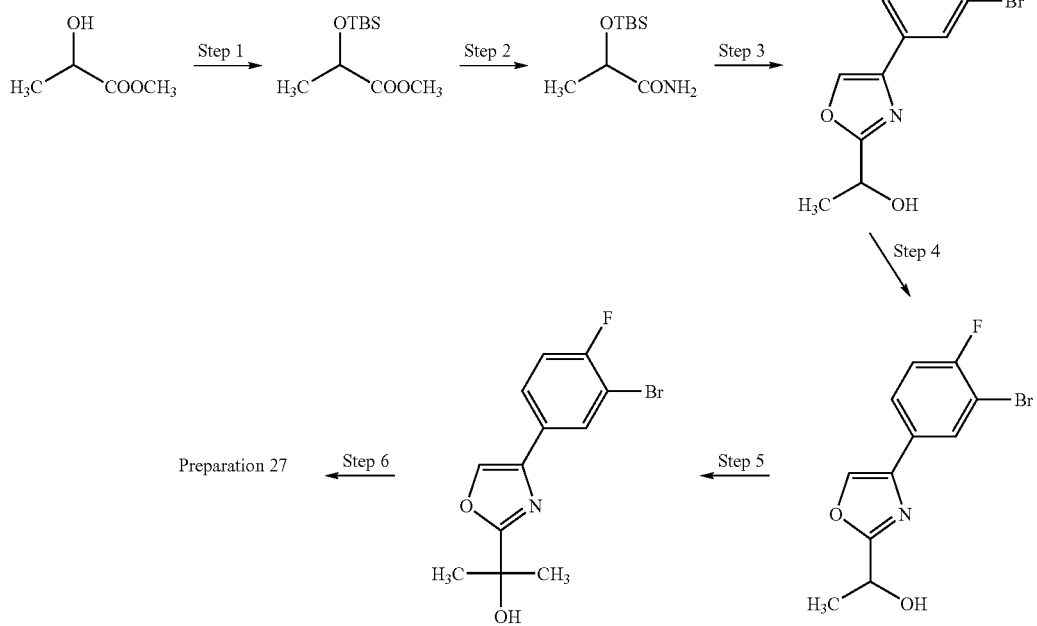

Step 1: To methyl (±)-lactate (8.0 g, 77 mmol) in THF (80 ml) add TBS-Cl (11.6 g, 77 mmol) and imidazole (6.3 g, 92 mmol). Stir 4 h and then heat at 50° C. 0.5 h. Allow to cool, add water and extract with ether. Dry (MgSO$_4$) and concentrate to obtain the crude product as a colorless oil.

Step 2: Combine the product of Step 1 with 7N NH$_3$/MeOH (40 ml) and heat in a sealed vessel at 50° C. 18 h. Allow to stand 3 days and concentrate to obtain the crude amide as a yellow oil.

Step 3: Combine the product of Step 2 (14.7 g, 72 mmol) with a solution of the product of Preparation 13, Step 1, from 6.0 g of the acetophenone. Heat at reflux 40 h, allow to cool, and add 7N NH$_3$/MeOH (20 ml). Concentrate and chromatograph on silica to obtain the oxazole as a yellow solid.

Step 4: Combine the product of Step 3 (1.8 g, 6.3 mmol) with pyridinium chlorochromate (6.89, 31 mmol) in CH$_2$Cl$_2$ (50 ml). Stir 18 h and add ether (100 ml). Filter through Celite, concentrate, and chromatograph on silica to obtain the ketone as a yellow solid.

Step 5: Cool a solution of the product of Step 4 (1.13 g, 4.0 mmol) in ether (25 ml) to 0° C. and add dropwise MeMgBr (3.0M in ether, 2.0 ml, 6.0 mmol). Stir 1 h and add 100 ml 8% NH$_4$Cl. Extract with ether and wash with NaHCO$_3$, then brine. Dry (MgSO$_4$) and concentrate to obtain the product as a white solid.

Step 6: React the product of Step 5 with piperazine according to Preparation 5, Step 2, to obtain the aryl-piperazine as a dark oil.

Preparation 28

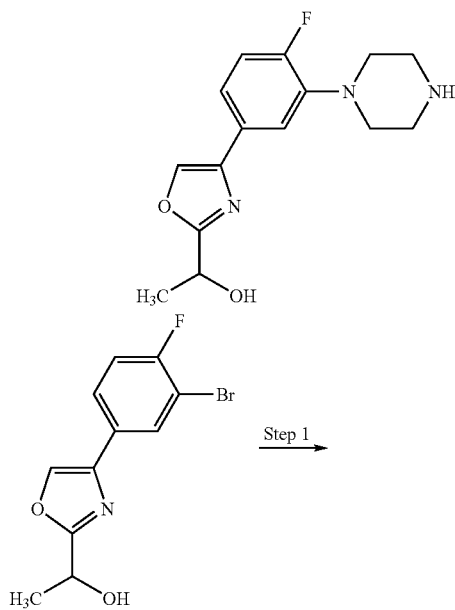

Step 1: Convert the product of Preparation 27, Step 3, to the TBS ether according to Preparation 27, Step 1.

Step 2: React the product of Step 1 with piperazine according to Preparation 5, Step 2, to obtain the aryl-piperazine as a yellow solid.

Preparation 29

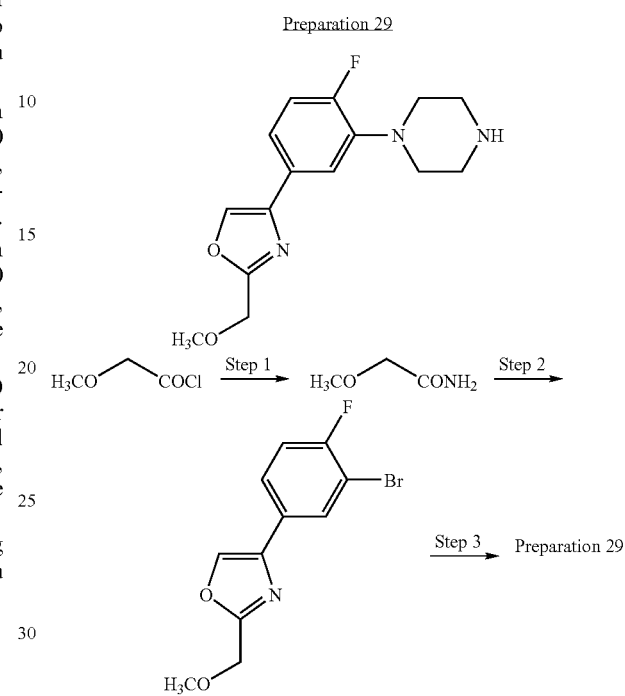

Step 1: To conc. NH$_4$OH (40 ml) cooled to 0° C. add dropwise methoxyacetyl chloride (10.0 g, 92 mmol). Stir 1 h, concentrate, treat with 9:1 ether/MeOH, filter, and concentrate to obtain the amide as a white solid.

Step 2: Treat the product of Step 1 with the sulfonyloxy-ketone as described in Preparation 27, Step 3. Concentrate and chromatograph on silica to obtain the oxazole as a yellow oil.

Step 3: React the product of Step 2 with piperazine according to Preparation 5, Step 2, to obtain the aryl-piperazine as a yellow oil.

Preparation 30

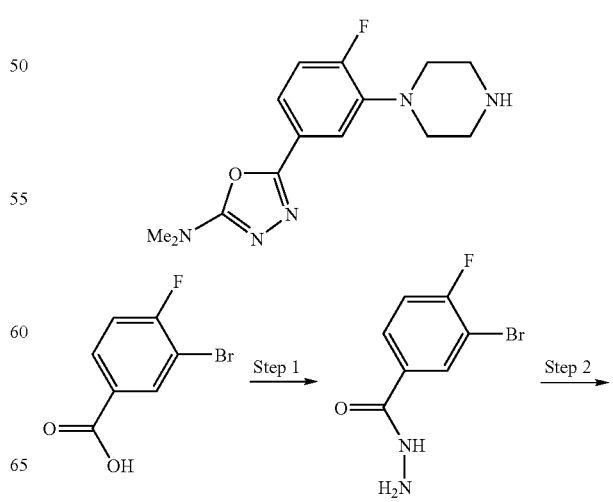

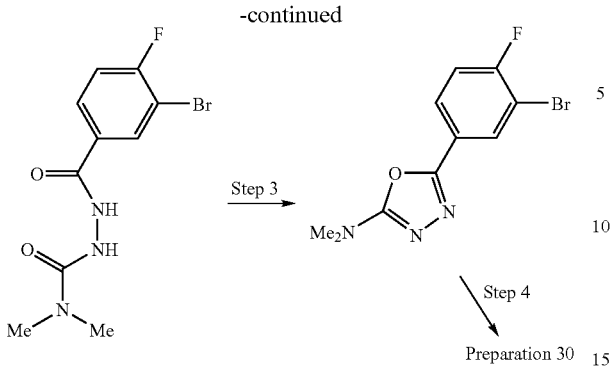

Step 1: To 3-bromo-4-fluorobenzoic acid (5.0 g, 22.8 mmol) in CH₃CN (120 ml) add EDCl (5.25 g, 27.4 mmol), and HOBt.H₂O (3.70 g, 27.4 mmol). Stir 2 h. Add the solution slowly over 15 min to a solution of hydrazine (1.43 ml, 45.7 mmol) in CH₃CN (20 ml) at 0° C. Allow to warm and stir 1 h. Partition with EtOAc and water. Dry (MgSO₄) and concentrate to obtain the hydrazide as a white solid.

Step 2: To the product of Step 1 (1.00 g, 4.29 mmol) in CH₂Cl₂ (40 ml) add pyridine (0.52 ml, 6.44 mmol). Cool to 0° C. and add dimethylcarbamyl chloride (0.44 ml, 4.72 mmol), then THF (20 ml). Stir 4 h, allow to warm, and stir 12 h. Partition with CH₂Cl₂ and water. Dry (MgSO₄) and concentrate to obtain the semicarbazide as a solid.

Step 3: To the product of Step 2 add POCl₃ (15 ml). Heat at reflux 5 h, allow to cool, concentrate, and partition with EtOAc and water. Dry (MgSO₄) and concentrate to obtain the 1,3,4-oxadiazole as an orange solid.

Step 4: React the product of Step 3 with piperazine according to Preparation 5, Step 2, to obtain the aryl-piperazine as a yellow oil.

Preparation 31

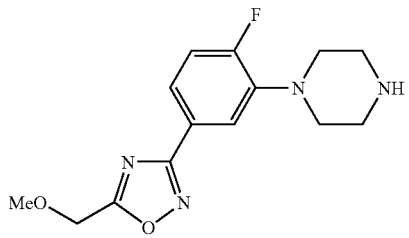

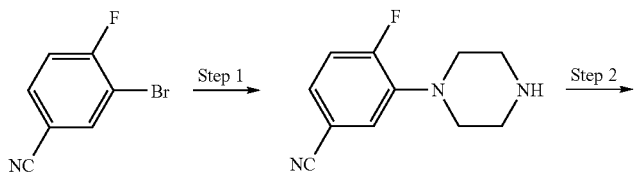

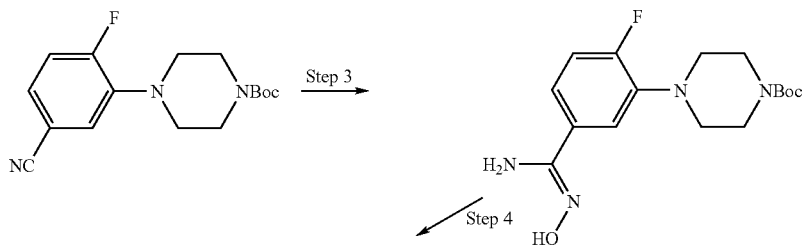

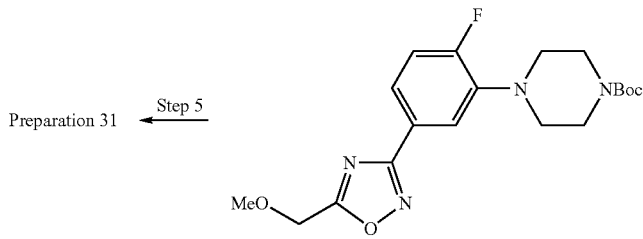

Step 1: React 3-bromo-4-fluorobenzonitrile with piperazine according to Preparation 5, Step 2, to obtain the piperazine as a brown oil.

Step 2: To the product of Step 1 (7.1 g, 35 mmol) in CH$_2$Cl$_2$ (175 ml) add Et$_3$N (9.7 ml, 69 mmol) and DMAP (1.1 g, 8.7 mmol), then Boc$_2$O (9.8 g, 45 mmol). Stir 24 h and partition with CH$_2$Cl$_2$ and water. Dry (MgSO$_4$) and concentrate to obtain the protected piperazine as a brown oil.

Step 3: To the product of Step 2 (10.09, 33 mmol) in EtOH (150 ml) add Et$_3$N (12 ml, 85 mmol) and hydroxylamine hydrochloride (5.7 g, 82 mmol). Heat at 75° C. 20 h and allow to cool. Add 1N HCl to adjust pH to 6, concentrate, and partition with EtOAc and water. Dry (MgSO$_4$) and concentrate to obtain the amide oxime as a yellow solid.

Step 4: To the product of Step 3 (0.79 g, 2.3 mmol) in pyridine (10 ml) add methoxyacetyl chloride (0.320 ml, 3.5 mmol). Heat at 110° C. 4 h and allow to cool. Partition with CH$_2$Cl$_2$ and water. Dry (MgSO$_4$) and concentrate to obtain the 1,2,4-oxadiazole as a brown oil.

Step 5: Deprotect the product of Step 4 according to Preparation 24, Step 4, and chromatograph on silica to obtain the title compound as a yellow oil.

Preparation 32

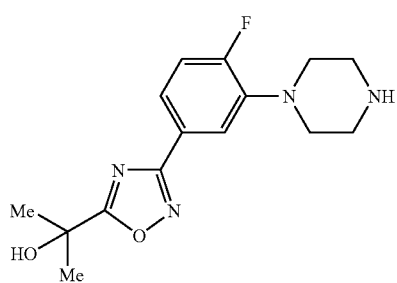

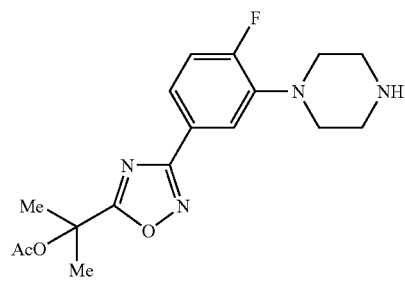

Preparation 32

Step 1: To the product of Preparation 31, Step 3, (2.0 g, 5.9 mmol) in pyridine (20 ml) add 1-chlorocarbonyl-1-methylethyl acetate (1.1 ml, 7.7 mmol). Heat at 110° C. 18 h and allow to cool. Partition with CH$_2$Cl$_2$ and water. Dry (MgSO$_4$) and concentrate to obtain the 1,2,4-oxadiazole as a yellow oil.

Step 2: Remove the Boc group according to Preparation 24, Step 4, and chromatograph on silica to obtain the piperazine as an oil.

Step 3: To the product of Step 2 (0.40 g, 1.2 mmol) in MeOH (6 ml) add 1N NaOH (5.5 ml, 5.5 mmol) and stir 0.5 h. Concentrate, partition with EtOAc and water, dry (MgSO$_4$), and concentrate to obtain the title compound as a white solid.

Preparation 33

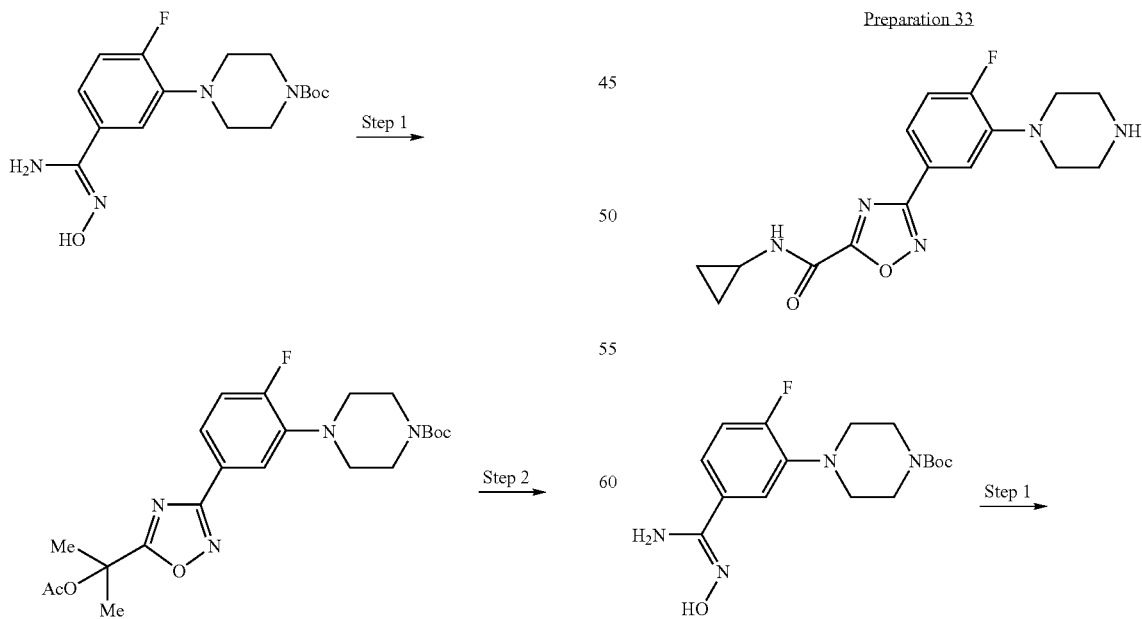

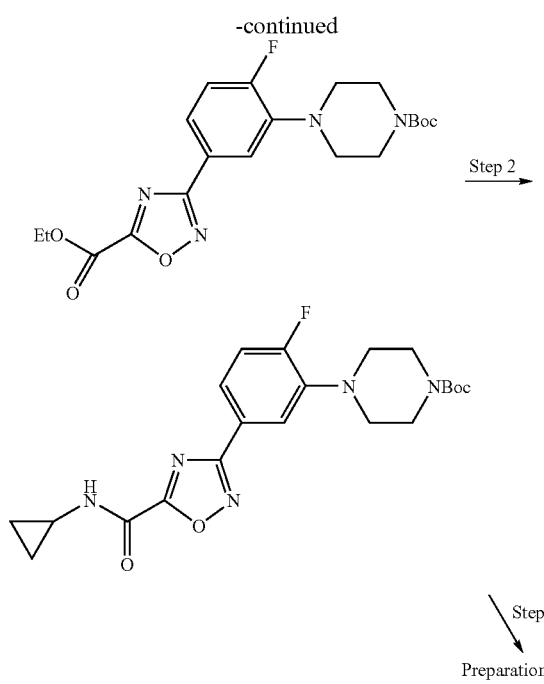

Step 3

Preparation 33

Step 1: To the product of Preparation 31, Step 3, (1.0 g, 3.0 mmol) in CH$_2$Cl$_2$ (15 ml) add pyridine (0.96 ml, 12 mmol), then ethyl oxalyl chloride (0.43 ml, 3.8 mmol). Stir 18 h and partition with CH$_2$Cl$_2$ and water. Dry (MgSO$_4$) and concentrate to obtain the 1,2,4-oxadiazole as a yellow oil.

Step 2: To the product of Step 1 (1.0 g, 2.4 mmol) in EtOH (12 ml) add cyclopropylamine (0.50 ml, 7.2 mmol). Heat at 80° C. 3 h, allow to cool, and concentrate to obtain the amide as a yellow oil.

Step 3: Deprotect the product of Step 2 according to Preparation 24, Step 4, and chromatograph on silica to obtain the piperazine as a yellow solid.

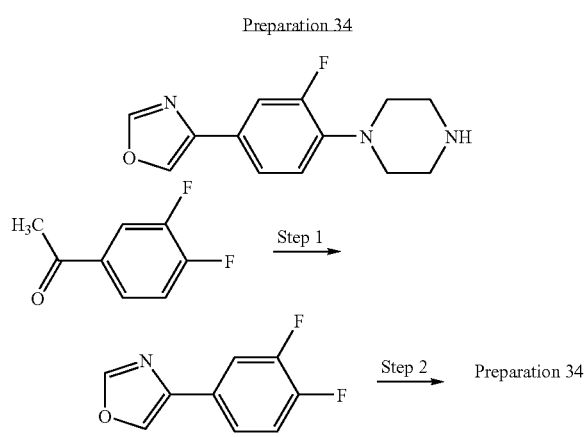

Preparation 34

Step 1: Combine 3',4'-difluoroacetophenone (5.0 g, 32 mmol) and Br$_2$ (1.65 ml, 32 mmol) in formamide (15 ml). Heat at 70° C. 3 h, then 130° C. 18 h, cool to 0° C., and add 1.0N NaOH (100 ml). Extract with ether, dry (MgSO$_4$) and concentrate. Chromatograph on silica to obtain the oxazole as a yellow solid.

Step 2: Combine the product of Step 1 (1.00 g, 5.52 mmol), piperazine (2.32 g, 28 mmo), and K$_2$CO$_3$ (1.52 g, 11 mmol) in DMF (20 ml). Heat at 140° C. 96 h, allow to cool, and concentrate. Chromatograph on silica to obtain the title piperazine as a yellow oil, as well as the regio-isomer.

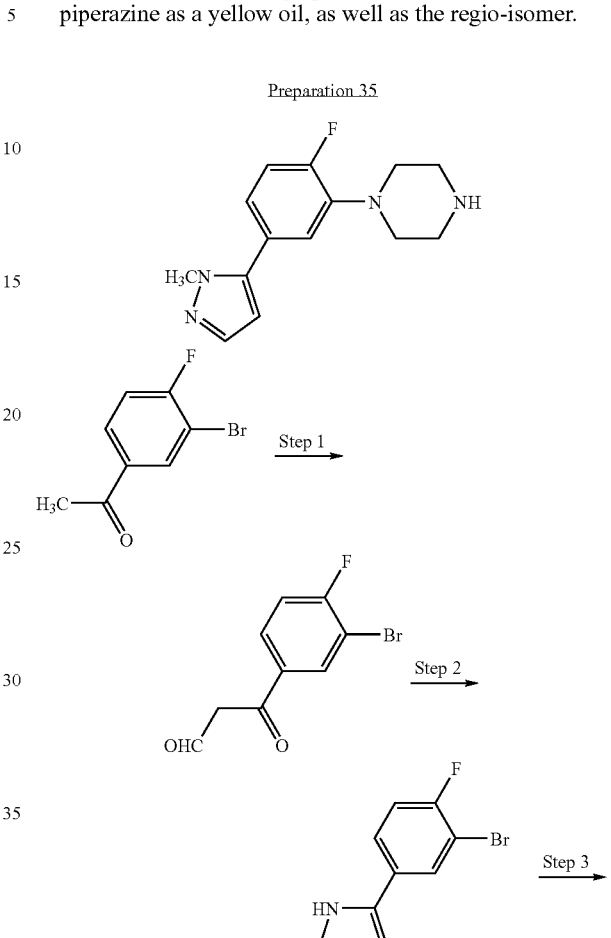

Preparation 35

Step 1: To 3'-bromo-4'-fluoroacetophenone (3.50 g, 16.1 mmol) in THF (100 ml) add KO-tBu (2.53 g, 16.1 mmol) and ethyl formate (3.9 ml, 48 mmol). Stir 18 h and add 1N NaOH (150 ml). Wash with ether and acidify with conc. HCl to pH1. Extract with ether, dry (MgSO$_4$), and concentrate to obtain the crude formyl compound.

Step 2: Combine the crude product of Step 1, hydrazine (1.01 ml, 32 mmol) and AcOH (1.85 ml, 32 mmol) in EtOH (80 ml). Heat at reflux 3 h, allow to cool and add 1N NaOH (50 ml). Extract with EtOAc, dry (MgSO$_4$), and concentrate to obtain the pyrazole as a yellow solid.

Step 3: Dissolve the product of Step 2 (1.72 g, 7.1 mmol) in DMF (20 ml). Cool to 0° C. and add NaH (60% in oil, 0.40 g, 10.0 mmol) and CH$_3$I (0.49 ml, 7.9 mmol). Stir 3 h at 0° C., concentrate, and chromatograph on silica to obtain the pyrazole as a yellow oil.

Step 4: React the product of Step 3 with piperazine according to Preparation 5, Step 2, to obtain the aryl-piperazine as a yellow oil.

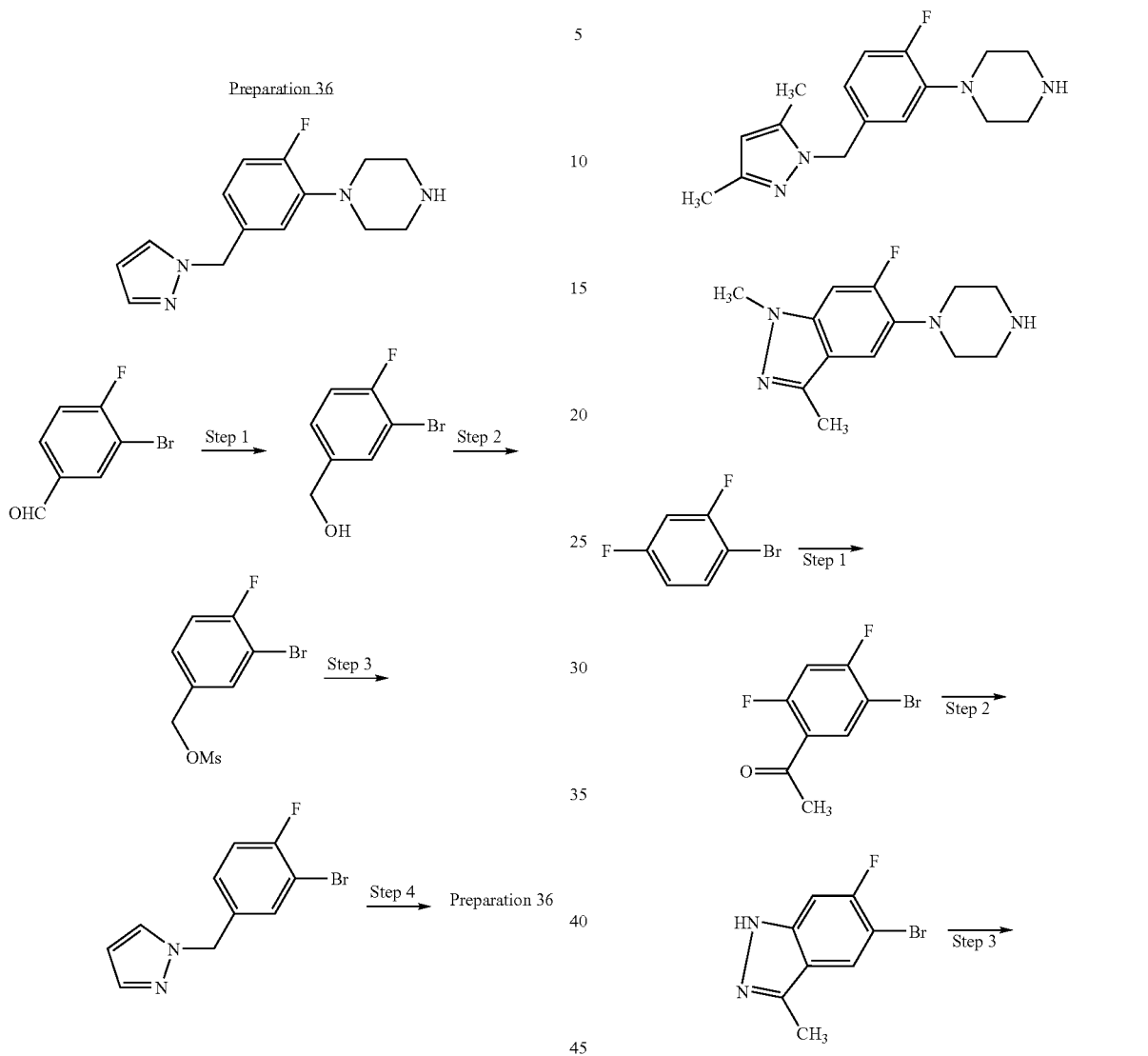

Step 1: To 3-bromo-4-fluorobenzaldehyde (3.50 g, 17.2 mmol) in THF (25 ml) add NaBH₄ (0.65 g, 17 mmol). Stir 2 h and add water (5 ml), then 1N NaOH (50 ml). Extract with ether, dry (MgSO₄), and concentrate to obtain the alcohol as a yellow oil.

Step 2: To the product of Step 1 (3.609, 17.6 mmol), in CH₂Cl₂ (40 ml) at 0° C. add CH₃SO₂Cl (1.56 ml, 20 mmol) and Et₃N (2.93 ml, 21 mmol). Stir 2 h and add satd. NaHCO₃. Extract with CH₂Cl₂, dry (MgSO₄), and concentrate to obtain the crude mesylate as a yellow oil.

Step 3: To pyrazole (1.80 g, 26 mmol) in DMF (25 ml) at 0° C. add NaH (60% in oil, 1.05 g, 26 mmol). Stir 0.25 h and add the crude product of Step 2. Stir 3 h, add water (100 ml), and extract with ether. Dry (MgSO₄) and concentrate to obtain the pyrazole as a yellow oil.

Step 4: React the product of Step 3 with piperazine according to Preparation 5, Step 2, to obtain the aryl-piperazine as a yellow oil.

In similar fashion, substituting 3,5-dimethylpyrazole in Step 3, produce Preparation 36-2, a yellow oil:

Step 1: Combine 2,4-difluorobromobenzene (6.00 g, 31 mmol) with AlCl₃ (10.4 g, 34.3 mmol) and heat to 60° C. Add dropwise acetyl chloride (3.66 g, 47 mmol). Heat at 95° C. 1.5 h, cool to 0° C., and add ice-water, then conc. HCl (15 ml). Extract with ether, dry (MgSO₄), concentrate and chromatograph on silica to obtain the ketone as a brown oil.

Step 2: Combine the product of Step 1 (1.32 g, 5.6 mmol) and hydrazine (0.19 ml, 5.9 mmol) in ethyene glycol (3.0 ml).

Heat at 160° C. 20 h, allow to cool, dilute with water, and extract with EtOAc. Dry (MgSO₄), concentrate and chromatograph on silica to obtain the indazole as a yellow solid.

Step 3: Cool the product of Step 2 (0.699, 3.0 mmol) in THF (15 ml) to 0° C. and add NaO-t-Bu (0.35 g, 3.6 mmol), then CH₃I (0.19 ml, 3.6 mmol). Stir 2 h and allow to warm over 8 h. Concentrate and chromatograph on silica to obtain the alkylation product as a yellow solid.

Step 4: React the product of Step 3 with piperazine according to Preparation 5, Step 2, to obtain the aryl-piperazine as a yellow solid.

Step 2: React the product of Step 2 with piperazine according to Preparation 5, Step 2, to obtain the protected aryl-piperazine as a yellow oil.

Step 3: Combine the product of Step 2 (1.83 g, 5.0 mmol) and TBAF (1.0M in THF, 7.5 ml, 7.5 mmol) in THF (20 ml). Heat at reflux 18 h, allow to cool, and stir 96 h. Concentrate and chromatograph on silica to obtain, in addition to starting material, the title compound as a yellow oil.

Preparation 38

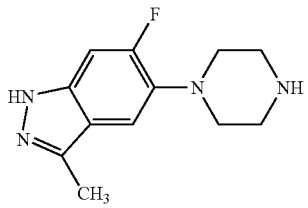

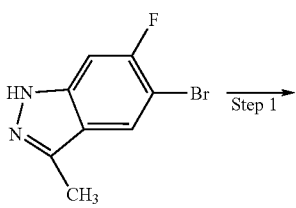

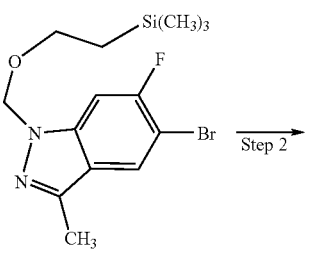

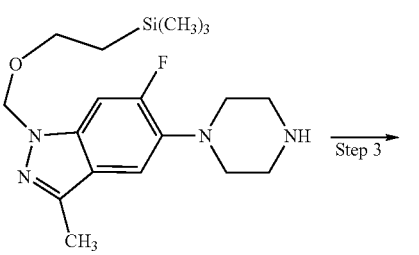

Preparation 39

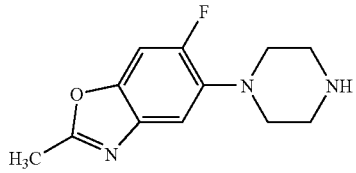

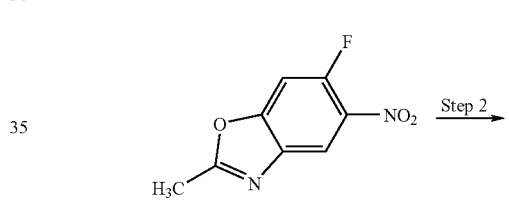

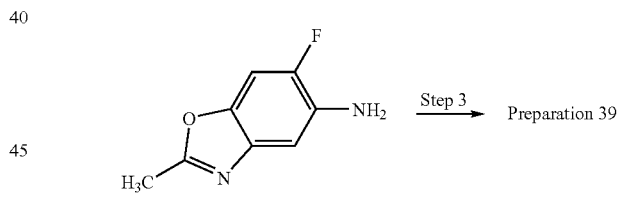

Step 1: Cool the product of Preparation 37, Step 2 (2.50 g, 10.9 mmol) in DMF (30 ml) to 0° C. and add NaH (60% in oil, 0.62 g, 15 mmol). Stir 10 min and add 2-(trimethylsilyl)ethoxymethyl chloride (2.32 ml, 13 mmol). Stir 2 h and allow to warm over 1 h. Add water (100 ml), extract with ether, dry (MgSO₄), concentrate and chromatograph on silica to obtain the alkylation product as a yellow oil.

Step 1: Add 6-fluoro-2-methylbenzoxazole (1.0 g) to conc. $H_2SO_4$ (15.5 ml) at 0° C. Stir 0.5 h and add dropwise conc. $HNO_3$ (0.5 ml). Stir 2 h, pour onto ice, and stir 0.5 h. Filter and wash with satd. $NaHCO_3$, then water, and dry to obtain the nitro compound as a yellow solid.

Step 2: Hydrogenate the product of Step 1 with 10% Pd—C in EtOAc at 1 atm for 5 h. Filter through celite, concentrate, and purify by PLC to give the aniline.

Step 3: To a solution of the product of Step 2 (0.30 g) in chlorobenzene (7 ml), add bis-(2-chloroethyl)amine hydrochloride (0.360 g). Heat at 130° C. 24 h, allow to cool, concentrate, and chromatograph on silica, eluting with $NH_3/MeOH/CH_2Cl_2$ to give the title compound.

In similar fashion, starting with 5-fluoro-2-methylbenzoxazole, produce Preparation 39-2.

Preparation 40

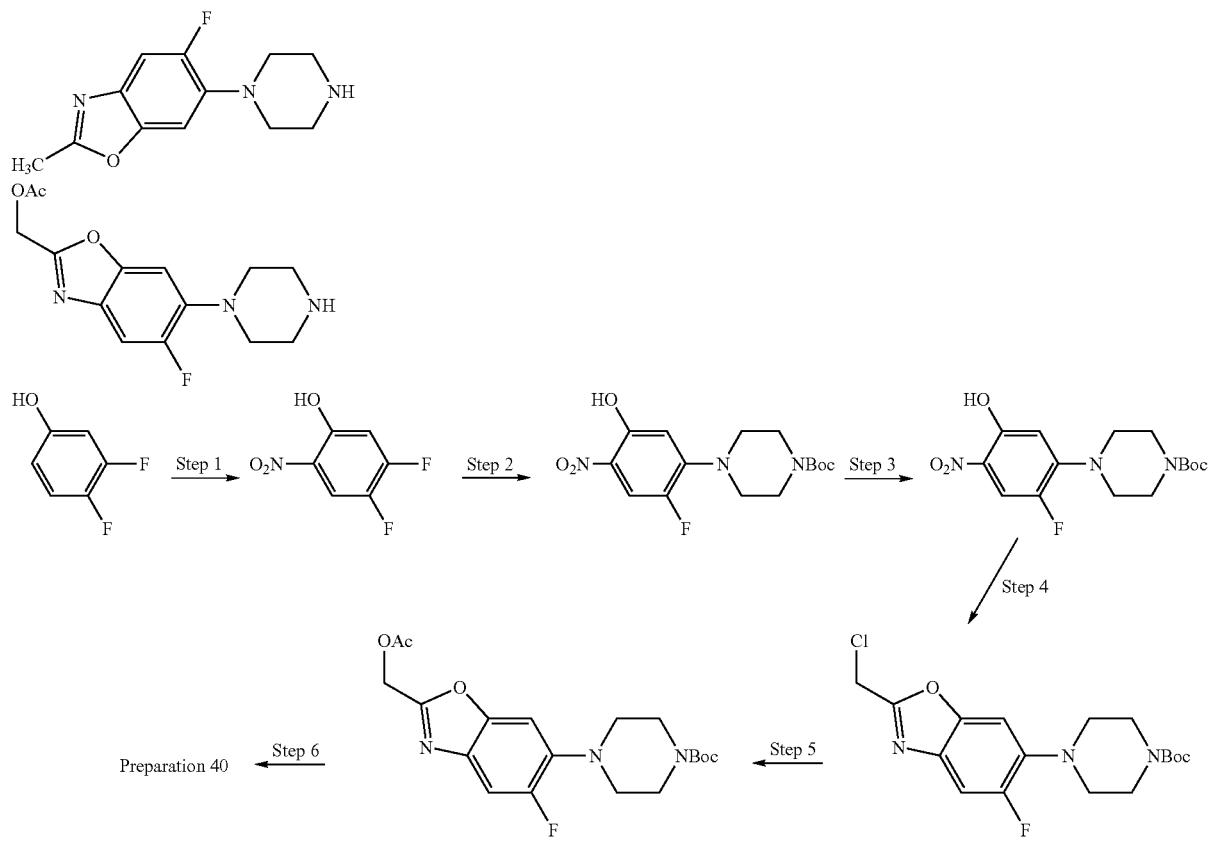

Step 1: To 3,4-difluorophenol (10.0 g, 76.9 mmol) in AcOH (45 ml) add dropwise (45 min) a solution of fuming HNO$_3$ (4.4 ml) in AcOH (18 ml), keeping the temperature below 50° C. Stir at RT 2 h and pour slowly onto ice with constant shaking. Filter the solid, dissolve in CH$_2$Cl$_2$, wash with sat. NaHCO$_3$ solution, then brine, dry (MgSO$_4$), and concentrate to give the nitrophenol as a yellow solid.

Step 2: Heat a mixture of the product of Step 1 (8.0 g, 46 mmol), N-Boc-piperazine (14.0 g, 75.2 mmol), and K$_2$CO$_3$ (10.5 g, 76.1 mmol) in toluene (100 ml) at 110° C. 16 h. Allow to cool, wash with water, dry (MgSO$_4$), concentrate, and chromatograph on silica to obtain the piperazine.

Step 3: Hydrogenate a mixture of the product of Step 2 (5.0 g, 15 mmol) and 5% Pd—C (0.5 g) in 1:1 THF—MeOH (300 ml) at 1 atm for 3 h, filter through celite, and concentrate to obtain the crude aniline.

Step 4: Combine the crude material from Step 3 and 2-chloro-1,1,1-trimethoxyethane (5.85 ml, 43.4 mmol) in degassed EtOH (150 ml). Heat at 65° C. 16 h, allow to cool, concentrate, and chromatograph on silica to obtain the chloride.

Step 5: To a solution of the product of Step 4 (0.88 g, 2.38 mmol) in DMF (35 ml) add CsOAc (0.91 g, 4.76 mmol). Stir 16 h and partition with EtOAc and water. Dry (MgSO$_4$) and concentrate to obtain the crude acetate.

Step 6: To the product of Step 5 (0.10 g, 0.25 mmol) in CH$_2$Cl$_2$ (10 ml) add TFA (3 ml). Stir 3 h, concentrate, and partition with CH$_2$Cl$_2$ and 1N NaOH. Wash the aqueous layer with CH$_2$Cl$_2$, combine extracts, dry (K$_2$CO$_3$), and concentrate. Employ the resulting oil without further purification.

$^1$H NMR (400 MHz, CDCl$_3$): δ 7.31 (d, 1H, J=11.7 Hz), 7.05 (d, 1H, J=6.6 Hz), 5.21 (s, 2H), 3.01 (s, 8H), 2.11 (s, 3H)

In similar fashion, employing triethyl orthopropionate in place of 2-chloro-1,1,1-trimethoxyethane in Step 4, produce the analogous 2-ethylbenzoxazole. Treat this analogously to Step 6 to obtain Preparation 40-2.

Preparation 41

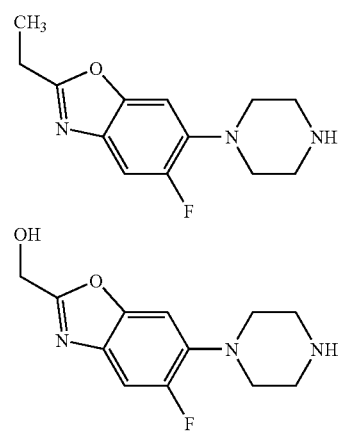

-continued

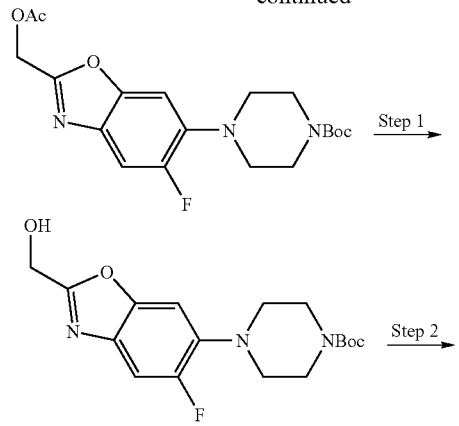

Step 1: To the product of Preparation 40, Step 5 (0.75 g, 1.9 mmol) in MeOH (20 ml) add K₂CO₃ (0.07 g, 0.5 mmol). Stir 3 h, concentrate, treat with CH₂Cl₂, wash with brine, dry (MgSO₄), and concentrate to obtain the crude alcohol. $^1$H NMR (400 MHz, CD₃OD): δ 7.35 (d, 1H, J=12 Hz), 7.30 (d, 1H, J=8 Hz), 4.84 (s, 2H), 3.64 (m, 4H), 3.05 (m, 4H), 1.44 (s, 9H)

Step 2: Following the procedure of Preparation 40, Step 6, convert the crude product of Step 1 to the title compound, a brown oil.

Preparation 42

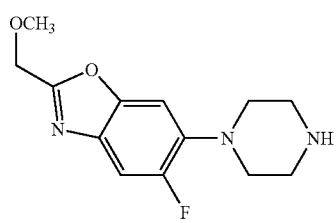

-continued

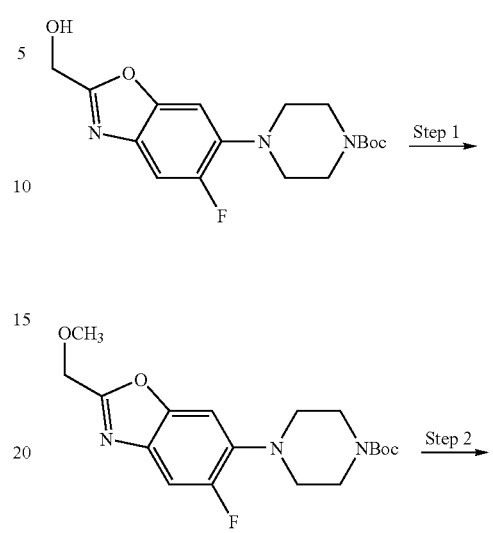

Step 1: To the product of Preparation 41, Step 1 (0.20 g, 0.57 mmol) in DMF (15 ml) add NaH (60% in oil, 0.07 g, 1.7 mmol), followed by CH₃I (0.14 ml, 1.7 mmol). Stir 16 h, quench with satd. NH₄Cl, and extract with EtOAc. Wash with brine, dry (K₂CO₃), concentrate and purify by PLC to obtain the methyl ether. $^1$H NMR (400 MHz, CDCl₃): δ 7.34 (d, 1H, J=11.6 Hz), 7.05 (d, 1H, J=7.3 Hz), 4.61 (s, 2H), 3.57 (m, 4H), 3.45 (s, 3H), 2.99 (m, 4H), 1.43 (s, 9H)

Step 2: Following the procedure of Preparation 40, Step 6, convert the product of Step 1 to the title compound, a brown oil.

Similarly, employing ethyl iodide in Step 1, produce Preparation 42-2.

Preparation 43

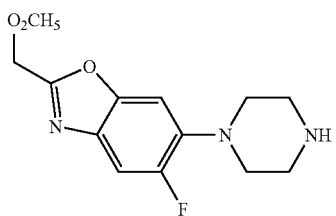

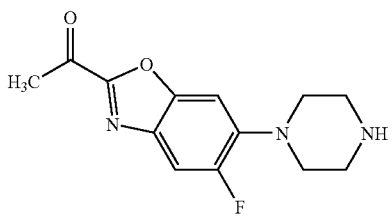

-continued

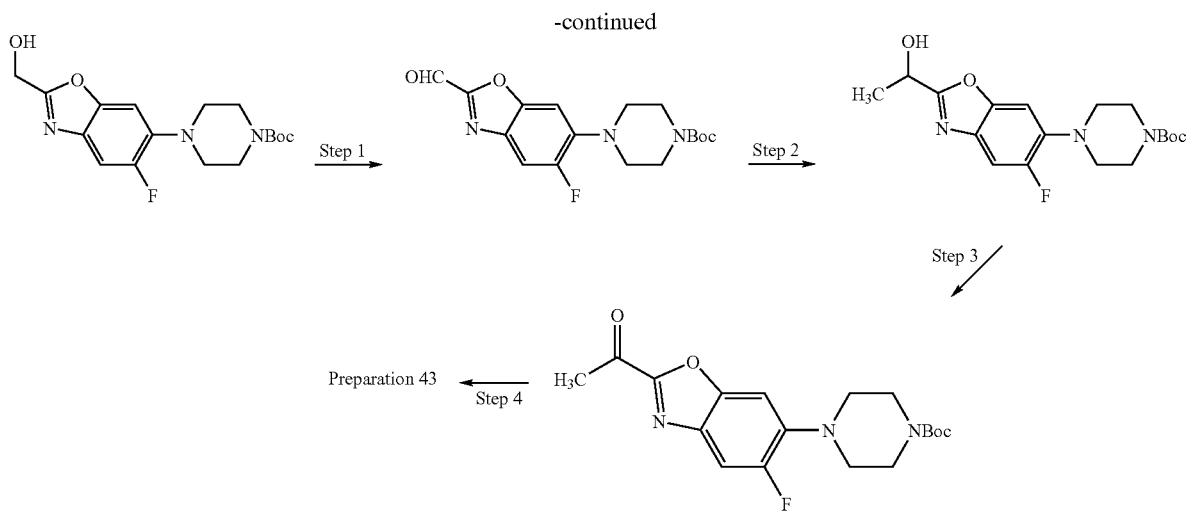

Step 1: To the product of Preparation 41, Step 1 (0.50 g, 1.4 mmol) in CH$_2$Cl$_2$ (35 ml) add Dess-Martin periodinane (1.2 g, 2.8 mmol). Stir 2 h, add 1N NaHCO$_3$, then sodium sulfite solution, and extract with CH$_2$Cl$_2$. Dry (MgSO$_4$), concentrate, and chromatograph on silica to obtain the aldehyde as a yellow solid.

Step 2: To an ice-cold solution of the product of Step 1 (2.0 g, 5.7 mmol) in THF (60 ml) add 3M CH$_3$MgBr in THF (3.8 ml, 11.4 mmol). Allow to warm, stir 6 h, quench with satd. NH$_4$Cl, and extract with EtOAc. Dry (MgSO$_4$), concentrate, and chromatograph on silica to obtain the alcohol as a yellow solid.

Step 3: Treat the product of Step 2 with Dess-Martin periodinane according to Step 1 to obtain the ketone.

Step 4: Following the procedure of Preparation 40, Step 6, convert the product of Step 3 to the title compound, a brown oil.

Preparation 44

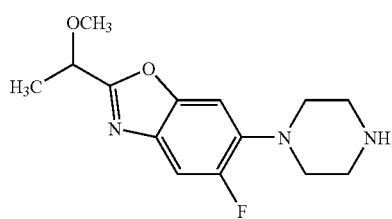

Methylate the product of Preparation 43, Step 2, according to the procedure of Preparation 42, Step 1, and treat the resulting material with TFA according to Preparation 40, Step 6, to obtain the title compound, a brown oil.

Preparation 45

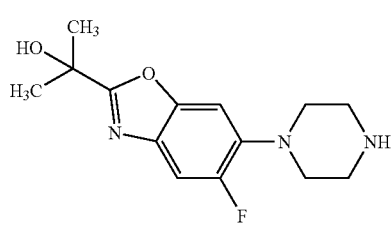

Treat the product of Preparation 43, Step 3, with CH$_3$MgBr according to the procedure of Step 2, and treat the resulting material with TFA according to Preparation 40, Step 6, to obtain the title compound, a brown oil.

Preparation 46

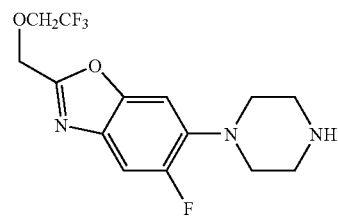

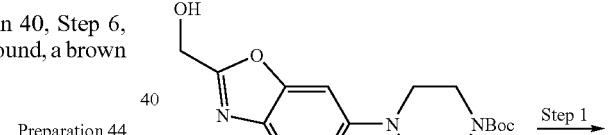

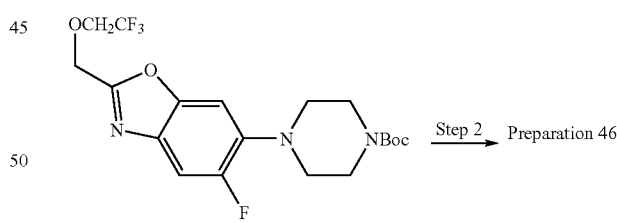

Step 1: To the product of Preparation 41, Step 1 (0.20 g, 0.57 mmol) in benzene (12 ml) add 1,1'-(azodicarbonyl)-dipiperidine (0.29 g, 1.14 mmol), followed by BU$_3$P (0.29 ml, 1.14 mmol). After 10 min add trifluoroethanol (0.41 ml, 5.7 mmol). Stir 1 h and wash with water, then brine. Dry (K$_2$CO$_3$), concentrate, and chromatograph on silica to obtain the ether. $^1$H NMR (400 MHz, CDCl$_3$): δ 7.39 (d, 1H, J=11.2 Hz), 7.28 (d, 1H, J=6.4 Hz), 4.84 (s, 2H), 3.99 (q, 2H, J=8 Hz), 3.64 (m, 4H), 3.06 (m, 4H), 1.45 (s, 9H)

Step 2: Following the procedure of Preparation 40, Step 6, convert the product of Step 1 to the title compound, a brown oil.

Preparation 47

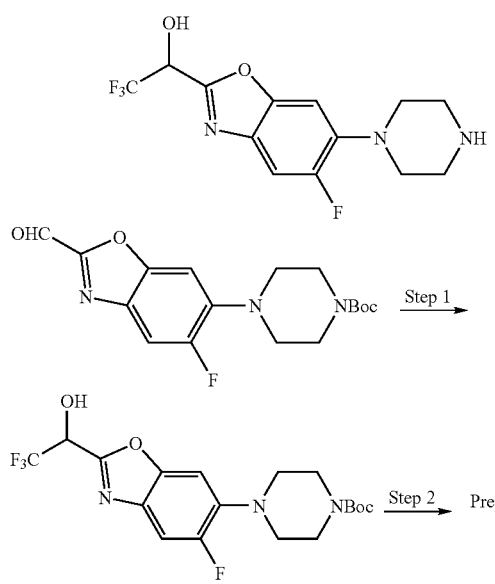

Step 1: To an ice-cold solution the product of Preparation 43, Step 1 (0.3 g, 0.86 mmol) in THF (20 ml) add trifluoromethyltrimethylsilane (0.13 ml, 0.86 mmol), followed by 2 drops of TBAF. Stir at 0° C. 2 h, add 0.5N HCl (20 ml), allow to warm, and stir 2 h. Extract with EtOAc, wash with brine, dry (MgSO$_4$), concentrate, and purify by PLC to obtain the alcohol as a yellow solid.

Step 2: Following the procedure of Preparation 40, Step 6, convert the product of Step 1 to the title compound, a brown oil. $^1$H NMR (400 MHz, CDCl$_3$): δ 7.37 (d, 1H, J=11.7 Hz), 7.01 (d, 1H, J=7.3 Hz), 5.23 (q, 1H, J=8 Hz), 3.42 (m, 4H), 3.02 (m, 4H).

Preparation 48

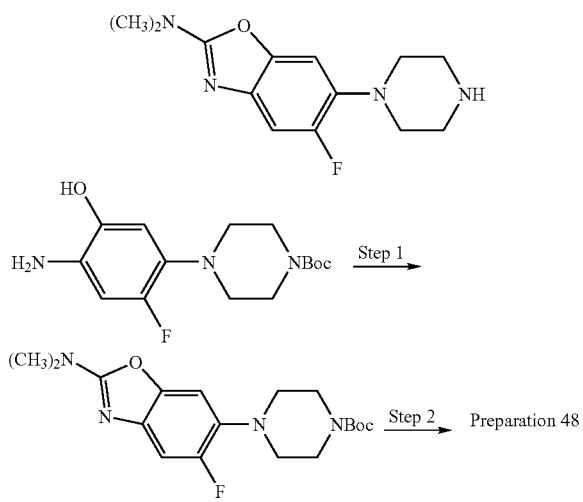

Step 1: To the product of Preparation 40, Step 3 (from the product of Step 2, 0.55 g, 1.61 mmol) in CHCl$_3$ (7 ml) at −10° C. add Et$_3$N (0.45 ml, 3.2 mmol), followed by tetramethyl-formamidinium chloride (0.24 g, 1.77 mmol) in CHCl$_3$ (3 ml). Allow to warm, stir 0.5 h, and wash with water, then brine. Dry (K$_2$CO$_3$), concentrate, and purify by PLC to obtain the benzoxazole. $^1$H NMR (400 MHz, CDCl$_3$): δ 6.93 (d, 1H, J=11.7 Hz), 6.86 (d, 1H, J=7.3 Hz), 3.55 (m, 4H), 3.11 (s, 6H), 2.90 (m, 4H), 1.43 (s, 9H).

Step 2: Following the procedure of Preparation 40, Step 6, convert the product of Step 1 to the title compound, a brown oil.

Preparation 49

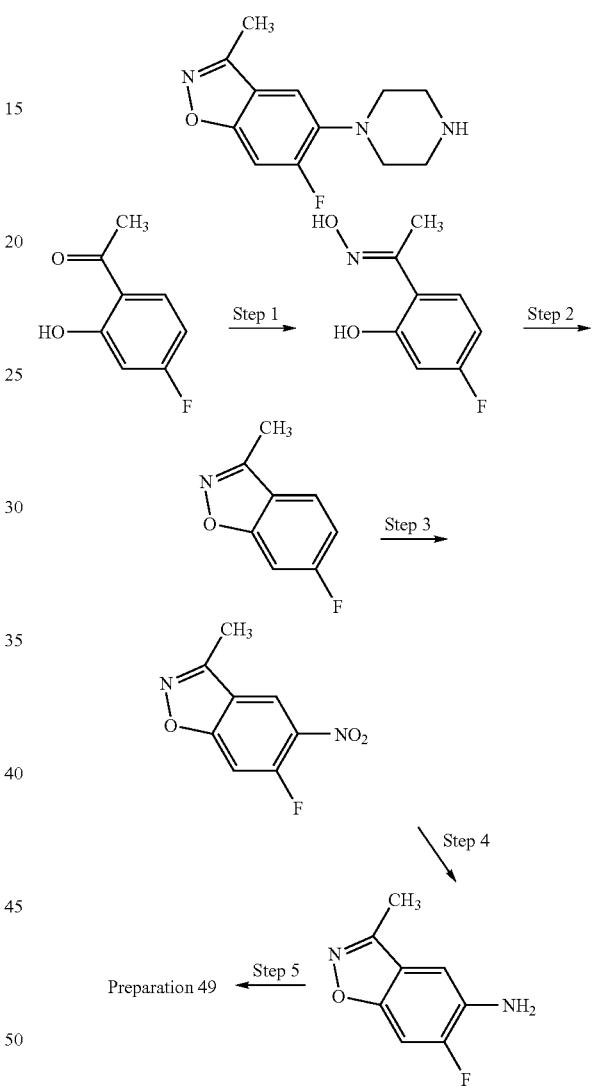

Step 1: Heat at reflux 2 h a mixture of 4-fluoro-2-hydroxyacetophenone (50 g, 324 mmol), hydroxylamine hydrochloride (45 g, 648 mmol), and sodium acetate (40 g, 488 mmol) in MeOH (1.0 l). Allow to cool, pour onto ice and stir 0.5 h. Filter, dissolve the solid in CH$_2$Cl$_2$, dry (MgSO$_4$), and concentrate to obtain the oxime as a white solid.

Step 2: To the product of Step 1 (50 g, 296 mmol) in DMF (800 ml) add sodium acetate (55 g, 670 mmol) followed by acetic anhydride (65 ml, 689 mmol). Heat at reflux for 4 h, allow to cool, pour into water and extract with ether. Wash with brine, dry (Na$_2$SO$_4$), and concentrate to obtain the benzisoxazole as a brown solid.

Step 3: To an ice-cold solution of the product of Step 2 (42 g, 278 mmol) in conc. H₂SO₄ (300 ml) add dropwise conc. HNO₃ (70 ml). Allow to warm and stir 3 h. Pour onto ice and filter. Dissolve the solid in CH₂Cl₂ and wash with sat. NaHCO₃ solution, then brine. Dry (MgSO₄), filter, and concentrate to obtain the nitro-compound as a yellow solid.

to a white solid and add chlorobenzene (80 ml) and bis(chloroethyl)amine (3.8 g, 21 mmol). Heat at reflux 48 h, allow to cool and remove most of the solvent. Treat with hot MeOH (200 ml) and filter the black residue. Concentrate and chromatograph on silica to obtain the title compound, MS: m/e 236 [M+1].

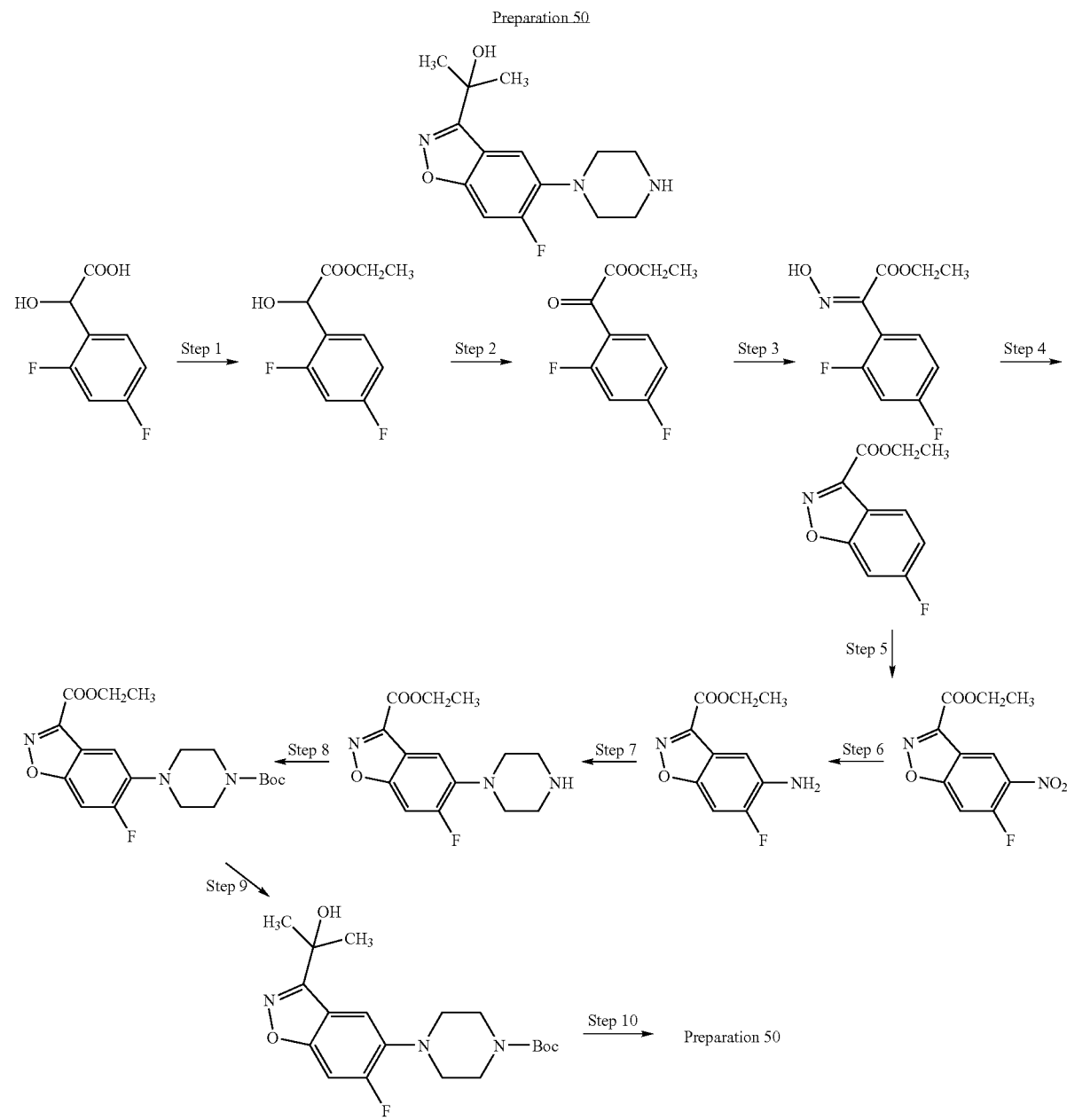

Step 4: To the product of Step 3 (47 g, 240 mmol) in AcOH (800 ml) at 40° C. add a solution of SnCl₂.2H₂O (150 g, 665 mmol) in conc. HCl (400 ml). Heat at reflux 2 h, allow to cool, and adjust to pH 5-6 with aqueous NaOH. Add ether with stirring, decant the liquid, separate, and wash with brine. Dry (Na₂SO₄), concentrate and chromatograph on silica to obtain the aniline as a yellow solid.

Step 5: To the product of Step 4 (3.2 g, 19 mmol) in CH₂Cl₂ (100 ml) add 2M HCl/ether (9.6 ml, 19 mmol). Concentrate Step 1: Heat at reflux for 24 h a solution of 2,4-difluoromandelic acid (9.79 g, 52.1 mmol) and H₂SO₄ (0.3 ml) in EtOH (20 ml). Allow to cool, concentrate, and partition with EtOAc and water. Dry (MgSO₄) and concentrate to obtain the ester. ¹H NMR (400 MHz, CDCl₃): δ 7.32 (m, 1H), 6.82 (m, 2H), 5.33 (s, 1H), 4.20 (m, 2H), 3.49 (brs, 1H), 1.18 (s, 3H)

Step 2: Add acetic anhydride (5.5 ml) dropwise over 1 h to a solution of the product of Step 1 (10.4 g, 48.1 mmol) in DMSO (22 ml) at 90° C. After 2.5 h allow to cool and add water (8 ml) and EtOAc (50 ml). Wash with brine, dry (MgSO$_4$), and concentrate to obtain the crude ketone as a yellow oil.

Step 3: Combine the crude product of Step 2, hydroxylamine hydrochloride (3.81 g, 55.0 mmol) and NaOAc (4.54 g, 55.0 mmol) in EtOH (15 ml). Stir 4 h, filter, and concentrate the filtrate. Partition between water and CH$_2$Cl$_2$, dry (MgSO$_4$), and concentrate to give the oxime, MS: m/e 230 [M+1$^+$].

Step 4: Heat at 100° C. for 1.25 h a mixture of the product of Step 3 (10.7 g, 46.7 mmol) and K$_2$CO$_3$ (6.59, 46.7 mmol) in DMSO (30 ml). Quench with water, filter, wash with water, and dry to obtain the benzisoxazole.

Step 5: To a solution of the product of Step 4 (6.33 g, 30.3 mmol) in conc. H$_2$SO$_4$ (42 ml) at 0° C. add dropwise HNO$_3$ (10 ml). After 1 h, pour onto ice, extract with CH$_2$Cl$_2$, dry (MgSO$_4$), concentrate, and chromatograph on silica to obtain the nitro-compound. $^1$H NMR (400 MHz, CDCl$_3$): δ 8.85 (d, 1H, J=6.6 Hz), 7.55 (d, 1H, J=9.5 Hz), 4.56 (q, 2H, J=7.3 Hz), 1.47 (t, 3H, J=7.3 Hz)

Step 6: Heat to 40° C. a solution of the product of Step 5 (5.62 g, 22.0 mmol) in 1:1 EtOAc-EtOH (120 ml) and add SnCl$_2$.2H$_2$O (14.1 g, 62.3 mmol) in conc. HCl (67 ml). Heat at reflux 2 h, allow to cool, concentrate, and neutralize with 2N NaOH. Extract with CH$_2$Cl$_2$, dry (MgSO$_4$), concentrate, and chromatograph on silica to obtain the aniline.

Step 7: Heat at 140° C. a mixture of the product of Step 6 (1.85 g, 8.26 mmol), and bis(chloroethyl) amine hydrochloride (1.54 g, 8.58 mmol) in chlorobenzene (18 ml). After 21 h, allow to cool, concentrate, and partition with water and CH$_2$Cl$_2$. Basify the aqueous with 2N NaOH to pH8 and extract with CH$_2$Cl$_2$. Dry (MgSO$_4$), concentrate, and purify by PLC to obtain the piperazine, MS: m/e 294 [M+1$^+$].

Step 8: To the product of Step 7 (0.242g, 0.83 mmol) in CH$_2$Cl$_2$ (13 ml) at 0° C. add Et$_3$N (0.35 ml, 2.49 mmol). After 10 min, add dropwise a solution of Boc$_2$O (0.270 g, 1.24 mmol) in CH$_2$Cl$_2$ (2.4 ml). Allow to warm, stir 15 h, concentrate, and purify by PLC to obtain the Boc-derivative. $^1$H NMR (400 MHz, CDCl$_3$): δ 7.63 (d, 1H, J=8.1 Hz), 7.34 (d, 1H, J=10.2 Hz), 4.50 (q, 2H, J=5.1 Hz), 3.61 (t, 4H, J=5.1 Hz), 3.03 (t, 4H, J=5.1 Hz) 1.45 (m, 12H).

Step 9: To the product of Step 8 (0.290 g, 0.74 mmol) in ether (40 ml) at 0° C. add dropwise over 5 min CH$_3$MgBr (3.0M in ether, 0.54 ml, 1.70 mmol). After 1 h, partition with water and CH$_2$Cl$_2$. Dry (MgSO$_4$), concentrate, and purify by PLC to obtain the alcohol. Re-subject a mixture of recovered ester and ketone to CH$_3$MgBr to obtain additional alcohol.

Step 10: Following the procedure of Preparation 40, Step 6, convert the product of Step 9 to the title compound. $^1$H NMR (400 MHz, CDCl$_3$): δ 9.97 (br s, 1H), 7.62 (br s, 1H), 7.52 (m, 1H), 7.24 (m, 1H), 3.91 (m, 2H), 3.41 (m, 4H), 3.15 (m, 2H)1.73 (s, 6H); MS: m/e 280 [M+1$^+$]

EXAMPLE 1

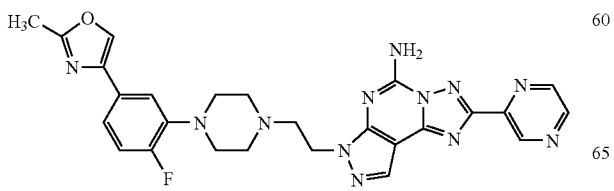

-continued

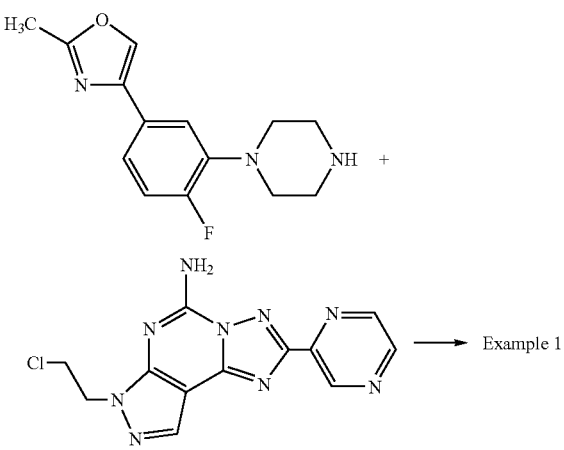

→ Example 1

Combine the product of Preparation 2-3 (0.058 g, 0.18 mmol), the product of Preparation 13 (0.078 g, 0.30 mmol), DIPEA (0.037 ml, 0.21 mmol), and KI (0.028 g, 0.17 mmol) in DMF (2.0 ml). Heat at 110° C. 48 h. Concentrate and purify by PLC to obtain the title compound as a yellow solid, MS: m/e 541 (M+1).

In similar fashion, employing the aryl-piperazines from the Preparations section together with Preparation 2-3, prepare the following compounds:

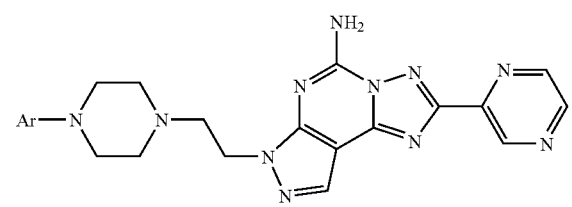

| Example | Ar | MS, m/e |
|---|---|---|
| 1-2 | 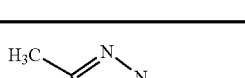 | 542 |
| 1-3 | 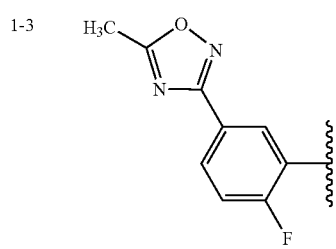 | 542 |

-continued
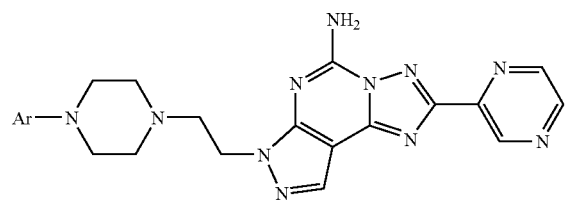
| Example | Ar | MS, m/e |
|---|---|---|
| 1-4 | 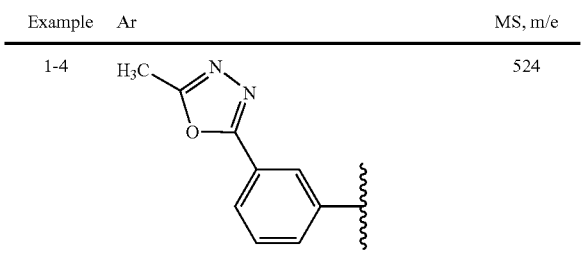 | 524 |
| 1-5 | 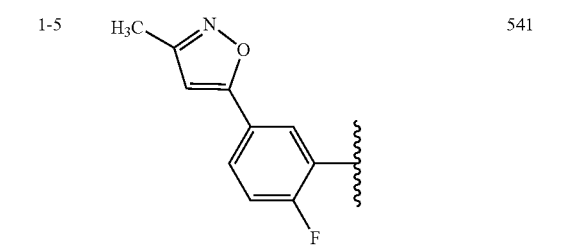 | 541 |
| 1-6 | 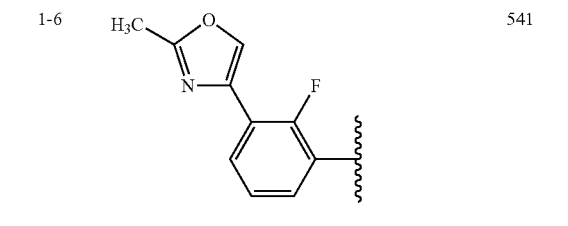 | 541 |
| 1-7 | 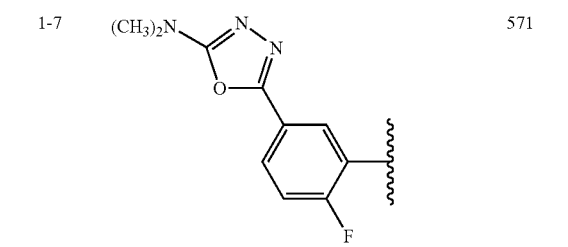 | 571 |
| 1-8 | 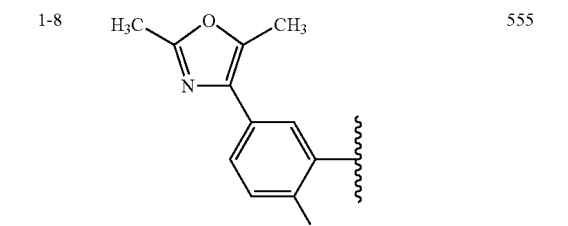 | 555 |
| 1-9 | 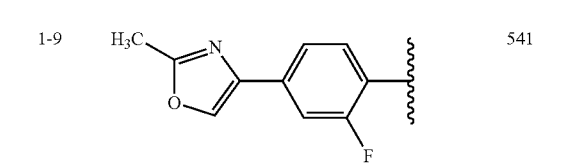 | 541 |
-continued
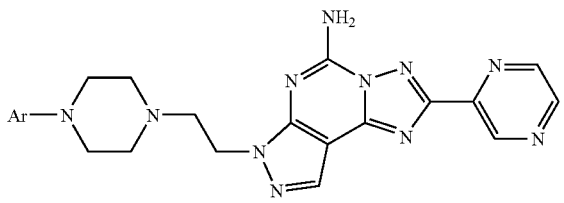
| Example | Ar | MS, m/e |
|---|---|---|
| 1-10 | 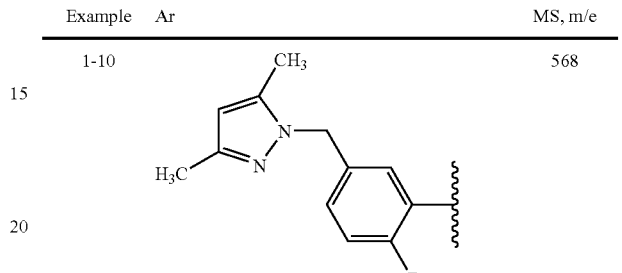 | 568 |
| 1-11 | 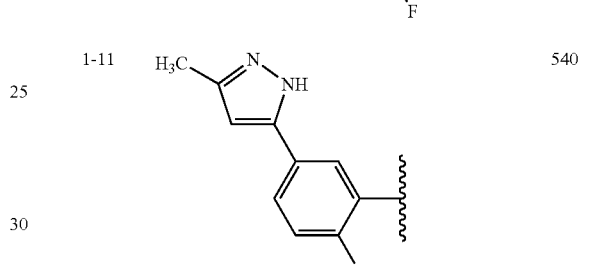 | 540 |
| 1-12 | 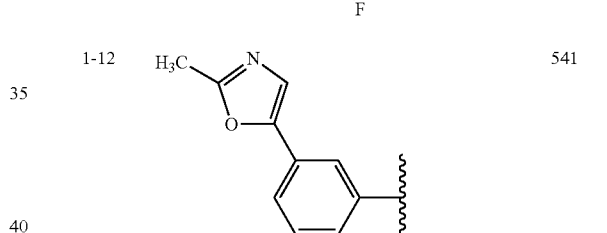 | 541 |
| 1-13 | 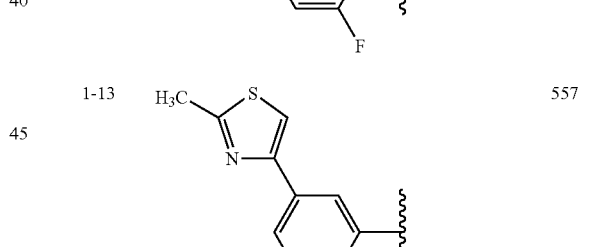 | 557 |
| 1-14 | 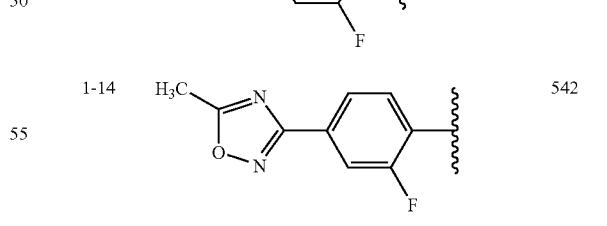 | 542 |
| 1-15 | 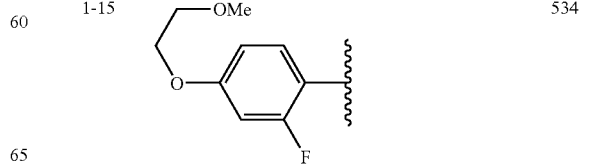 | 534 |

-continued
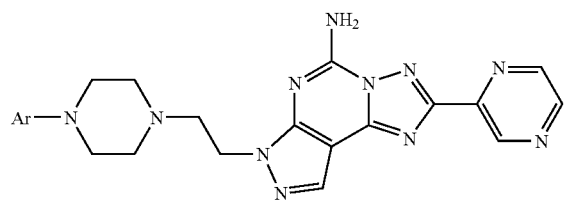
| Example | Ar | MS, m/e |
|---|---|---|
| 1-16 | 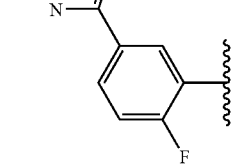 | 527 |
| 1-17 | 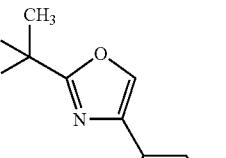 | 527 |
| 1-18 | 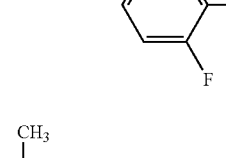 | 586 |
| 1-19 | 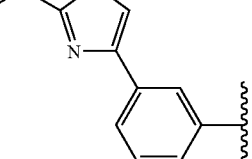 | 527 |
| 1-20 | 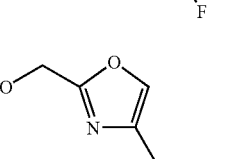 | 528 |
-continued
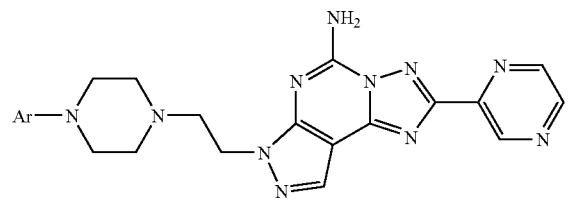
| Example | Ar | MS, m/e |
|---|---|---|
| 1-21 | (5-methoxymethyl-1,2,4-oxadiazol-3-yl)-4-fluorophenyl | 572 |
| 1-22 | (2-(2-hydroxypropan-2-yl)oxazol-4-yl)-4-fluorophenyl | 585 |
| 1-23 | (2-(1-hydroxyethyl)oxazol-4-yl)-4-fluorophenyl | 571 |
| 1-24 | (2-methoxymethyl-oxazol-4-yl)-4-fluorophenyl | 571 |
| 1-25 | 3-methyl-6-fluoro-1H-indazol-5-yl | 514 |

-continued

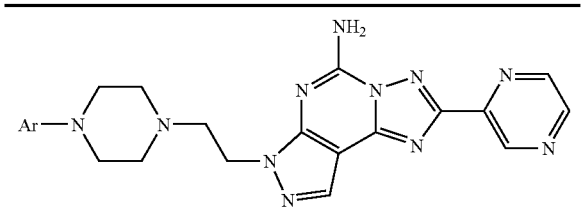

| Example | Ar | MS, m/e |
|---|---|---|
| 1-26 | 3-(5-methyl-1,2,4-oxadiazol-3-yl)phenyl | 524 |
| 1-27 | 2-acetyl-5-fluorobenzoxazol-6-yl | 543 |
| 1-28 | 2,4-difluorophenyl | 478 |
| 1-29 | 2-methyl-5-fluorobenzoxazol-6-yl | 515 |
| 1-30 | 2-methyl-5-fluorobenzoxazol-6-yl | 515 |
| 1-31 | 2-(acetoxymethyl)-5-fluorobenzoxazol-6-yl | 573 |
| 1-32 | 3-methyl-6-fluorobenzisoxazol-5-yl | 515 |

-continued

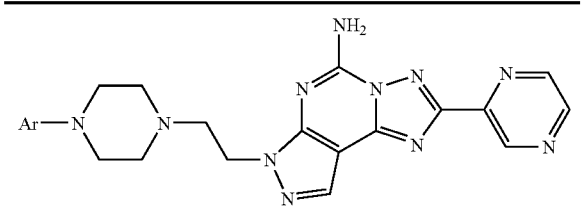

| Example | Ar | MS, m/e |
|---|---|---|
| 1-33 | 2-(methoxymethyl)-5-fluorobenzoxazol-6-yl | 545 |
| 1-34 | 2-(hydroxymethyl)-5-fluorobenzoxazol-6-yl | 531 |
| 1-35 | 2-ethyl-5-fluorobenzoxazol-6-yl | 529 |
| 1-36 | 2-(2,2,2-trifluoroethoxymethyl)-5-fluorobenzoxazol-6-yl | 613 |
| 1-37 | 2-(ethoxymethyl)-5-fluorobenzoxazol-6-yl | 559 |
| 1-38 | 2-acetyl-5-fluorobenzoxazol-6-yl | 543 |
| 1-39 | 2-(2-hydroxypropan-2-yl)-5-fluorobenzoxazol-6-yl | 559 |

-continued

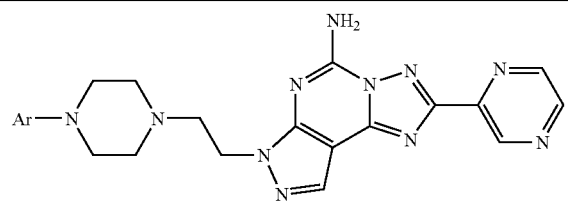

| Example | Ar | MS, m/e |
|---|---|---|
| 1-40 | 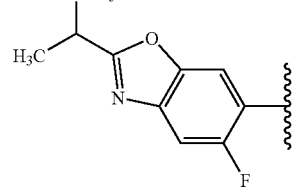 | 559 |
| 1-41 | 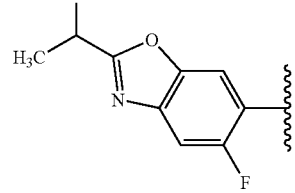 | 599 |
| 1-42 | 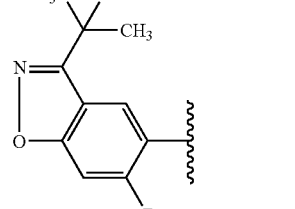 | 559 |

EXAMPLE 2

In similar fashion to Example 1, employing the aryl-piperazines from the Preparations section together with Preparation 2, prepare the following compounds:

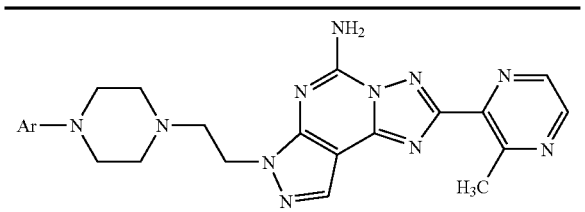

| Example | Ar | MS, m/e |
|---|---|---|
| 2-1 | 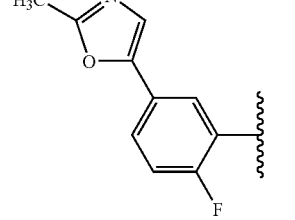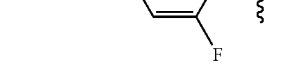 | 555 |

-continued

| Example | Ar | MS, m/e |
|---|---|---|
| 2-2 | H₃C group with oxadiazole–phenyl–F | 556 |
| 2-3 | (CH₃)₂N–oxadiazole–phenyl–F | 585 |
| 2-4 | oxazole–phenyl–F | 541 |
| 2-5 | H₃C–oxadiazole–phenyl–F | 556 |
| 2-6 | CH₂CH₂OMe–O–phenyl–F | 548 |
| 2-7 | F,F-phenyl | 492 |

-continued

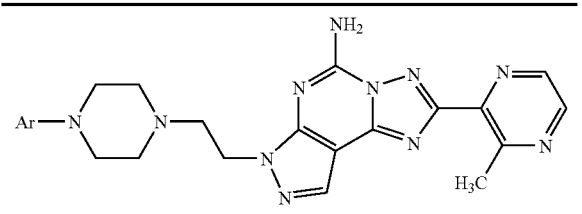

| Example | Ar | MS, m/e |
|---|---|---|
| 2-8 | 2-methyl-oxazol-4-yl-3-fluorophenyl | 555 |
| 2-9 | 4-methyl-pyrimidin-2-yl-4-fluorophenyl | 566 |
| 2-10 | NC-CH2-4-fluorophenyl | 513 |
| 2-11 | 1-methyl-pyrazol-3-yl-4-fluorophenyl | 554 |
| 2-12 | oxetan-3-yloxy-2-fluorophenyl | 546 |
| 2-13 | 2-methyl-oxazol-4-yl-3-fluorophenyl | 541 |
| 2-14 | pyrazol-1-ylmethyl-4-fluorophenyl | 554 |

-continued

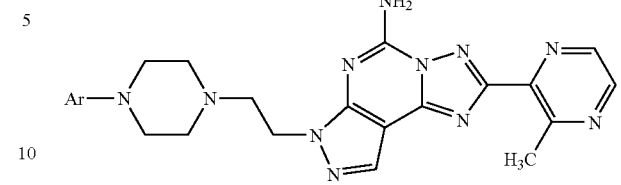

| Example | Ar | MS, m/e |
|---|---|---|
| 2-15 | 2-methyl-oxazol-5-yl-4-fluorophenyl | 555 |
| 2-16 | cyclopropyl(hydroxy)methyl-4-fluorophenyl | 544 |
| 2-17 | 1-hydroxycyclopropyl-4-fluorophenyl | 530 |
| 2-18 | 5-methyl-1H-pyrazol-3-yl-4-fluorophenyl | 554 |
| 2-19 | 1H-pyrazol-3-yl-4-fluorophenyl | 540 |

-continued

| Example | Ar | MS, m/e |
|---|---|---|
| 2-20 | 3-methylisoxazol-5-yl-(4-fluorophenyl) | 555 |
| 2-21 | oxazol-5-yl-(4-fluorophenyl) | 541 |
| 2-22 | 2-methylthiazol-4-yl-(4-fluorophenyl) | 571 |
| 2-23 | 5-(methoxymethyl)-1,2,4-oxadiazol-3-yl-(4-fluorophenyl) | 586 |
| 2-24 | 4-(2-hydroxyethoxy)-2-fluorophenyl | 534 |

-continued

| Example | Ar | MS, m/e |
|---|---|---|
| 2-25 | 5-(2-hydroxypropan-2-yl)-1,2,4-oxadiazol-3-yl-(4-fluorophenyl) | 600 |
| 2-26 | 4-(2-hydroxy-2-methylpropoxy)-2-fluorophenyl | 562 |
| 2-27 | 2-(1-hydroxy-2,2,2-trifluoroethyl)-6-fluorobenzoxazol-5-yl | 613 |
| 2-28 | oxazol-2-yl-(4-fluorophenyl) | 541 |

-continued
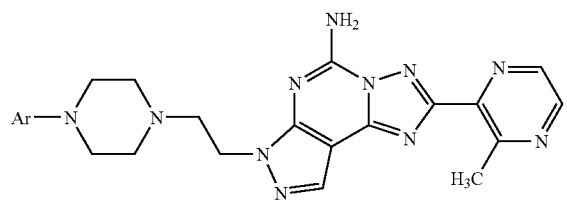
| Example | Ar | MS, m/e |
|---|---|---|
| 2-29 | 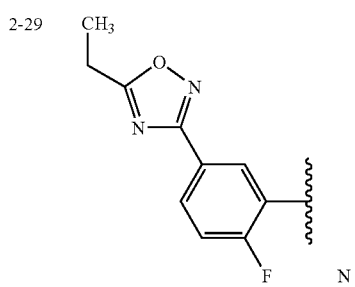 | 570 |
| 2-30 | 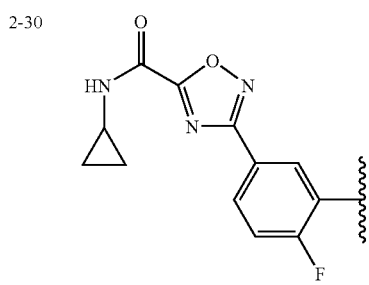 | 625 |
| 2-31 | 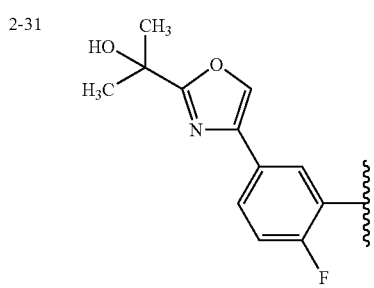 | 599 |
| 2-32 | 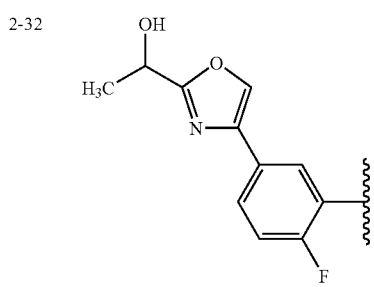 | 585 |
-continued
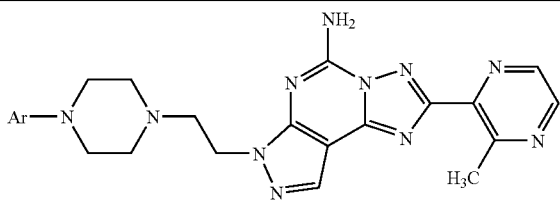
| Example | Ar | MS, m/e |
|---|---|---|
| 2-33 | 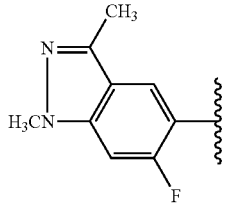 | 542 |
| 2-34 | 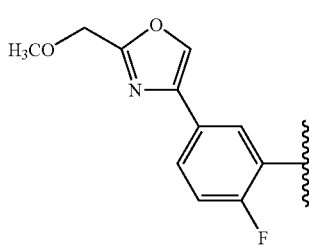 | 585 |
| 2-35 | 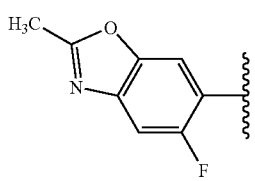 | 529 |
| 2-36 |  | 529 |
| 2-37 | 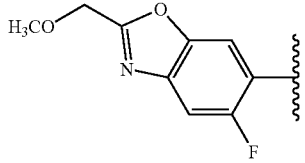 | 559 |
| 2-38 | 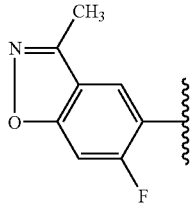 | 529 |

-continued

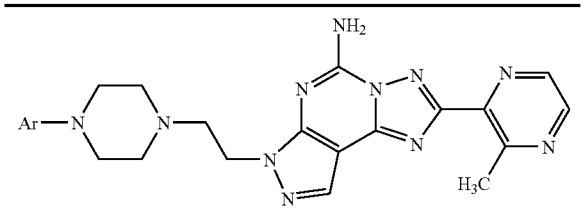

| Example | Ar | MS, m/e |
|---|---|---|
| 2-39 | 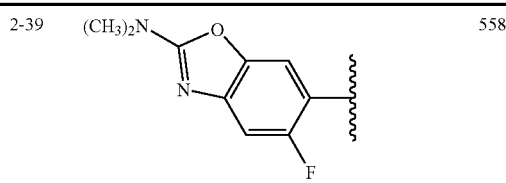 | 558 |
| 2-40 | 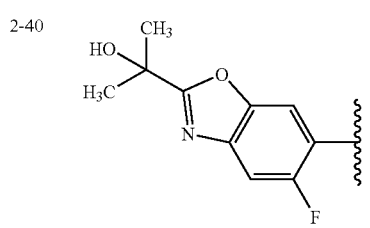 | 573 |
| 2-41 | 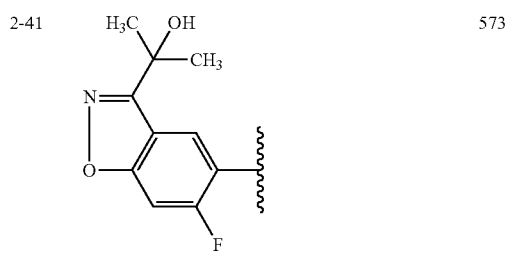 | 573 |

EXAMPLE 3

In similar fashion to Example 1, employing the aryl-piperazines from the Preparations section together with Preparation 2-4, prepare the following compounds:

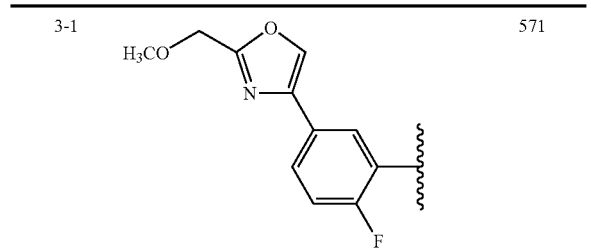

| Example | Ar | MS, m/e |
|---|---|---|
| 3-1 | (see structure below) | 571 |

-continued

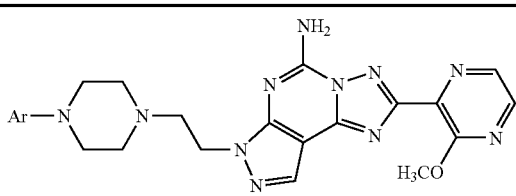

| Example | Ar | MS, m/e |
|---|---|---|
| 3-2 | 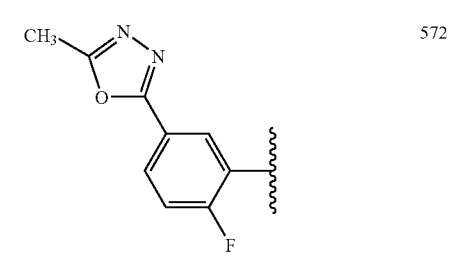 | 572 |
| 3-3 | 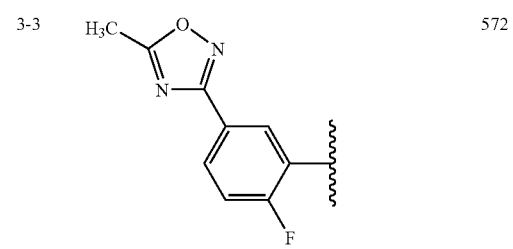 | 572 |

EXAMPLE 4

In similar fashion to Example 1, employing the aryl-piperazines from the Preparations section together with Preparation 2-5, prepare the following compounds:

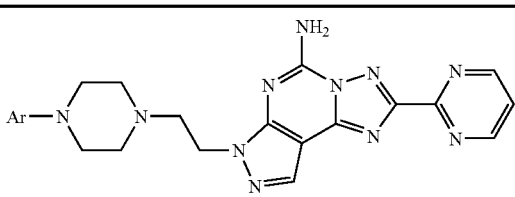

| Example | Ar | MS, m/e |
|---|---|---|
| 4-1 | 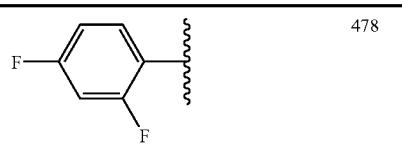 | 478 |
| 4-2 | 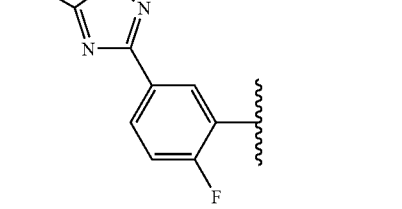 | 542 |

-continued

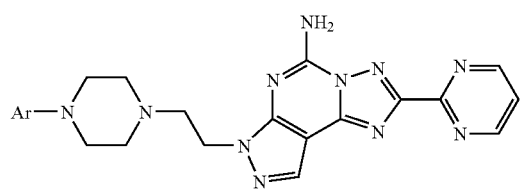

| Example | Ar | MS, m/e |
|---|---|---|
| 4-3 | H₃C-[benzoxazole-F] | 515 |
| 4-4 | H₃C-[benzoxazole-F] | 515 |
| 4-5 | [3-methyl-benzisoxazole-F] | 515 |
| 4-6 | F₃C-CH(OH)-[benzoxazole-F] | 599 |

EXAMPLE 5

In similar fashion to Example 1, employing Preparation 13 together with Preparation 2-10, prepare Example 5 as a yellow solid, MS: m/e 543 (M+1).

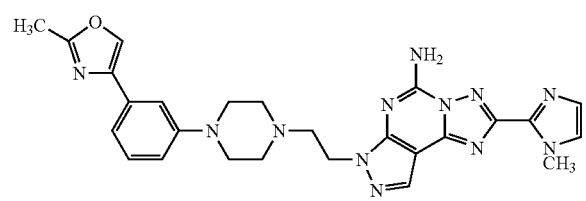

In like manner from 1-(2,4-difluorophenyl)piperazine and Preparation 2-11, prepare Example 5-2 as a yellow solid, MS: m/e 480 (M+1).

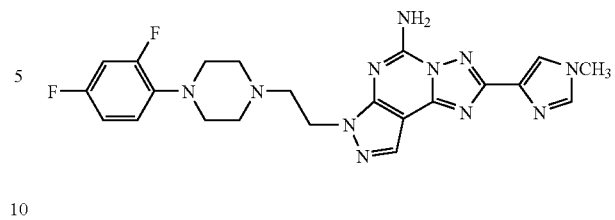

EXAMPLE 6

In similar fashion to Example 1, employing the aryl-piperazines from the Preparations section together with Preparation 2-13, prepare the following compounds:

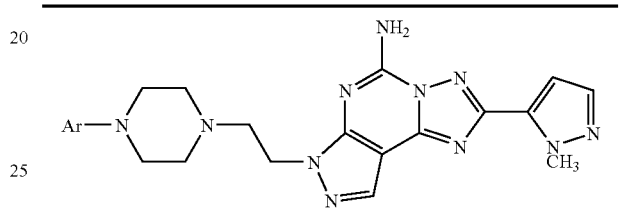

| Example | Ar | MS, m/e |
|---|---|---|
| 6-1 | H₃C-[oxazole]-[phenyl-F] | 543 |
| 6-2 | 2,4-difluorophenyl | 480 |

EXAMPLE 7

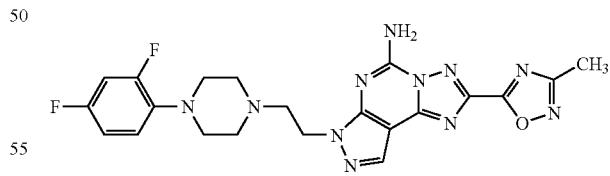

In similar fashion to Example 1, employing 1-(2,4-difluorophenyl)piperazine together with Preparation 2-12, prepare Example 7 as a yellow solid, MS: m/e 482 (M+1).

EXAMPLE 8

In similar fashion to Example 1, employing the aryl-piperazines from the Preparations section together with Preparation 2-7, prepare the following compounds:

| Example | Ar | MS, m/e |
|---|---|---|
| 8-1 | 2,4-difluorophenyl | 481 |
| 8-2 | 2-methyl-5-fluorobenzoxazol-6-yl | 518 |
| 8-3 | 2-methyl-6-fluorobenzoxazol-5-yl | 518 |

EXAMPLE 9

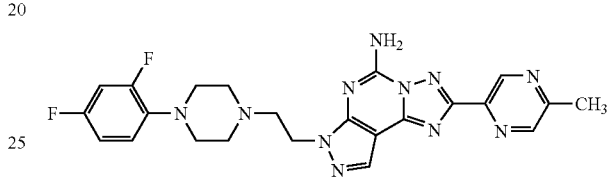

In similar fashion to Example 1, employing 1-(2,4-difluorophenyl)piperazine together with Preparation 2-8, prepare Example 9 as a yellow solid, MS: m/e 494 (M+1).

EXAMPLE 10

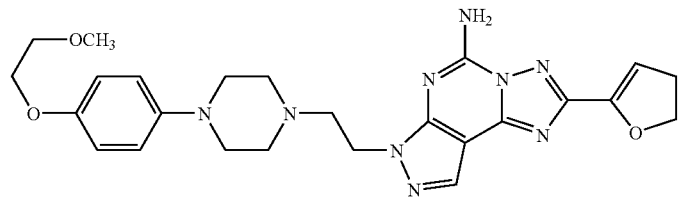

In similar fashion to Example 1, employing 1-(2,4-difluorophenyl)piperazine together with Preparation 2-2, prepare Example 10 as a yellow solid, MS: m/e 492 (M+1).

EXAMPLE 11

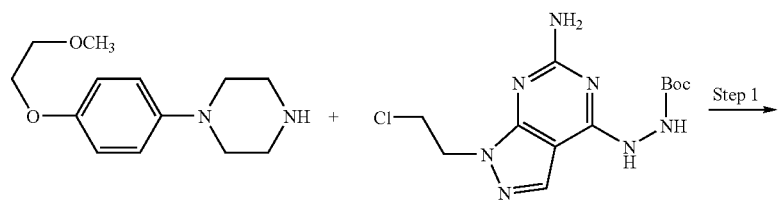

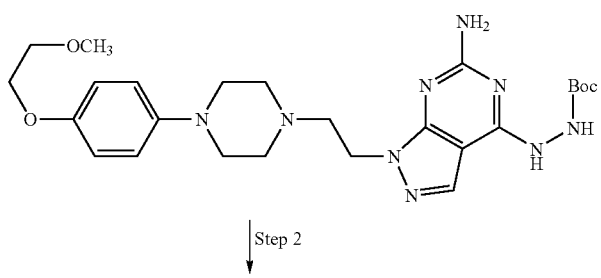

Step 1

Step 2

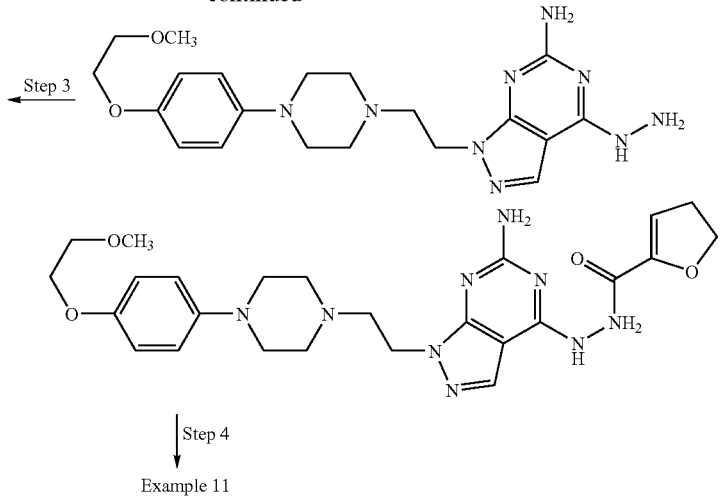

Step 3

Step 4

Example 11

Step 1: Combine the product of Preparation 1, Step 3 (6.04 g, 18.4 mmol), 1-(4-(2-methoxyethoxy)phenyl)piperazine (8.719, 37 mmol) and KI (3.06 g, 18.4 mmol) in DMF (60 ml). Heat at 90° C. 72 h. Allow to cool, concentrate and partition with $CH_2Cl_2$ and 1.0N NaOH. Wash with brine, dry ($MgSO_4$), concentrate and chromatograph on silica to obtain the alkylation product as a brown solid.

Step 2: Dissolve the product of Step 1 (6.0 g, 11 mmol) in 1:1 MeOH—$CH_2Cl_2$ (70 ml). Add 4.0M HCl/dioxane (35 ml, 40 mmol) and allow to stand 18 h. Add a solution of NaOH (7.0 g) in water (20 mh). Concentrate and wash with water, then EtOAc to obtain the hydrazine as a brown solid.

Step 3: Couple the product of Step 2 (0.100 g, 0.24 mmol) with 4,5-dihydrofuran-carboxylic acid (0.032 g, 0.28 mmol) according to the procedure of Preparation 2, Step 1, and purify by PLC to obtain the hydrazide as a yellow solid.

Step 4: To the product of Step 3 (0.89 g, 0.17 mmol) add BSA (6.0 ml). Heat at 130° C. 6 h, allow to cool, and concentrate. Combine with MeOH (20 ml) and water (1.0 ml), heat at reflux 0.5 h, and concentrate. Purify by PLC to obtain the title compound as a white solid, MS: m/e 506 (M+1).

Similarly, starting with the product of Preparation 1, Step 3, and 1-(2,4-difluoro-phenyl)piperazine, produce Example 11-2 as a yellow solid, MS: m/e 468 (M+1).

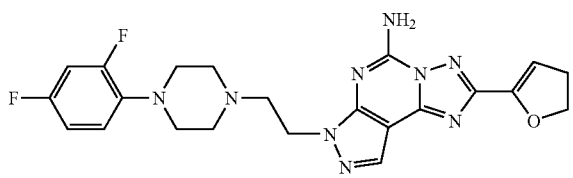

EXAMPLE 12

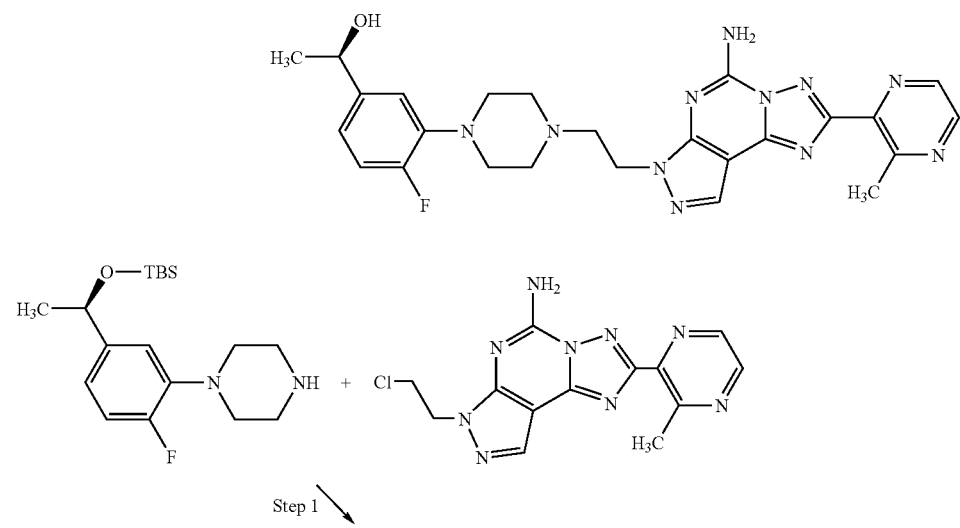

Step 1

-continued

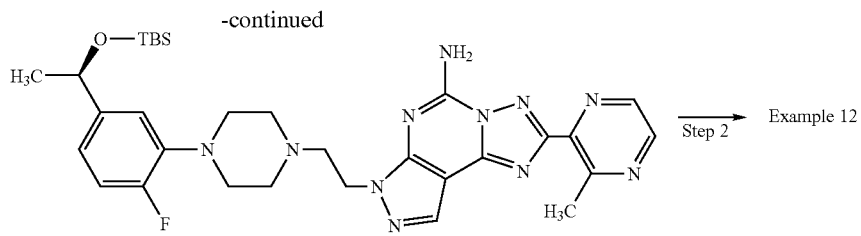

Step 2 → Example 12

Step 1: In similar fashion to Example 1, employ Preparation 2 together with Preparation 9-2 to obtain, without work-up, a solution of the crude silyl-protected compound.
Step 2: Treat the solution from Step 1 with TBAF (1.0M in THF, 1.5 equivalents) and stir 5 h. Concentrate and purify by PLC to obtain the title compound as a yellow solid, MS: m/e 518 (M+1).

EXAMPLE 13

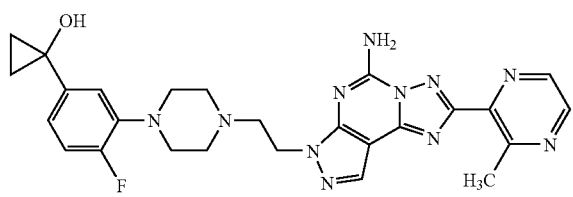

In similar fashion to Example 12, employing the silyl ether from Preparation 11, prepare the title compound as a yellow solid, MS: m/e 530 (M+1).

EXAMPLE 14

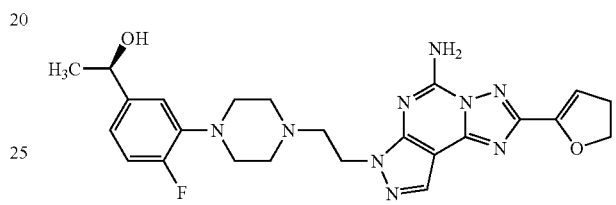

In similar fashion to Example 12, employing Preparation 2-6 together with Preparation 9-2, prepare the title compound as an off-white solid, MS: m/e 494 (M+1).

EXAMPLE 15

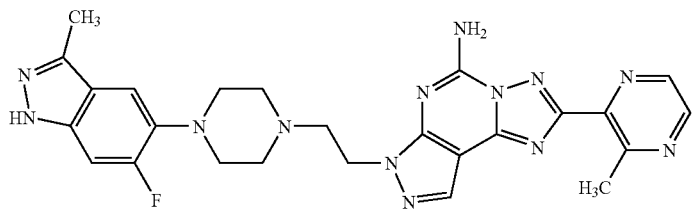

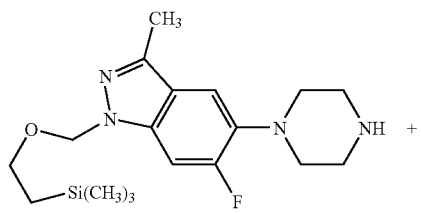  +

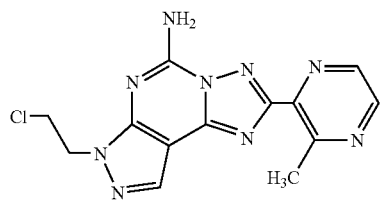

Step 1

-continued

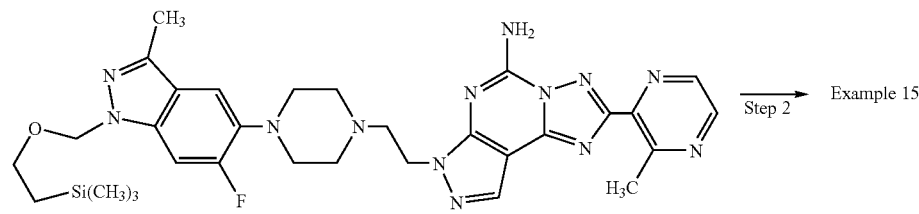

Step 1: In similar fashion to Example 1, employ Preparation 2 together with the product of Preparation 38, Step 2, to obtain, after purification by PLC, the alkylation product as a yellow solid.

Step 2: Combine the product of Step 1 (0.057 g, 0.087 mmol) with TBAF trihydrate (0.082 g, 0.26 mmol) and ethylenediamine (0.037 ml, 0.55 mmol) in DMF (0.5 ml). Heat at 80° C. 18 h, concentrate and purify by PLC to obtain the title compound as a yellow solid, MS: m/e 528 (M+1).

EXAMPLE 16

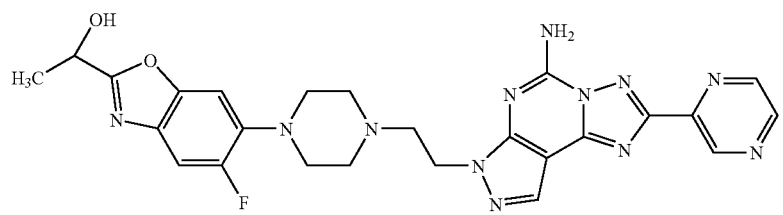

To a solution of the product of Example 1-27 (0.05 g, 0.09 mmol) in a mixture of 1:1 THF—CH$_3$OH (16 ml) add NaBH$_4$ (0.019, 0.26 mmol). Quench the reaction mixture after 1 h with satd. NH$_4$Cl and extract with EtOAc. Dry (K$_2$CO$_3$), concentrate, and purify by PLC (5% MeOH in CH$_2$Cl$_2$) to obtain the title compound as a yellow solid, MS: m/e 545 (M+1).

In similar fashion, employ the product of Preparation 43 with the product of Preparation 2 according to the procedure of Example 2 to provide the alkylation product, and reduce this with NaBH$_4$ as above. Purify the product by PLC to obtain Example 16-2 as a yellow solid, MS: m/e 559 (M+1).

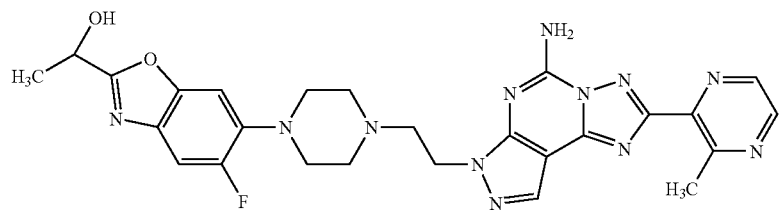

Because of their adenosine A$_{2a}$ receptor antagonist activity, compounds of the present invention are useful in the treatment of depression, cognitive function diseases and neurodegenerative diseases such as Parkinson's disease, senile dementia as in Alzheimer's disease, psychoses of organic origin, attention deficit disorders, EPS, dystonia, RLS and PLMS. In particular, the compounds of the present invention can improve motor-impairment due to neurodegenerative diseases such as Parkinson's disease.

In this specification, the term "at least one compound of formula I" means that one to three different compounds of formula I may be used in a pharmaceutical composition or method of treatment. Preferably one compound of formula I is used. Similarly, "one or more agents useful in the treatment of Parkinson's disease" means that one to three different agents, preferably one agent, may be used in a pharmaceutical composition or method of treatment. Preferably, one agent is used in combination with one compound of formula I.

The pharmacological activity of the compounds of the invention was determined by the following in vitro and in vivo assays to measure A$_{2a}$ receptor activity.

Human Adenosine A$_{2a}$ and A$_1$ Receitor Competition Binding Assay Protocol Membrane Sources:

A$_{2a}$: Human A$_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers:

Membrane dilution buffer: Dulbecco's Phosphate Buffered Saline (Gibco/BRL)+10 mM MgCl$_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, Amersham Pharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 1971, 6-OHDA and Cathecolamine Neurons, North Holland, Amsterdam, 101-127), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µl of saline with 0.05% ascorbic acid as antioxidant, and infused at the constant flow rate of 1 µl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

EPS Assay

The following procedure describes the use of an adenosine A2a antagonist to attenuate the Extra-Pyramidal Syndrome (EPS) displayed in *cebus apella* monkeys sensitized to the dopamine $D_2$ receptor antagonist, haloperidol.

A colony of *Cebus apella* monkeys previously sensitized to the chronic effects of haloperidol exhibits EPS when administered haloperidol acutely (0.3 mg/kg, p.o.). A test compound of formula I is administered orally (p.o.) at doses of 0.3-30 mg/kg, in conjunction with haloperidol. The studies are conducted using a within-subjects design such that each monkey receives all treatments (vehicle and doses of test compound) in a crossover, balanced design. The reduction in the maximum EPS score, as well as the dose-dependent delay in the onset of EPS are determined.

Clinical guidelines for the treatment of RLS and PLMS have been established: see A. L. Chesson et al, *Sleep*, 22, 7 (1999), p. 961-8. Efficacy of adenosine $A_{2a}$ antagonists in treating RLS and PLMS can be determined by a method analogous to the clinical method described in the literature for pramipexole and ropinerole by Weimerskirch et al, *Annals of Pharmacotherapy*, 35, 5 (2001), p. 627-30.

Using the above test procedures, the following results were obtained for preferred and/or representative compounds of the invention.

Results of the binding assay on compounds of the invention showed $A_{2a}$ Ki values of about 0.2 to about 30 nM, with preferred compounds showing Ki values between 0.2 and 5.0 nM. The compound of Example 1 had a Ki of 0.2 nM.

Selectivity is determined by dividing Ki for A1 receptor by Ki for A2a receptor. Preferred compounds of the invention have a selectivity ranging from about 50 to above 9000. The compound of Example 2-28 had a selectivity above 9000.

Preferred compounds showed a 50-75% decrease in descent latency when tested orally at 1 mg/kg for anti-cataleptic activity in rats.

In the 6-OHDA lesion test, rats dosed orally with 1 mg/kg of the preferred compounds performed 170-440 turns in the two-hour assay period.

In the haloperidol-induced catalepsy test, a combination of sub-threshold amount of a compound of formula I and a sub-threshold amount of L-DOPA showed a significant inhibition of the catalepsy, indicating a synergistic effect. In the 6-OHDA lesion test, test animals administered a combination of a compound of formula I and a sub-threshold amount of L-DOPA demonstrated significantly higher contralateral turning.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the other agents used in combination with the compounds of formula I, i.e., the Parkinson's Disease agents, the antipsychotics, tricyclcic antidepressants, anticonvulsants, dopamine agonists, benzodiazepines, opioids, lithium or iron, will be determined by the attending clinician in view of the approved doses and dosage regimen in the package insert, taking into consideration the age, sex and condition of the patient and the severity of the disease. When administered in combination, the compound of formula I and the other agent can be administered simultaneously or sequentially. This is particularly useful when the components of the combination are preferably given on different dosing schedules, e.g., one component is administered daily and the other every six hours, or when the preferred pharmaceutical compositions are different, e.g. one is preferably a tablet and one is a capsule. It is therefore advantageous to provide the compound of formula I and the other agent in a kit comprising, in separate containers in a single package, pharmaceutical compositions for use in combination to treat or prevent Parkinson's Disease, EPS, dystonia, RLS or PLMS, wherein one container comprises a pharmaceutical composition comprising an effective amount of a compound of formula I in a pharmaceutically acceptable carrier, and wherein a separate container comprises a pharmaceutical composition comprising an effective amount of another agent appropriate to treat the indicated condition.

Those skilled in the art will recognize that a dosage form for one of the components of the combination can be modified to contain both a compound of formula I and another agent, e.g., a compound of formula I and an antipsychotic or a compound of formula I and a dopamine agonist.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula

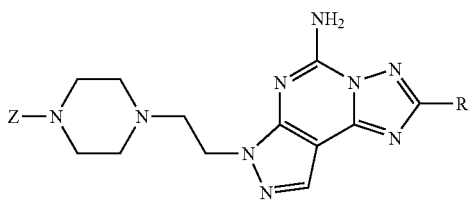

or a pharmaceutically acceptable salt thereof, wherein
R is $R^1$-isoxazolyl, $R^1$-oxadiazolyl, $R^1$-dihydrofuranyl, $R^1$-pyrazolyl, $R^1$-imidazolyl, $R^1$-pyrazinyl or $R^1$-pyrimidinyl;
$R^1$ is 1, 2 or 3 substituents independently selected from the group consisting of H, alkyl, alkoxy and halo;
Z is $R^2$-aryl or $R^2$-heteroaryl;
$R^2$ is 1 to 5 substituents independently selected from the group consisting of hydrogen, alkyl, hydroxyalkyl, -alkylene-O—C(O)alkyl, alkoxyalkyl, (hydroxy)haloalkyl, (cycloalkyl)hydroxyalkyl, hydroxycycloalkyl, (halo)alkoxyalkyl, —C(O)alkyl, hydroxyalkoxy, alkoxyalkoxy, oxetanyloxy, halo, cyanoalkyl, haloalkyl, dialkylamino, $R^3$-heteroaryl and $R^3$-heteroarylalkyl; and
$R^3$ is 1 to 3 substituents independently selected from the group consisting of H, alkyl, alkoxyalkyl, hydroxyalkyl, dialkylamino and cycloalkylaminocarbonyl.

2. A compound of claim 1 wherein R is $R^1$-pyrazinyl or $R^1$-dihydrofuranyl.

3. A compound of claim 2 wherein $R^1$ is one substituent selected from the group consisting of H and alkyl.

4. A compound of claim 1 wherein Z is $R^2$-phenyl and $R^2$ is 1 to 3 substituents independently selected from the group consisting of halo, alkoxyalkyl or $R^3$-heteroaryl.

5. A compound of claim 4 wherein $R^2$ is two substituents, and one substituent is 2-fluoro and the other is halo, alkoxyalkyl, or $R^3$-heteroaryl.

6. A compound of claim 5 wherein the heteroaryl group in $R^3$-heteroaryl is oxazolyl, 1,2,4-oxadiazolyl, isoxazolyl or thiazolyl, and the $R^3$ substituent is 1 or 2 groups independently selected from H, alkyl and alkoxyalkyl.

7. A compound of claim 1 wherein Z is $R^2$-benzoxazolyl, $R^2$-benzisoxazolyl or $R^2$-indazolyl and $R^2$ is 1 to 3 substituents independently selected from the group consisting of H, halo and alkyl.

8. A compound of claim 7 wherein Z is $R^2$-benzoxazolyl or $R^2$-benzisoxazolyl, and $R^2$ is two substituents, wherein one substituent is a fluoro group adjacent to the attachment point of Z and the other is H or an alkyl group on the oxazolyl or isoxazolyl portion of Z.

9. A compound of claim 7 wherein Z is $R^2$-indazolyl, and $R^2$ is three substituents, wherein one substituent is a fluoro group adjacent to the attachment point of Z and the other two are alkyl groups on the indazolyl portion of Z.

10. A compound of claim 1 selected from the group consisting of

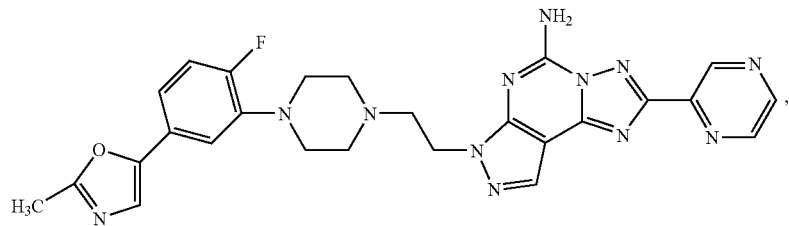

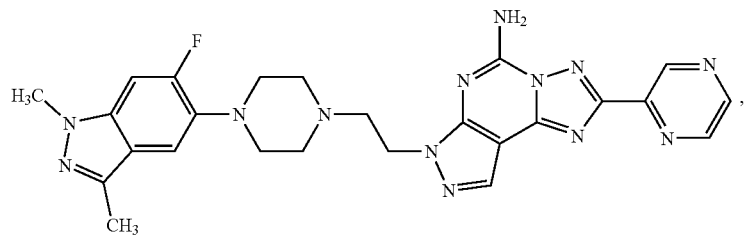

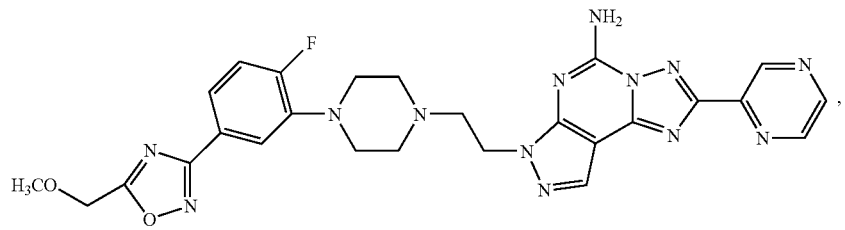

-continued
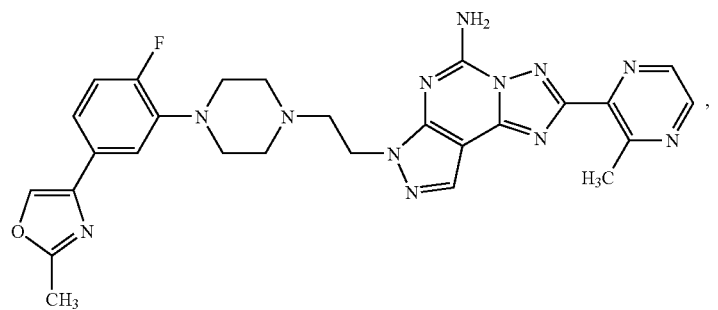
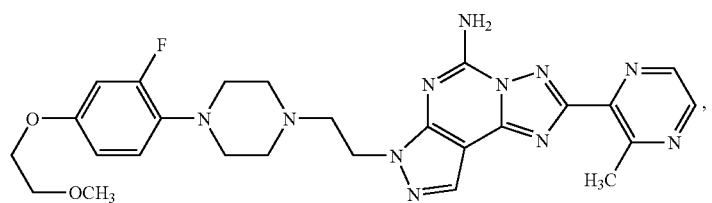
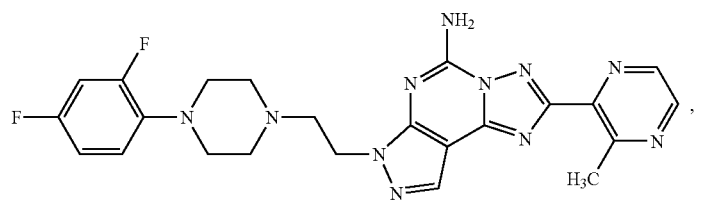
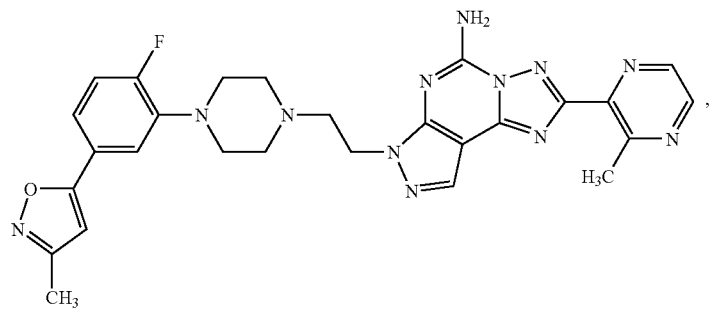
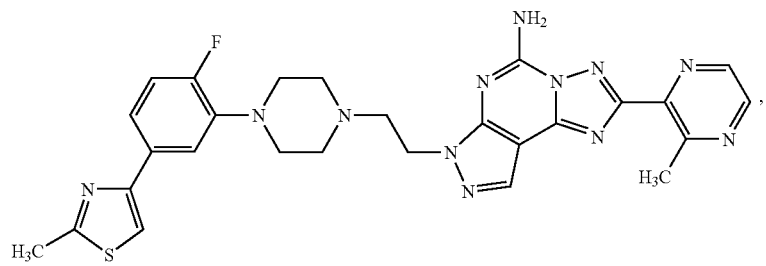
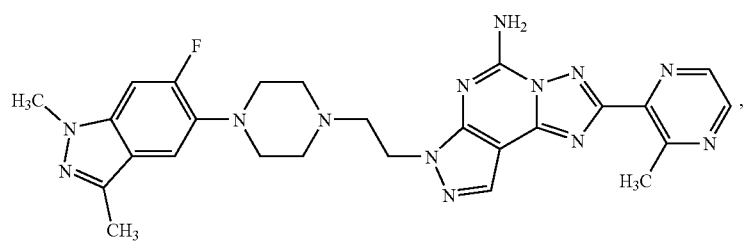

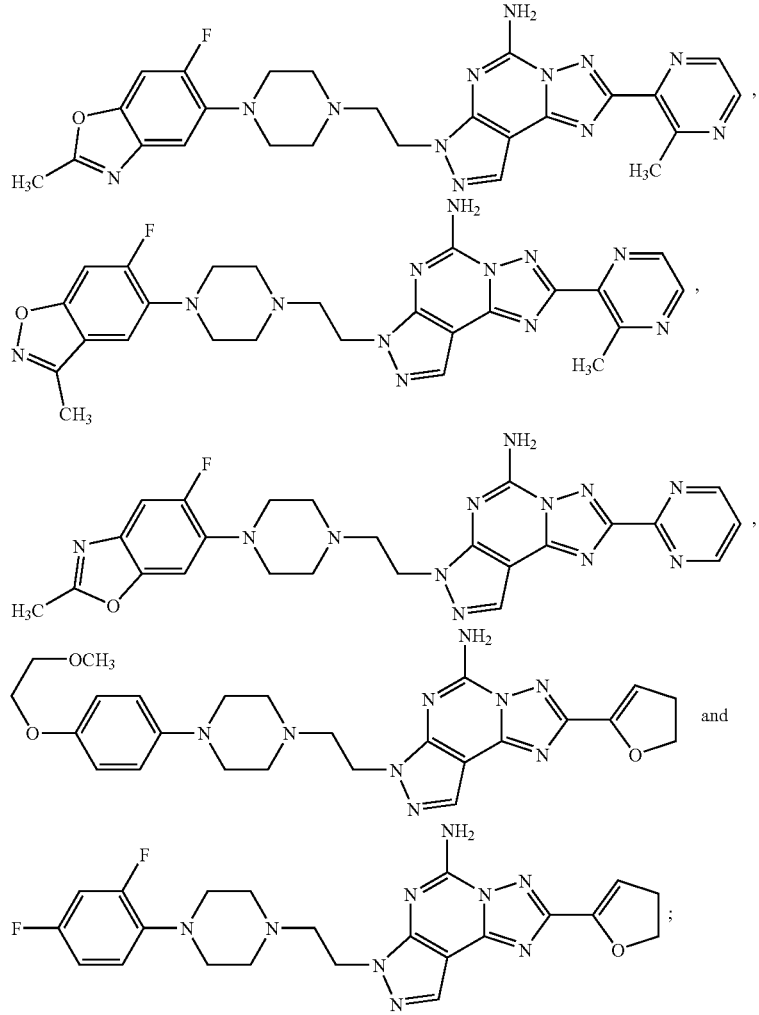

or a pharmaceutically acceptable salt thereof.

11. A pharmaceutical composition comprising a therapeutically effective amount of a compound of claim 1 in a pharmaceutically acceptable carrier.

12. A method of treating central nervous system diseases comprising administering an effective amount of a compound of claim 1 to a mammal in need of such treatment.

13. The method of claim 12 for treating Parkinson's disease, Extra Pyramidal Syndrome, restless legs syndrome, essential tremor, Huntington's Disease, attention deficit hyperactivity disorder, cognitive impairment, negative symptoms of schizophrenia, depression, stroke or psychoses.

14. The method of claim 13 for treating Parkinson's disease, Extra Pyramidal Syndrome, restless legs syndrome or attention deficit hyperactivity disorder.

15. A pharmaceutical composition comprising a therapeutically effective amount of a combination of a compound of claim 1, and 1 to 3 other agents useful in treating Parkinson's disease in a pharmaceutically acceptable carrier.

16. A method of treating Parkinson's disease comprising administering to a mammal in need of such treatment an effective amount of a combination of a compound of claim 1, and 1 to 3 other agents useful in treating Parkinson's disease.

17. The method of claim 16 wherein the other agents are selected from the group consisting of L-DOPA, dopaminergic agonists, MAO-B inhibitors, DOPA decarboxylase inhibitors and COMT inhibitors.

* * * * *